United States Patent
O'Reilly et al.

(10) Patent No.: US 10,100,087 B2
(45) Date of Patent: Oct. 16, 2018

(54) IMMUNOGENIC WT-1 PEPTIDES AND METHODS OF USE THEREOF

(71) Applicant: Memorial Sloan Kettering Cancer Center, New York, NY (US)

(72) Inventors: Richard J. O'Reilly, Roxbury, CT (US); Ekaterina Doubrovina, West Orange, NJ (US); Annamalai Selvakumar, Bronx, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 15/608,964

(22) Filed: May 30, 2017

(65) Prior Publication Data

US 2017/0334951 A1 Nov. 23, 2017

Related U.S. Application Data

(63) Continuation of application No. 14/372,174, filed as application No. PCT/US2013/021448 on Jan. 14, 2013, now abandoned.

(60) Provisional application No. 61/586,177, filed on Jan. 13, 2012, provisional application No. 61/647,207, filed on May 15, 2012.

(51) Int. Cl.
*A61K 39/00* (2006.01)
*C07K 7/06* (2006.01)
*C07K 7/08* (2006.01)

(52) U.S. Cl.
CPC ............ *C07K 7/08* (2013.01); *A61K 39/0011* (2013.01); *C07K 7/06* (2013.01); *A61K 2039/5158* (2013.01); *A61K 2039/55505* (2013.01); *A61K 2039/55516* (2013.01); *A61K 2039/55522* (2013.01); *A61K 2039/55527* (2013.01); *A61K 2039/55566* (2013.01); *A61K 2039/55577* (2013.01); *A61K 2039/55594* (2013.01)

(58) Field of Classification Search
None
See application file for complete search history.

(56) References Cited

U.S. PATENT DOCUMENTS

| | | | |
|---|---|---|---|
| 5,229,115 A | 7/1993 | Lynch | |
| 5,622,835 A | 4/1997 | Herlyn et al. | |
| 5,633,142 A | 5/1997 | Herlyn et al. | |
| 5,726,288 A | 3/1998 | Call et al. | |
| 5,981,217 A | 11/1999 | Subramaniam et al. | |
| 6,156,316 A | 12/2000 | Scheinberg et al. | |
| 6,207,375 B1 | 3/2001 | Subramaniam et al. | |
| 6,316,599 B1 | 11/2001 | Call et al. | |
| 6,593,299 B1 | 7/2003 | Bennett et al. | |
| 6,805,861 B2 | 10/2004 | Stauss | |
| 6,861,234 B1 | 3/2005 | Simard et al. | |
| 7,030,212 B1 | 4/2006 | Sugiyama et al. | |
| 7,063,854 B1 | 6/2006 | Gaiger et al. | |
| 7,115,272 B1 | 10/2006 | Gaiger et al. | |
| 7,144,581 B2 | 12/2006 | Gaiger et al. | |
| 7,323,181 B2 | 1/2008 | Gaiger et al. | |
| 7,329,410 B1 | 2/2008 | Gaiger et al. | |
| 7,368,119 B2 | 5/2008 | Gaiger et al. | |
| 7,420,034 B2 | 9/2008 | Sugiyama et al. | |
| 7,488,718 B2 | 2/2009 | Scheinberg et al. | |
| 7,517,950 B2 | 4/2009 | Sugiyama et al. | |
| 7,553,494 B2 | 6/2009 | Gaiger et al. | |
| 7,597,894 B2 | 10/2009 | Graddis et al. | |
| 7,598,221 B2 | 10/2009 | Scheinberg et al. | |
| 7,608,685 B1 | 10/2009 | Sugiyama et al. | |
| 7,655,249 B2 | 2/2010 | Gaiger et al. | |
| 7,662,386 B2 | 2/2010 | Gaiger et al. | |
| 7,666,985 B2 | 2/2010 | Sugiyama et al. | |
| 7,807,792 B2 | 10/2010 | Sugiyama et al. | |
| 7,833,775 B2 | 11/2010 | Dubensky et al. | |
| 7,901,693 B2 | 3/2011 | Gaiger et al. | |
| 7,915,393 B2 | 3/2011 | Gaiger et al. | |
| 7,939,627 B2 | 5/2011 | Nishihara et al. | |
| 8,071,732 B2 | 12/2011 | Gaiger et al. | |
| 8,105,604 B2 | 1/2012 | Sugiyama | |
| 8,216,595 B2 | 7/2012 | Moon et al. | |
| 8,288,355 B2 | 10/2012 | Sugiyama et al. | |
| 8,529,904 B2 | 9/2013 | Stauss et al. | |
| 8,557,247 B2 | 10/2013 | Lemoine | |
| 8,735,357 B2 | 5/2014 | Sugiyama | |
| 8,765,687 B2 | 7/2014 | Scheinberg et al. | |
| 8,771,702 B2 | 7/2014 | Paterson et al. | |
| 8,778,350 B2 | 7/2014 | Sugiyama | |
| 8,920,776 B2 | 12/2014 | Gaiger et al. | |
| 9,045,556 B2 | 6/2015 | Udaka et al. | |
| 9,181,302 B2 | 11/2015 | Li et al. | |

(Continued)

FOREIGN PATENT DOCUMENTS

| | | | |
|---|---|---|---|
| EP | 2998740 A1 | 3/1916 | |
| EP | 1447091 A1 | 8/2004 | |

(Continued)

OTHER PUBLICATIONS

Bellantuono et al. "Two distinct HLA-A0201—presented epitopes of the Wilms tumor antigen 1 can function as targets for leukemia-reactive CTL" Blood. Nov. 15, 2002;100(10):3835-7.

(Continued)

*Primary Examiner* — Daniel C Gamett
(74) *Attorney, Agent, or Firm* — Mark S. Cohen; Pearl Cohen Zedek Latzer Baratz LLP

(57) ABSTRACT

This invention provides peptides, immunogenic compositions and vaccines, and methods of treating, reducing the incidence of, and inducing immune responses to a WT-1-expressing cancer, comprising peptides derived from the WT-1 protein.

30 Claims, 11 Drawing Sheets

Specification includes a Sequence Listing.

(56) References Cited

U.S. PATENT DOCUMENTS

| | | | |
|---|---|---|---|
| 9,216,205 | B2 | 12/2015 | Chakraborty et al. |
| 9,226,955 | B2 | 1/2016 | Hilton et al. |
| 9,233,149 | B2 | 1/2016 | Scheinberg et al. |
| 9,248,173 | B2 | 2/2016 | Li et al. |
| 9,265,816 | B2 | 2/2016 | Scheinberg et al. |
| 9,266,932 | B2 | 2/2016 | Sugiyama |
| 9,272,026 | B2 | 3/2016 | Sugiyama |
| 9,403,886 | B2 | 8/2016 | Sugiyama |
| 9,499,602 | B2 | 11/2016 | Paterson et al. |
| 9,518,126 | B2 | 12/2016 | Kang et al. |
| 2002/0127718 | A1 | 9/2002 | Kuppner et al. |
| 2003/0032050 | A1 | 2/2003 | Berzofsky et al. |
| 2003/0045499 | A1 | 3/2003 | Gabrilovich et al. |
| 2003/0072761 | A1 | 4/2003 | Gaiger et al. |
| 2003/0082194 | A1 | 5/2003 | Gaiger et al. |
| 2003/0175272 | A1 | 9/2003 | Gruenberg |
| 2004/0018204 | A1 | 1/2004 | Gaiger et al. |
| 2005/0002951 | A1 | 1/2005 | Sugiyama et al. |
| 2005/0214268 | A1 | 2/2005 | Cavanaugh et al. |
| 2005/0119185 | A1 | 6/2005 | Scheinberg et al. |
| 2005/0147621 | A1 | 7/2005 | Higgins et al. |
| 2005/0221481 | A1 | 10/2005 | Migliaccio et al. |
| 2005/0260217 | A1 | 11/2005 | Johnson et al. |
| 2006/0057130 | A1 | 3/2006 | Nair et al. |
| 2006/0083716 | A1 | 4/2006 | Kaufman et al. |
| 2006/0084609 | A1 | 4/2006 | Scheinberg et al. |
| 2006/0165708 | A1 | 7/2006 | Mayumi et al. |
| 2007/0082860 | A1 | 4/2007 | Sugiyama et al. |
| 2007/0128207 | A1 | 6/2007 | Sugiyama et al. |
| 2007/0298093 | A1 | 12/2007 | Kanur et al. |
| 2008/0070835 | A1 | 3/2008 | Sugiyama et al. |
| 2009/0143291 | A1 | 6/2009 | Sugiyama et al. |
| 2010/0034842 | A1 | 2/2010 | Graddis et al. |
| 2010/0040614 | A1 | 2/2010 | Ahmed et al. |
| 2010/0092522 | A1 | 4/2010 | Scheinberg et al. |
| 2010/0111986 | A1 | 5/2010 | Scheinberg et al. |
| 2010/0166738 | A1 | 7/2010 | Gaiger et al. |
| 2010/0247556 | A1 | 9/2010 | Sugiyama |
| 2011/0070251 | A1 | 3/2011 | Sugiyama et al. |
| 2011/0136141 | A1 | 6/2011 | Adamczyk et al. |
| 2011/0223187 | A1 | 9/2011 | Shahabi et al. |
| 2011/0287055 | A1 | 11/2011 | Lauer et al. |
| 2011/0318380 | A1 | 12/2011 | Brix et al. |
| 2012/0301492 | A1 | 11/2012 | Gaiger et al. |
| 2013/0064812 | A1 | 3/2013 | Gallatin et al. |
| 2013/0196427 | A1 | 8/2013 | Sugiyama |
| 2013/0243800 | A1 | 9/2013 | Sugiyama |
| 2013/0266958 | A1 | 10/2013 | Sugiyam et al. |
| 2014/0086831 | A1 | 3/2014 | Scheinberg et al. |
| 2014/0179004 | A1 | 6/2014 | Fujii et al. |
| 2014/0220055 | A1 | 8/2014 | Okubo et al. |
| 2014/0220057 | A1 | 8/2014 | Okubo et al. |
| 2014/0220059 | A1 | 8/2014 | Asari et al. |
| 2014/0220105 | A1 | 8/2014 | Maeda et al. |
| 2014/0255941 | A1 | 9/2014 | Sugiyama |
| 2014/0271693 | A1 | 9/2014 | Nakatani |
| 2014/0341939 | A1 | 11/2014 | Udaka |
| 2015/0030533 | A1 | 1/2015 | Algate et al. |
| 2015/0118208 | A1 | 4/2015 | Schmitt et al. |
| 2015/0150975 | A1 | 6/2015 | Tanka et al. |
| 2015/0328278 | A1 | 11/2015 | Kubo et al. |
| 2015/0329874 | A1 | 11/2015 | Fukumura et al. |
| 2015/0352201 | A1 | 12/2015 | Scheinberg et al. |
| 2015/0368612 | A1 | 12/2015 | Palucka et al. |
| 2016/0058852 | A1 | 3/2016 | Ter Meulen et al. |
| 2016/0058854 | A1 | 3/2016 | Bender et al. |
| 2016/0068801 | A1 | 3/2016 | Lubenau |
| 2016/0084841 | A1 | 3/2016 | Sugiyama et al. |
| 2016/0030536 | A1 | 4/2016 | Weiner et al. |
| 2016/0114017 | A1 | 4/2016 | Okada |
| 2016/0114019 | A1 | 4/2016 | Li et al. |
| 2016/0166665 | A1 | 6/2016 | Ito |
| 2016/0176939 | A1 | 6/2016 | Sugiyama |
| 2016/0201141 | A1 | 7/2016 | Albitar et al. |
| 2016/0280756 | A1 | 9/2016 | Smith et al. |
| 2016/0317634 | A1 | 11/2016 | Springer et al. |
| 2016/0362465 | A1 | 12/2016 | Nishimura et al. |
| 2016/0367649 | A1 | 12/2016 | Sugiyama |
| 2016/0368948 | A1 | 12/2016 | Scheinberg et al. |
| 2017/0007693 | A1 | 1/2017 | Weinder et al. |
| 2017/0072038 | A1 | 3/2017 | Sugiyam et al. |

FOREIGN PATENT DOCUMENTS

| | | | |
|---|---|---|---|
| EP | | 1961761 A1 | 8/2008 |
| EP | | 2070947 A1 | 6/2009 |
| EP | | 2228072 A1 | 9/2010 |
| EP | | 2338509 A2 | 6/2011 |
| EP | | 2762156 A1 | 8/2014 |
| EP | | 2762159 A1 | 8/2014 |
| EP | | 2565201 B1 | 11/2014 |
| EP | | 1951281 B1 | 4/2015 |
| EP | | 2010209 B1 | 6/2015 |
| EP | | 2933261 A1 | 10/2015 |
| EP | | 2119778 B1 | 11/2015 |
| EP | | 2982681 A1 | 2/2016 |
| EP | | 2283112 B1 | 10/2016 |
| EP | | 3112378 A1 | 1/2017 |
| EP | | 3117836 A1 | 1/2017 |
| WO | WO 1995/029240 | | 11/1995 |
| WO | WO 1996/035438 A1 | | 11/1996 |
| WO | WO 1997/011091 | | 3/1997 |
| WO | WO 1999/038973 A2 | | 8/1999 |
| WO | WO 2000/006602 | | 2/2000 |
| WO | WO 2000/026249 A1 | | 5/2000 |
| WO | WO 2000/037491 | | 6/2000 |
| WO | WO 2000/055351 | | 9/2000 |
| WO | WO 2001/025273 A2 | | 4/2001 |
| WO | WO 2001/062920 | | 8/2001 |
| WO | WO 2002/028414 A1 | | 4/2002 |
| WO | WO 2003/037060 A2 | | 5/2003 |
| WO | WO 2004/111075 A2 | | 12/2004 |
| WO | WO 2005/053618 | | 6/2005 |
| WO | WO 2007/047764 A2 | | 4/2007 |
| WO | WO 2007/120603 | | 10/2007 |
| WO | WO 2007/120673 A2 | | 10/2007 |
| WO | WO 2010/037395 A2 | | 4/2010 |
| WO | WO 2014/113490 | | 7/2014 |
| WO | WO 2016/093326 A1 | | 6/2016 |
| WO | WO 2016/208332 | | 12/2016 |
| WO | WO 2017/049074 | | 3/2017 |

OTHER PUBLICATIONS

Bergmann et al. "High levels of Wilms' tumor gene (wt1) mRNA in acute myeloid leukemias are associated with a worse long-term outcome" Blood. Aug. 1, 1997;90(3):1217-25.

Borbulevych et al. "Structures of native and affinity-enhanced WT1 epitopes bound to HLA-A* 0201; implications for WT1-based cancer therapeutics" Molecular immunology. Sep. 30, 2010;47(15):2519-24.

Bruening et al. "A non-AUG translational initiation event generates novel WT1 isoforms" Journal of Biological Chemistry. Apr. 12, 1996;271(15):8646-54.

Buzyn et al. Peptides derived from the whole sequence of BCR-ABL bind to several class I molecules allowing specific induction of human cytotoxic T lymphocytes European journal of immunology. Aug. 1, 1997;27(8):2066-72.

Call et al. "Isolation and characterization of a zinc finger polypeptide gene at the human chromosome 11 Wilms' tumor locus" Cell. Feb. 9, 1990;60(3):509-20.

Cathcart et al. "All CML patients vaccinated with a multivalent bcr-abl peptide vaccine show specific immune responses in a phase II trial" Blood, 2001. 98(11): p. 728a-728a.

Cathcart et al. "A multivalent bcr-abl fusion peptide vaccination trial in patients with chronic myeloid leukemia". Blood. Feb. 1, 2004;103(3)1037-42.

Cheever et al. "The prioritization of cancer antigens: a national cancer institute pilot project for the acceleration of translational research" Clinical Cancer Research. Sep. 1, 2009;15(17):5323-37.

(56) References Cited

OTHER PUBLICATIONS

Chen et al. "Expression patterns of WT-1 and Bcr-Abl measured by TaqMan quantitative real-time RT-PCR during follow-up of leukemia patients with the Ph chromosome" Chinese medical journal. Jul. 2004;117(7):968-71.
Cilloni et al. "Significant correlation between the degree of WT-1 expression and the International Prognostic Scoring System Score in patients with myelodysplastic syndromes" J Olin Oncol. 2003,21(10):1988-1995.
Clay et al. "Changes in the fine specificity of gp100 (209-217)-reactive T cells in patients following vaccination with a peptide modified at an HLA-A2. 1 anchor residue". The Journal of Immunology. Feb. 1, 1999;162(3):1749-55.
Dao et al. "An immunogenic WT1-derived peptide that induces T cell response in the context of HLA-A* 02: 01 and HLA-A* 24: 02 molecules" OncoImmunology. Feb. 1, 2017;6(2):e1252895.
Database BIOSIS [online]; Nov. 16, 2003, pinilla Javier et al, "Breaking tolerance to the bcr/abl p201 b2a2 protein by use of mutated, heterocltic breakpoint peptides"; Database accession No. PREV200400147743, Abstract; and Blood vol. 102 No. 11, Nov. 16, 2003, p. 654a, 45th annual meeting of the American Society of Hematology, Dec. 6-9, 2003.
Database BISIS [online]; Nov. 16, 2003, Pinilla Javier et al, "Breaking tolerance to the bcr/abl p201 b2a2 protein by use of mutated, heterocltic breakpoint peptides"; Database accession No. PREV200400147740, Abstract; and Blood vol. 102 No. 11, Nov. 16, 2003, p. 654a, 45th annual meeting of the American Society of Hematology, Dec. 6-9, 2003.
De Groot et al. "An interactive Web site providing major histocompatibility ligand predictions: application to HIV research" AIDS research and human retroviruses. May 1, 1997;13(7):529-31.
Doubrovina et al. "In vitro stimulation with WT1 peptide-loaded Epstein-Barr virus-positive B cells elicits high frequencies of WT1 peptide-specific T cells with in vitro and in vivo tumoricidal activity" Clinical Cancer Research. Nov. 1, 2004;10(21):7207-19.
Doubrovina et al. "Sensitization of Human T Cells with Overlapping Pentadecapeptides Spanning the Wt1 Protein Induces Expansion of Leukemocidal T Cells Specific for Both Previously Identified and Novel WT1 Epitopes" Blood. Nov. 16, 2004;104(11):3873-.
Doubrovina et al. "Generation of T Cells of Desired HLA Restriction Specific for Epitopes of a Self-Antigen, WT1, for the Adoptive Immunotherapy of WT1 Positive Malignancies Using a Panel of Artificial Antigen Presenting Cells Expressing Prevalent HLA Alleles" Blood. Nov. 20, 2009;114(22):4086-.
Doubrovina et al. "Mapping of novel peptides of WT-1 and presenting HLA alleles that induce epitope-specific HLA-restricted T cells with cytotoxic activity against WT-1+ leukemias", Blood. Aug. 23, 2012;120(8):1633-46.
Doubrovina et al. "Leukernia-Reactive Cytotoxic CD8+ and CD4+ T-Cells Specific for Novel WT-1 Epitopes Are Generated In Vitro by Sensitization with Overlapping Pentadecapeptides (15-mers) Spanning the Wilms Tumor Protein" Blood. Nov. 16, 2007;110(11):1810-.
Dyall et al. "Heteroclitic immunization induces tumor immunity" Journal of Experimental Medicine. Nov. 2, 1998;188(9):1553-61.
Elisseeva et al. "Humoral immune responses against Wilms tumor gene WT1product in patients with hematopoietic malignancies" Blood. May 1, 2002;99(9):3272-9.
Ellisen et al. "The Wilms tumor suppressor WT1 directs stage-specific quiescence and differentiation of human hematopoietc progenitor cells" The EMBO Journal. Apr. 17, 2001;20(8):1897-909.
Fujiki et al. "A WT1 protein-derived, naturally processed 16-mer peptide, WT1332, is a promiscuous helper peptide for induction, of WT1-specific Th1-type CD4+ T cells" Microbiology and immunology. Dec. 1, 2008;52(12):591-600.
Gaiger et al. "Immunity to WT1 in the animal model and in patients with acute myeloid leukemia" Blood. Aug. 15, 2000;96(4)1480-9.
Gao et al. "Human cytotoxic T lymphocytes specific for Wilms' tumor antigen-1 inhibit engraftment of leukemia-initiating stem cells in non-obese diabetic-severe combined immunodeficient recipients" Transplantation. May 15, 2003;75(9)1429-36.
Gao e al. "Selective elimination of leukemic CD34+ progenitor cells by cytotoxic T lymphocytes specific for WT1" Blood. Apr. 1, 2000;95(7):2198-203.
Gao et al. "Antigen-specific CD4+ T-cell help is required to activate a memory CD8+ T cell to a fully functional tumor killer cell" Cancer research. Nov. 15, 2002;62(22):6438-41.
Gerber et al. "Characterization of chronic myeloid leukemia stem cells" American journal of hematology. Jan. 1, 2011;86(1):31-7.
Gessler et al. Homozygous deletion in Wilms tumours of a zinc-finger aene identified by chromosome jumping. Nature. Feb. 22, 1990;343(6260):774.
Gillmore et al. "Detection of Wilms' tumor antigen-specific CTL in tumor-draining lymph nodes of patients with early breast cancer" Clinical Cancer Research. Jan. 1, 2006;12(1):34-42.
Graff-Dubois et al. "Generation of CTL recognizing an HLA-A* 0201-restricted epitope shared by MAGE-A1,-A2,-A3,-A4,-A6,-A10, and-A12 tumor antigens: implication in a broad-spectrum tumor immunotherapy" The Journal of Immunology. Jul. 1, 2002;169(1):575-80.
Greco et al. "Two brc-abl junction peptides bind HLA-A3 molecules and allow specific induction of human cytotoxic T lymphocytes". Leukemia. Apr. 1996;10(4):693-9.
Greiner et al. "Leukemia-associated antigens are critical for the proliferation of acute myeloid leukemia cells" Clinical Cancer Research. Nov. 15, 2008;14(22):7161-6.
Haber et al. "Alternative splicing and genomic structure ol the Wilms tumor gene WT1" Proceedings of the National Academy of Sciences. Nov. 1, 1991;88(21):9618-22.
Healthline.om, "Non-hodgkin's Lymphoma: In Depth-Overview", pp. 1-3, http://www.healthline.com/channel/non-hodgkins-lymphoma indepth-overview, Dec. 2, 2008.
Hosen et al. "Very low frequencies of human normal CD34+ haematopoietic progenitor cells express the Wilms' tumour gene WT1 at levels similar to those in leukaemia cells" British journal of haematology. Feb. 1, 2002;116(2):409-20.
Ibrahiim et al. "Identification of a distinct antibacterial domain within the N-lobe of ovotransferrin" Biochimica et Biophysica Acta (BBA)—Molecular Cell Research. Mar. 5, 1998;1401(3):289-303.
International Search Report for PCT application No. PCT/US2013/021448 dated May 22, 2013.
Kaida et al. "Phase 1 trial of Wilms tumor 1 (WT1) peptide vaccine and gemcitabine combination therapy in patients with advanced pancreatic or biliary tract cancer" Journal of Immunotherapy. Jan. 1, 2011;34(1):92-9.
Keilholz et al. "A clinical and immunologic phase 2 trial ol Wilms tumor aene product 1 (WT1) peptide vaccination in patients with AML and MDS" Blood. Jun. 25, 2009;113(26):6541-8.
Kelly et al, "Lung Cancer—Vaccines" Cancer journal (Sudbury, Mass.). Sep. 2011;17(5):302.
Kessler et al. "Effects of Epitope Modification on T Cell Receptor—Ligand Binding and Antigen Recognition by Seven H-2Kd-restricted Cytotoxic T Lymphocyte Clones Specific for a Photoreactive Peptide Derivative" Journal of Experimental Medicine, Feb. 17, 1997;185(4):629-40.
Kiecker et al. "Analysis of antigen-specific T-cell responses with synthetic peptides—what kind of peptide for which purpose?" Human immunology. May 31, 2004;65(5):523-36.
King et al. "IL15 can reverse the unresponsiveness of Wilms' tumor antigen-specific CTL in patients with prostate cancer" Clinical cancer research. Feb. 15, 2009;15(4):1145-54.
Kobayashi et al. "Defining MHC class II T helper epitopes for WT1 tumor antigen" Cancer Immunology, Immunotherapy. Jul. 1, 2006;55(7):850-60.
Kreidberg et al. "WT-1 is required for early kidney development" Cell. Aug. 27, 1993;74(4):679-91.
Krug et al. "WT1 peptide vaccinations induce CD4 and CD8 T cell immune responses in patients with mesothelioma and non-small cell lung cancer." Cancer immunology, immunotherapy 59.10 (2010): 1467-1479.

(56) References Cited

OTHER PUBLICATIONS

Lapillonne et al. "High WT1 expression after induction therapy predicts high risk of relapse and death in pediatric acute myeloid leukemia" Journal of Clinical Oncology. Apr. 1, 2006;24(10):1507-15.

Lehe et al. "The Wilms' tumor antigen is a novel target for human CD4+ regulatory T cells: implications for immunotherapy" Cancer Research. Aug. 1, 2008;68(15):6350-9.

Maslak et al. "Vaccination with synthetic analog peptides derived from WT1 oncoprotein induces T-cell responses in patients with complete remission from acute myeloid leukemia." Blood 116.2 (2010): 171-179.

May et al. "Peptide epitopes from the Wilms' tumor 1 oncoprotein stimulate CD4+ and CD8+ T cells that recognize and kill human malignant mesothelioma tumor cells" Clinical Cancer Research, Aug. 1, 2007;13(15):4547-55.

McKee et al. "T cell avidity and tumor recognition: implications and therapeutic strategies" Journal of translational medicine. Sep. 20, 2005;3(1):35.

Meister et al. "Two novel T cell epitope prediction, algorithms based on MHC-binding motifs; comparison of predicted and published epitopes from Mycobacterium tuberculosis and HIV protein sequences" Vaccine. Jan. 1, 1995;13(6):581-91.

Menssen et al. "Wilms' tumor gene (WT1) expression in lung cancer, colon cancer and glioblastoma cell lines compared to freshly isolated tumor specimens" Journal of cancer research and clinical oncology. Mar. 4, 2000;126(4)226-32.

Murao et al. "High frequencies of less differentiated and more proliferative WT1-specific CD8+ T cells in bone marrow in tumor-bearing patients: An important role of bone marrow as a secondary lymphoid organ" Cancer science. Apr. 1, 2010;101(4):848-54.

Nicholson et al. "Heteroclitic proliferative responses and changes in cytokine profile induced by altered peptides: implications for autoimmunity". Proceedings of the National Academy of Sciences. Jan. 6, 1998;95(1):264-9.

Nieda et al. "Dendritic cells stimulate the expansion, of bcr-abl specific CD8+ T cells with cytotoxic activity against leukemic cells from patients with chronic myeloid leukemia". Blood, 1998. 91(3): p. 977-83.

Ochsenreither et al. "Wilms' tumor protein 1 (WT1) peptide vaccination in AML patients: predominant TCR CDR3β sequence associated with remission in one patient is detectable in other vaccinated patients" Cancer Immunology, Immunotherapy. Mar. 1, 2012;61(3):313-22.

Ohminami et al. "HLA class I-restricted lysis of leukemia cells by a CD8+ cytotoxic T-lymphocyte clone specific for WT1 peptide" Blood. Jan. 1, 2000;95(1);286-93.

Oka et al. "Human cytotoxic T-lymphocyte responses specific for peptides of the wild-type Wilms' tumor gene (WT1) product" Immunogenetics, Feb. 16, 2000;51(2):99-107.

Oka et al. "Induction of WT1 (Wilms' tumor gene)-specific cytotoxic T lymphocytes by WT1 peptide vaccine and the resultant cancer regression" Proceedings of the National Academy of Sciences of the United States of America. Sep. 21, 2004;101(38);13885-90.

Oka et al. "Cancer immunotherapy targeting Wilms' tumor gene WT1 product" The Journal of Immunology. Feb. 15, 2000;164(4)1873-80.

Parkhurst et al. "Improved induction of melanoma-reactive CTL with peptides from the melanoma antigen gp100 modified at HLA-A* 0201-binding residues" The Journal of Immunology. Sep. 15, 1996;157(6):2539-48.

Parmiani et al. "Cancer immunotherapy with peptide-based vaccines: what have we achieved? Where are we going?" Journal of the National Cancer Institute. Jun. 5, 2002;94(11):805-18.

Pinilla-Ibarz et al, "Improved human T-cell responses against synthetic HLA-0201 analog peptides derived from the WT1 oncoprotein" Leukema. Nov. 1, 2006;20(11):2025-33.

Pinilla-Ibarz et al. "Synthetic peptide analogs derived from bcr/abl fusion proteins and the induction of heteroclitic human T-cell responses" Haernatologica. Jan. 1, 2005;90(10):1324-32.

Pinilla-Ibarz et al. "Vaccination of patients with chronic rnyelogenous leukemia with bcr-abl oncogene breakpoint fusion peptides generates specific immune responses" Blood. Mar. 1, 2000;95(5):1781-7.

Pinilla-Ibarz et al. "Synthetic analogue bcr/abl fusion peptides improve class I immunogenicity to the native protein" InBlood Nov. 16, 2000 (vol. 96, No. 11, pp. 510A-510A).

Pospori et al. "Specificity for the tumor-associated self-antigen WT1 drives the development of fully functional memory T cells in the absence of vaccination" Blood. 2011 Jun 23;117(25):6813-24.

Rammensee eet al. "MHC ligands and peptide motifs: first listing" Immunogenetics. Feb. 1, 1995;41(4):178-228.

Rezvani et al. "Leukemia-associated antigen-specific T-cell responses following combined PR1 and WT1 peptide vaccination in patients with myeloid malignancies" Blood. Jan. 1, 2008;111(1):236-42.

Rezvani et al.Repeated PR1 and WT1 peptide vaccination in Montanide-adjuvant fails to induce sustained high-avidity, epitope-specific CD8+ T cells in myeloid malignancies. Haematologica, Mar. 1, 2011;96(3):432-40.

Rezvani et al. "T-cell responses directed against multiple HLA-A* 0201-restricted epitopes derived from Wilms' tumor 1 protein in patients with leukemia and healthy donors; identification, quantification, and characterization" Clinical Cancer Research. Dec. 15, 2000;11(24):8799-807.

Rosenberg et al. "Immunologic and therapeutic evaluation of a synthetic peptide vaccine for the treatment of patients with metastatic melanoma". Nature medicine. Mar. 1998;4(3):321.

Scardino et al. "HER-2/neu and hTERT cryptic epitopes as novel targets for broad spectrum tumor immunotherapy". The Journal of Immunology. Jun. 1, 2002;168(11):5900-6.

Scharnhorst et al. "WT1 proteins: functions in growth and differentiation" Gene. Aug. 8, 2001;273(2):141-61.

Scheibenbogen et al. "CD8 T-cell responses to Wilms tumor gene product WT1 and proteinase 3 in patients with acute myeloid leukemia" Blood. Sep. 15, 2002;100(6):2132-7.

Slansky et al. "Enhanced antigen-specific antitumor immunity with altered peptide ligands that stabilize the MHC-peptide-TCR complex". Immunity. Oct. 1, 2000;13(4):529-38.

Sloand et al. "T-cell immune responses to Wilms tumor 1 protein in myelodysplasia responsive to immunosuppressive therapy" Blood. Mar. 3, 2011;117(9):2691-9.

Smithgall et al. "Identification of a novel WT1 HLA A* 0201-restricted CTL epitope using whole gene in vitro priming" In Blood Nov. 16, 2001 (vol. 98, No. 11, pp. 121A-121A).

Sugiyama, H. "Wri (Wilms' tumor gene 1): biology and cancer immunotherapy" Japanese journal of clinical oncology. Apr. 15, 2010:hyp194.

Supplementary European Search Report for Europpean Application No. 13736176.2 dated May 2, 2016.

Tamaki et al. "The Wilms' tumor gene WT1 is a good marker for diagnosis of disease progression of myelodyspinstic syndromes" Leukemia. Mar. 1, 1999;13:393-9.

Tatsumi et al, "Wilms' tumor gene WT1-shRNA as a potent apoptosis-inducing agent for solid tumors" International journal of oncology. Mar. 1, 2008;32(3):701-12.

Ten Bosch et al. "A BCR-ABL oncoprotein p210b2a2 fusion region sequence is recognized by HLA-DR2a restricted cytotoxic T lymphocytes and presented by HLA-DR matched cells transfected with an li(b2a2) construct" Blood, 1999. 94(3): p. 1038-45.

The MGC project Team: UniProt Accession Q6PI38; Dec. 14, 2011; [online]; available on the internet: http://www.uniprot.org/uniprot/Q6P138.txt?version=42; downloaded on May 7, 2013.

Tourdot et al. "A general strategy to enhance immunogenicity of low-affinity HLA-A2. 1-associated peptides: implication in the identification of cryptic tumor epitopes" European journal of immunology. Dec. 1, 2000;30(12):3411-21.

Trojan et al. "Generation of cytotoxic T lymphocytes against native and altered peptides of human leukocyte antigen-A* 0201 restricted epitopes from the human epithelial cell adhesion molecule" Cancer research. Jun. 15, 2001;61(12):4761-5.

Tsuboi et al. "Cytotoxic T-lymphocyte responses elicited to Wilms' tumor gene WT1 product by DNA vaccination" Journal of clinical immunology. May 1, 2000;20(3):195-202.

(56) References Cited

OTHER PUBLICATIONS

Tyler et al. "WT1-specific immune responses in patients with high-risk multiple myeloma undergoing allogeneic T cell-depleted hematopoietic stem cell transplantation followed by donor lymphocyte infusions" Blood. Nov. 18, 2011;118(21):1993-.

Valmori et al, "Optimal activation of tumor-reactive T cells by selected antigenic peptide analogues" International immunology. Dec. 1, 1999;11(12):1971-80.

Watson et al. "A prophylactic vaccine for breast cancer?" Breast Cancer Research. Aug. 31, 2010;12(4):310.

Weber et al, "WT1 peptide-specific T cells generated from peripheral blood of healthy donors: possible implications for adoptive immunotherapy after allogeneic stem cell transplantation" Leukemia. Sep. 1, 2009;23(9):1634-42.

Xue et al. "Elimination of human leukemia cells in NOD/SCID mice by WT1-TCR gene-transduced human T cells" Blood. Nov. 1, 2005;106(9):3062-7.

Yang et al. "A tumor suppressor and oncogene: the WT1 story" Leukemia. May 1, 2007;21(5):868-76.

Yotnda, et al. "Cytotoxic T cell response against the chimeric p210 BCR-ABL protein in patients with chronic myelogenous leukemia" Journal of Clinical Investigation. May 15, 1998;101(10):2290.

Yu et al. "Methods for prediction of peptide binding to MHC molecules: a comparative study" Molecular Medicine. Mar. 2002;8(3):137.

Zhang et al. "Advances in dendritic cell-based vaccine of cancer" Cancer Biotherapy and Radiopharmaceuticals. Dec. 1, 2002;17(6):601-19.

Zügel et al. "Termination of peripheral tolerance to a T cell epitope by heteroclitic antigen analogues". The Journal of Immunology. Aug. 15, 1998;161(4)1705-9.

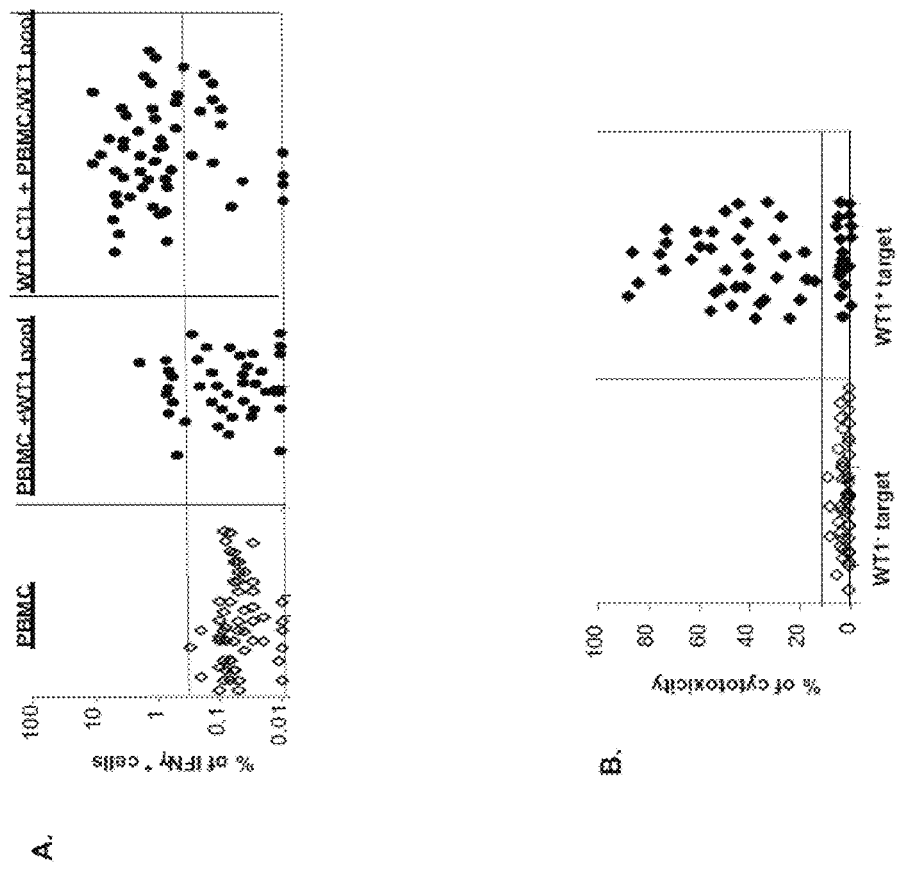
Figure 1 A-B.

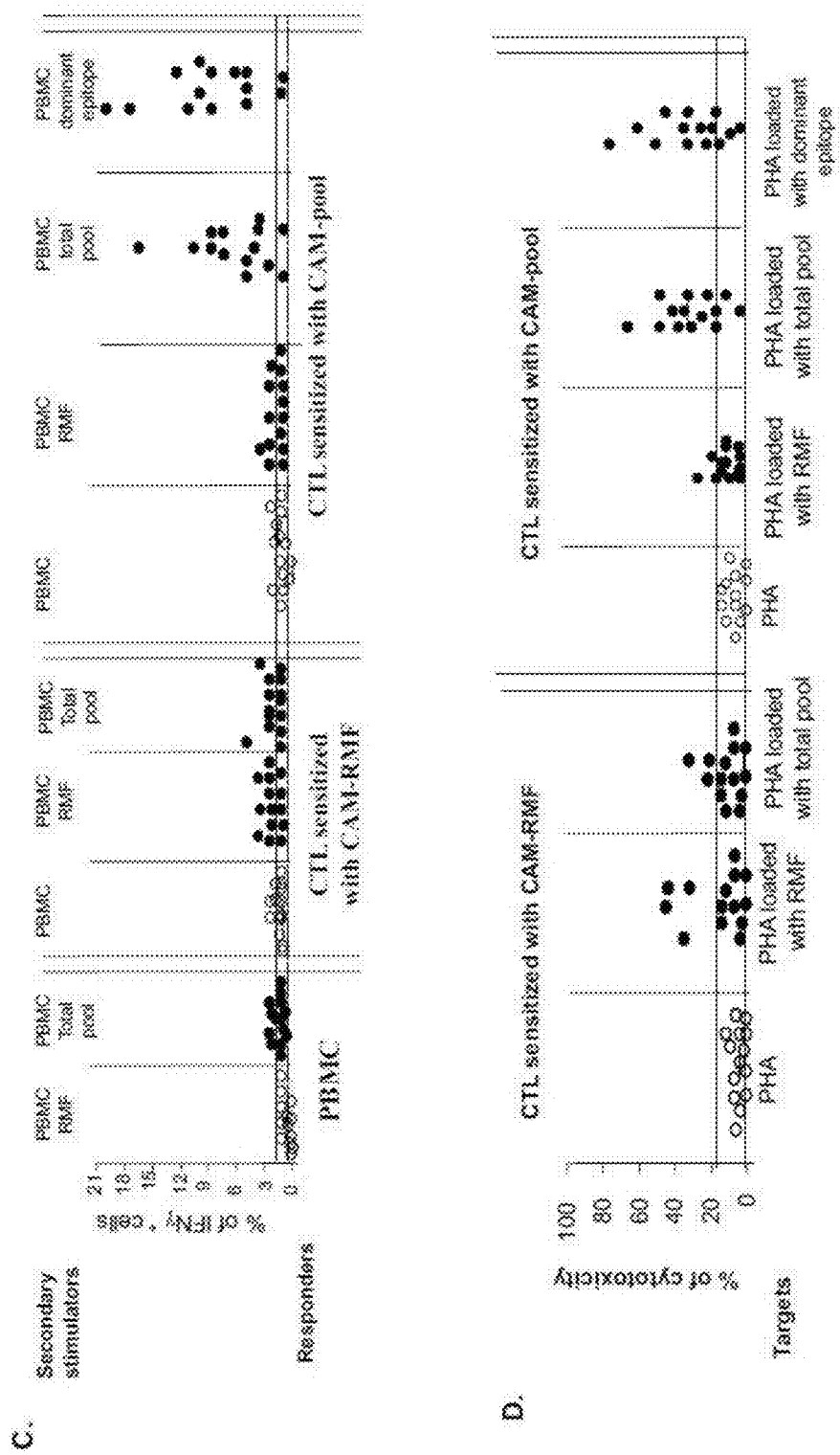
Figure 1 C-D.

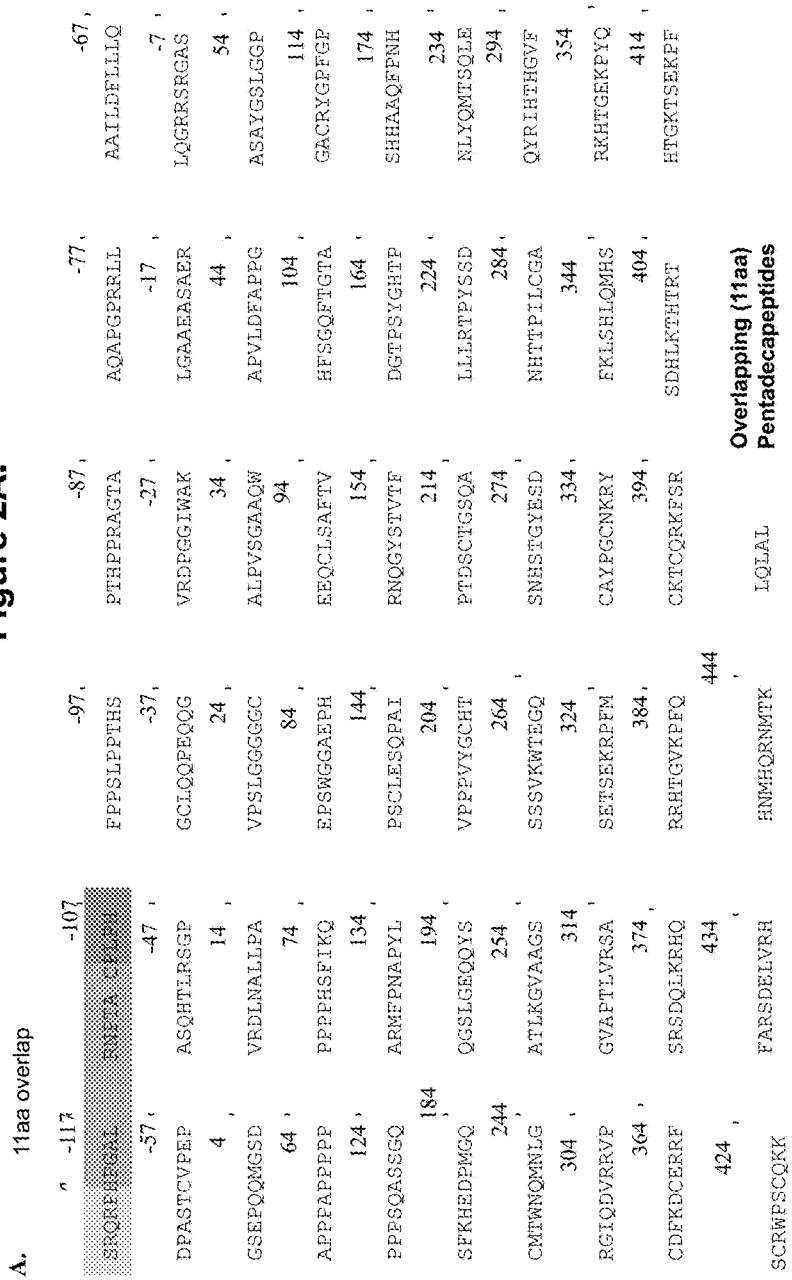

Figure 2B.

| Subpool # \ Subpool # | 1 | 2 | 3 | 4 | 5 | 6 | 7 | 8 | 9 | 10 | 11 | 12 |
|---|---|---|---|---|---|---|---|---|---|---|---|---|
| 13 | 1 | 2 | 3 | 4 | 5 | 6 | 7 | 8 | 9 | 10 | 11 | 12 |
| 14 | 13 | 14 | 15 | 16 | 17 | 18 | 19 | 20 | 21 | 22 | 23 | 24 |
| 15 | 25 | 26 | 27 | 28 | 29 | 30 | 31 | 32 | 33 | 34 | 35 | 36 |
| 16 | 37 | 38 | 39 | 40 | 41 | 42 | 43 | 44 | 45 | 46 | 47 | 48 |
| 17 | 49 | 50 | 51 | 52 | 53 | 54 | 55 | 56 | 57 | 58 | 59 | 60 |
| 18 | 61 | 62 | 63 | 64 | 65 | 66 | 67 | 68 | 69 | 70 | 71 | 72 |
| 19 | 73 | 74 | 75 | 76 | 77 | 78 | 79 | 80 | 81 | 82 | 83 | 84 |
| 20 | 85 | 86 | 87 | 88 | 89 | 90 | 91 | 92 | 93 | 94 | 95 | 96 |
| 21 | 97 | 98 | 99 | 100 | 101 | 102 | 103 | 104 | 105 | 106 | 107 | 108 |
| 22 | 109 | 110 | 111 | 112 | 113 | 114 | 115 | 116 | 117 | 118 | 119 | 120 |
| 23 | 121 | 122 | 123 | 124 | 125 | 126 | 127 | 128 | 129 | 130 | 131 | 132 |
| 24 | 133 | 134 | 135 | 136 | 137 | 138 | 139 | 140 | 141 | | | |

W1 peptide
Subpools 3 and 19 →

Penadecapepide#75
FPNHSFKHEDPMGQQ →

Figure 2 D-E.
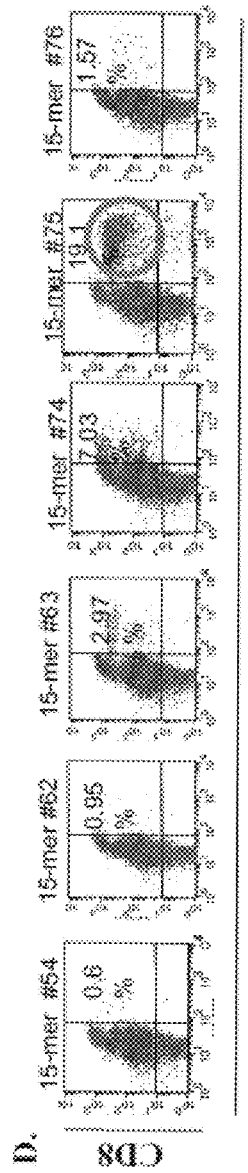
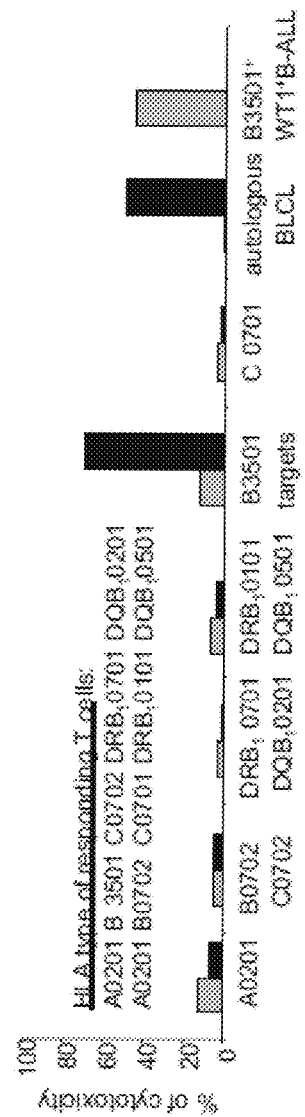

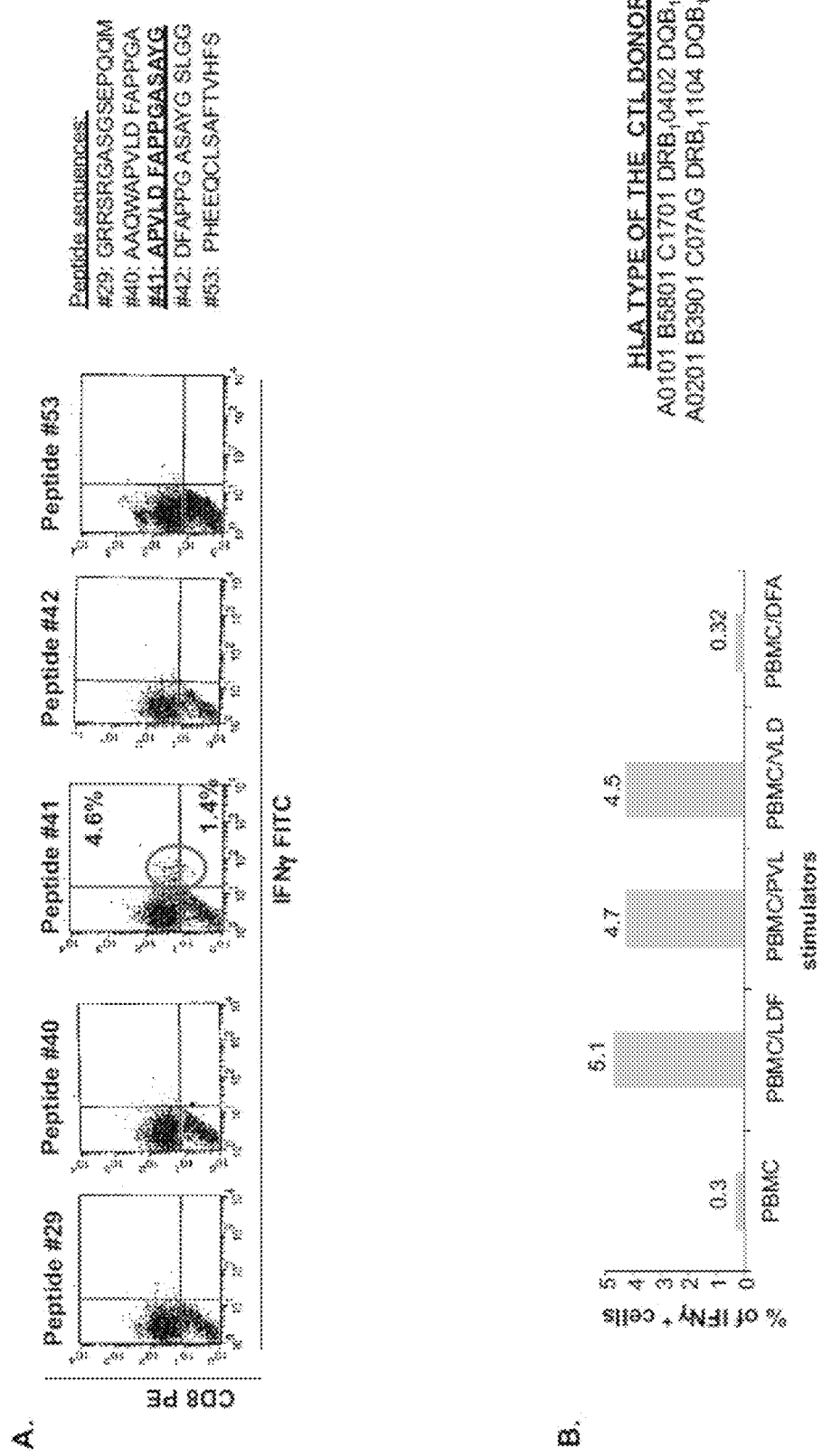

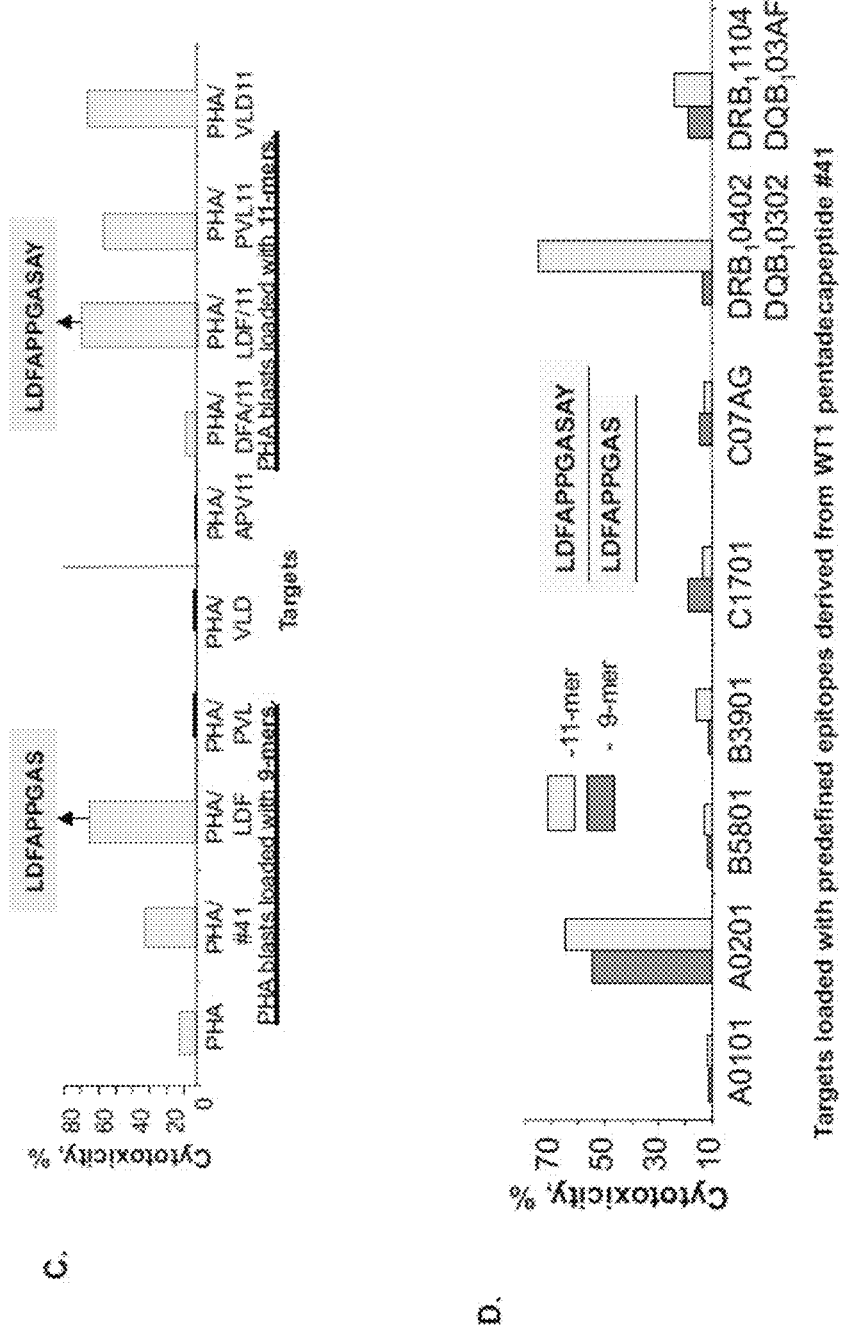
Figure 3 C-D.

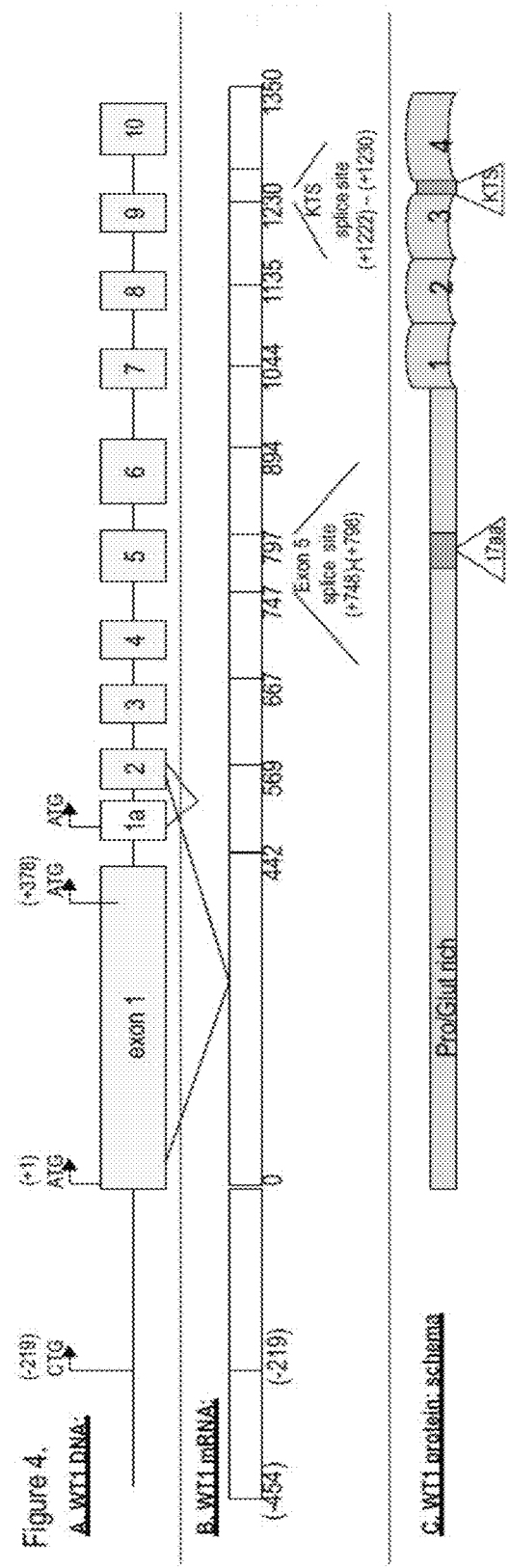
Figure 4 A-C.

Figure 4 D-F.
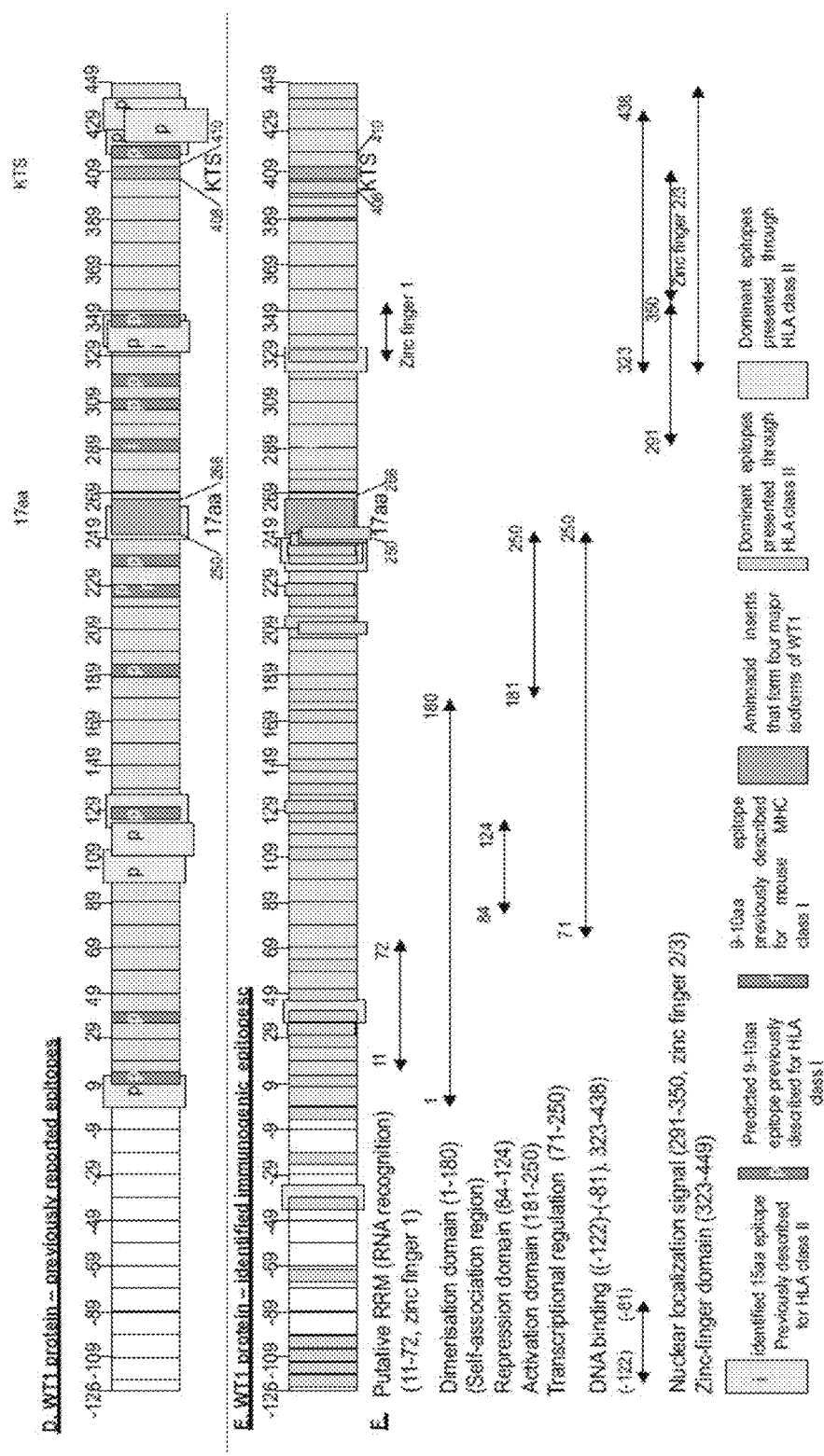

IMMUNOGENIC WT-1 PEPTIDES AND METHODS OF USE THEREOF

This application claims priority to U.S. provisional application Ser. Nos. 61/586,177, filed Jan. 13, 2012; and Ser. No. 61/647,207, filed May 15, 2012; both of which are incorporated herein by reference in their entireties.

GOVERNMENT SUPPORT

This work was supported by grants CA23766, CA59350 and CA08748 from the National Institutes of Health. The US government has certain rights in the invention.

FIELD OF INVENTION

This invention provides peptides, compositions and vaccines comprising same, and methods of treating, reducing the incidence of, and inducing immune responses to a WT1-expressing cancer, comprising administering same.

BACKGROUND OF THE INVENTION

Wilms tumor (WT), a pediatric nephroblastoma that occurs with a frequency of 1 in 10,000 births, has been the subject of intense clinical and basic research for several years. The tumor is embryonic in origin; it is detected in children usually during the first 5 years of life and can occur unilaterally or bilaterally. A WT arises when condensed metanephric mesenchymal cells of the developing kidney fail to properly differentiate. The implication of the Wilms tumor 1 (WT1) tumor suppressor gene in the etiology of WT illustrated the impact that genetic alterations can have on both development and tumorigenesis.

Wilms tumor protein I (WT1) is a zinc finger transcription factor expressed during normal ontogenesis such as in fetal kidney, testis and ovary. In adults, WT1 expression is limited to low levels on hematopoietic stem cells, myoepithelial progenitor cells, renal podocytes and some cells in testis and ovary. Recent demonstration that WT1 is over expressed in several types of leukemia suggested that WT1 would be an attractive target for immunotherapy for various cancers.

SUMMARY OF THE INVENTION

This invention provides peptides, compositions, and immunogenic compositions such as vaccines comprising immunogenic peptides, and methods of treating, reducing the incidence of, and inducing immune responses to a WT1-expressing cancer, comprising administering immunogenic peptides.

In one embodiment, the present invention provides an isolated WT1 peptide having an amino acid (AA) sequence consisting of any one of the sequences SEQ ID NO:1-160, 162-185, 190, 191 and 193. In one embodiment, the present invention provides an isolated HLA class I binding WT1 peptide having an amino acid (AA) sequence consisting of any one of the sequences SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, 183. In one embodiment, the present invention provides an isolated HLA class II binding WT1 peptide having an amino acid (AA) sequence consisting of any one of the sequences SEQ ID NO:149, 156, 173, 174 and 180.

In one embodiment, the present invention provides an isolated WT1 peptide having an amino acid (AA) sequence consisting of any one of the sequences SEQ ID NO: 1-160, 162-185, 190, 191 and 193, or a fragment of any of the foregoing. In one embodiment, the present invention provides an isolated HLA class I binding WT1 peptide having an amino acid (AA) sequence consisting of any one of the sequences SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, 183, 184, 185, 190, 191 and 193. In one embodiment, the present invention provides an isolated HLA class II binding WT1 peptide having an amino acid (AA) sequence consisting of any one of the sequences SEQ ID NO:149, 156, 173, 174 and 180.

In another embodiment, the present invention provides a composition comprising (a) an antigen-presenting cell and (b) a peptide selected from SEQ ID NO:1-160, 162-185, 190, 191 and 193. In another embodiment, the present invention provides a composition comprising (a) an antigen-presenting cell and (b) an HLA class I binding peptide selected from SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, and 183. In another embodiment, the present invention provides a composition comprising (a) an antigen-presenting cell and (b) an HLA class II binding peptide selected from SEQ ID NO:149, 156, 173, 174 and 180.

In another embodiment, the present invention provides a vaccine comprising one or more peptides of SEQ ID NO:1-160, 162-185, 190, 191 and 193. In another embodiment, the present invention provides a vaccine comprising one or more HLA class I binding peptides selected from SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, and 183. In another embodiment, the present invention provides a vaccine comprising one or more HLA class II binding peptides selected from SEQ ID NO:149, 156, 173, 174 and 180. In another embodiment, the present invention provides a vaccine comprising one or more HLA class I binding peptides selected from SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, and 183, and one or more HLA class II binding peptides selected from SEQ ID NO:149, 156, 173, 174 and 180.

In another embodiment, the present invention provides a method of treating a subject with a WT1-expressing cancer, the method comprising administering to the subject a WT1 peptide or vaccine of the present invention, thereby treating a subject with a WT1-expressing cancer.

In another embodiment, the present invention provides a method of reducing the incidence of a WT1-expressing cancer, or its relapse, in a subject, the method comprising administering to the subject a WT1 peptide or vaccine of the present invention, thereby reducing the incidence of a WT1-expressing cancer, or its relapse, in a subject.

In another embodiment, the present invention provides a method of inducing formation and proliferation of a WT1 protein-specific CTL, the method comprising contacting a lymphocyte population with a peptide or composition of the present invention, thereby inducing formation and proliferation of a WT1 protein-specific CTL. This method can be conducted in vitro, ex vivo or in vivo. When conducted in vitro or ex vivo, these CTL can then be infused into a patient for therapeutic effect.

In another embodiment, the present invention provides a method of inducing formation and proliferation of (a) a WT1 protein-specific CD8+ lymphocyte; or (b) a CD4+ lymphocyte specific for the WT1 protein, or the combination thereof, the method comprising contacting a lymphocyte population with a peptide or composition of the present invention, thereby inducing formation and proliferation of (a) a WT1 protein-specific CD8+ lymphocyte; or (b) a CD4+ lymphocyte specific for the WT1 protein; or a combination thereof. This method can be conducted in vitro, ex vivo or in vivo. When conducted in vitro or ex vivo, these CTL can then be infused into a patient for therapeutic effect.

In another embodiment, the present invention provides a method of inducing an anti-cancer immune response in a subject, the method comprising the step of contacting the subject with an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby inducing an anti-mesothelioma immune response in a subject. In one embodiment, the fragment of a WT1 protein consists of a peptide or comprises a peptide from among SEQ ID NO:1-160, 162-185, 190, 191 and 193. In another embodiment the fragment consists of a peptide or comprises a peptide from among SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, and 183, or SEQ ID NO:149, 156, 173, 174 and 180.

In another embodiment, the present invention provides a method of treating a subject with a cancer, the method comprising the step of administering to the subject an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby treating a subject with a mesothelioma. In one embodiment, the fragment of a WT1 protein is a peptide from among SEQ ID NO:1-160, 162-185, 190, 191 or 193. In another embodiment the fragment consists of a peptide or comprises a peptide from among SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, and 183, or SEQ ID NO:149, 156, 173, 174 and 180.

In another embodiment, the present invention provides a method of reducing an incidence of a cancer, or its relapse, in a subject, the method comprising the step of administering to the subject an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby reducing an incidence of a mesothelioma, or its relapse, in a subject. In one embodiment, the fragment of a WT1 protein is a peptide from among SEQ ID NO:1-160, 162-185, 190, 191 or 193. In another embodiment the fragment consists of a peptide or comprises a peptide from among SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, and 183, or SEQ ID NO:149, 156, 173, 174 and 180.

In another embodiment, the cancer is a WT1-expressing cancer. In one embodiment, the WT1-expressing cancer is an acute myelogenous leukemia (AML). In another embodiment, the WT1-expressing cancer is associated with a myelodysplastic syndrome (MDS). In another embodiment, the WT1-expressing cancer is an MDS. In another embodiment, the WT1-expressing cancer is a non-small cell lung cancer (NSCLC). In another embodiment, the WT1-expressing cancer is a Wilms' tumor. In another embodiment, the WT1-expressing cancer is a leukemia. In another embodiment, the WT1-expressing cancer is a hematological cancer. In another embodiment, the WT1-expressing cancer is a lymphoma. In another embodiment, the WT1-expressing cancer is a desmoplastic small round cell tumor. In another embodiment, the WT1-expressing cancer is a mesothelioma. In another embodiment, the WT1-expressing cancer is a malignant mesothelioma. In another embodiment, the WT1-expressing cancer is a gastric cancer. In another embodiment, the WT1-expressing cancer is a colon cancer. In another embodiment, the WT1-expressing cancer is a lung cancer. In another embodiment, the WT1-expressing cancer is a breast cancer. In another embodiment, the WT1-expressing cancer is a germ cell tumor. In another embodiment, the WT1-expressing cancer is an ovarian cancer. In another embodiment, the WT1-expressing cancer is a uterine cancer. In another embodiment, the WT1-expressing cancer is a thyroid cancer. In another embodiment, the WT1-expressing cancer is a hepatocellular carcinoma. In another embodiment, the WT1-expressing cancer is a thyroid cancer. In another embodiment, the WT1-expressing cancer is a liver cancer. In another embodiment, the WT1-expressing cancer is a renal cancer. In another embodiment, the WT1-expressing cancer is a Kaposi's sarcoma. In another embodiment, the WT1-expressing cancer is a sarcoma. In another embodiment, the WT1-expressing cancer is any other carcinoma or sarcoma.

In another embodiment, the WT1-expressing cancer is a solid tumor. In another embodiment, the solid tumor is associated with a WT1-expressing cancer. In another embodiment, the solid tumor is associated with a myelodysplastic syndrome (MDS). In another embodiment, the solid tumor is associated with a non-small cell lung cancer (NSCLC). In another embodiment, the solid tumor is associated with a lung cancer. In another embodiment, the solid tumor is associated with a breast cancer. In another embodiment, the solid tumor is associated with a colorectal cancer. In another embodiment, the solid tumor is associated with a prostate cancer. In another embodiment, the solid tumor is associated with an ovarian cancer. In another embodiment, the solid tumor is associated with a renal cancer. In another embodiment, the solid tumor is associated with a pancreatic cancer. In another embodiment, the solid tumor is associated with a brain cancer. In another embodiment, the solid tumor is associated with a gastrointestinal cancer. In another embodiment, the solid tumor is associated with a skin cancer. In another embodiment, the solid tumor is associated with a melanoma.

In another embodiment, the present invention provides a composition comprising an isolated peptide of the invention in combination with at least 1 additional WT1 peptide. In certain embodiments, a composition comprising at least 2 different isolated peptides of the present invention is provided. In certain embodiments, a composition comprising at least 3 or at least 4 different isolated peptides of the present invention is provided. Each possibility represents a separate embodiment of the present invention. In certain embodiments, the composition of the present invention is a vaccine.

In another embodiment, the present invention provides a method of treating a subject with a WT1-expressing cancer, the method comprising administering to the subject a peptide or composition of the present invention, thereby treating a subject with a WT1-expressing cancer.

In another embodiment, the present invention provides a method of reducing the incidence of a WT1-expressing cancer, or its relapse, in a subject, the method comprising administering to the subject a peptide or composition of the present invention, thereby reducing the incidence of a WT1-expressing cancer, or its relapse, in a subject.

In another embodiment, the present invention provides a method of inducing formation and proliferation of a WT1 protein-specific CTL, the method comprising contacting a lymphocyte population with a peptide or composition of the present invention, thereby inducing formation and proliferation of a WT1 protein-specific CTL.

In another embodiment, the present invention provides a method of inducing formation and proliferation of (a) a WT1 protein-specific CD8$^+$ lymphocyte; or (b) a CD4$^+$ lymphocyte specific for the WT1 protein, or the combination thereof, the method comprising contacting a lymphocyte population with a peptide or composition of the present invention, thereby inducing formation and proliferation of (a) a WT1 protein-specific CD8$^+$ lymphocyte; or (b) a CD4$^+$ lymphocyte specific for the WT1 protein; or a combination thereof.

In another embodiment, the invention is directed to a peptide of the invention with at least one amino acid change that increases the affinity of the peptide for binding to a HLA molecule.

BRIEF DESCRIPTION OF THE FIGURES

So that the matter in which the above-recited features, advantages and objects of the invention, as well as others which will become clear, are attained and can be understood in detail, more particular descriptions of the invention are briefly summarized. Details of the above may be had by reference to certain embodiments thereof, which are illustrated in the appended drawings. These drawings form a part of the specification. It is to be noted; however, that the appended drawings illustrate preferred embodiments of the invention and therefore are not to be considered limiting in their scope.

FIG. 1 A-D shows WT1 specific responses of CTL generated from PBMC of normal donors (n=56) by stimulation with autologous APCs loaded with total pool of WT1 derived pentadecapeptides;

FIG. 3 A-D shows that the combined HLA class I and II restricted WT1 specific T cell response to the same immunodominant peptide sequence derived from WT1 protein in the WT1 CTL after 40 days of co-culture with the WT1 total pool of overlapping 15-mers loaded on autologous CAMs;

FIG. 4A-F depicts schema of WT1; and

DETAILED DESCRIPTION OF THE INVENTION

Figure 2C:
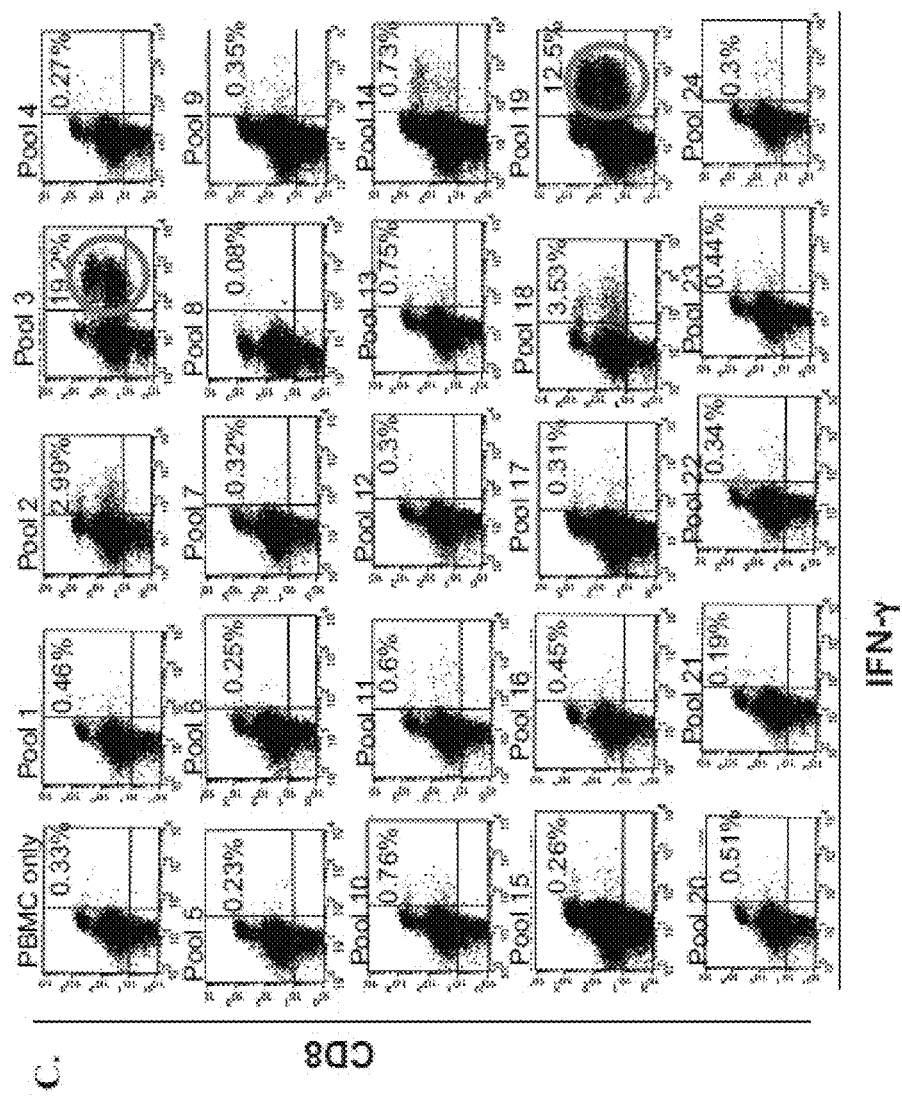
FIG. 2 A-E depicts the strategy for the generation of the total pool of overlapping pentadecapeptides spanning the whole sequence of the WT1 protein and epitope mapping.

This invention provides immunogenic peptides, and compositions and vaccines comprising immunogenic peptides, and methods of treating, reducing the incidence of, and inducing immune responses to a WT1-expressing cancer, comprising administering one or more immunogenic peptides.

This invention provides WT1 peptides and methods of treating, reducing the incidence of, and inducing immune responses against a WT1-expressing cancer, comprising immunogenic peptides.

The WT1 molecule from which the peptides of the present invention are derived has, in another embodiment, the sequence:

```
                                            (SEQ ID NO: 194)
  1  SRQRPHPGAL RNPTACPLPH FPPSLPPTHS PTHPPRAGTA

AQAPGPRRLL

51  AAILDFLLLQ DPASTCVPEP ASQHTLRSGP GCLQQPEQQG

VRDPGGIWAK

101  LGAAEASAER LQGRRSRGAS GSEPQQMGSD VRDLNALLPA

VPSLGGGGGC

151  ALPVSGAAQW APVLDFAPPG ASAYGSLGGP APPPAPPPPP

PPPPHSFIKQ

201  EPSWGGAEPH EEQCLSAFTV HFSGQFTGTA GACRYGPFGP

PPPSQASSGQ

251  ARMFPNAPYL PSCLESQPAI RNQGYSTVTF DGTPSYGHTP

SHHAAQFPNH

301  SFKHEDPMGQ QGSLGEQQYS VPPPVYGCHT PTDSCTGSQA

LLLRTPYSSD

351  NLYQMTSQLE CMTWNQMNLG ATLKGVAAGS SSSVKWTEGQ

SNHSTGYESD

401  NHTTPILCGA QYRIHTHGVF RGIQDVRRVP GVAPTLVRSA

SETSEKRPFM

451  CAYPGCNKRY FKLSHLQMHS RKHTGEKPYQ CDFKDCERRF

SRSDQLKRHQ

501  RRHTGVKPFQ CKTCQRKFSR SDHLKTHTRT HTGKTSEKPF

SCRWPSCQKK

551  FARSDELVRH HNMHQRNMTK LQLAL
```

The foregoing sequence of the WT1 protein is that published by Gessler et al. (37) which comprises 575 aminoacids and includes the first 126 aminoacids in the N-terminus missing in the (Exon 5+, KTS+) isoform of WT116.

In another embodiment, the WT1 sequence is

MGSDVRDLNALLPAVPSLGGGGCALPVSGAAQWAPVLDFAPPGASAYGS

LGGPAPPPAPP

PPPPPPPHSFIKQEPSWGGAEPHEEQCLSAFTVHFSGQFTGTAGACRYGP

FGPPPPSQASSGQA

RMFPNAPYLPSCLESQPAIRNQGYSTVTFDGTPSYGHTPSHHAAQFPNHS

FKHEDPMGQQGS

-continued

LGEQQYSVPPPVYGCHTPTDSCTGSQALLLRTPYSSDNLYQMTSQLECMT

WNQMNLGATLK

GVAAGSSSSVKWTEGQSNHSTGYESDNHTTPILCGAQYRIHTHGVFRGIQ

DVRRVPGVAPTL

VRSASETSEKRPFMCAYPGCNKRYFKLSHLQMHSRKHTGEKPYQCDFKDC

ERRFSRSDQLK

RHQRRHTGVKPFQCKTCQRKFSRSDHLKTHTRTHTGKTSEKPFSCRWPSC

QKKFARSDELVR HHNMHQRNMTKLQLAL (GenBank Accession number AY245105; SEQ ID NO: 195).

In another embodiment, the WT1 molecule has the sequence:

AAEASAERLQGRRSRGASGSEPQQMGSDVRDLNALLPAVPSLGGGGGCAL

PVSGAAQWAP

VLDFAPPGASAYGSLGGPAPPPAPPPPPPPPPHSFIKQEPSWGGAEPHEE

QCLSAFTVHFSGQF

TGTAGACRYGPFGPPPPSQASSGQARMFPNAPYLPSCLESQPAIRNQGYS

TVTFDGTPSYGHT

PSHHAAQFPNHSFKHEDPMGQQGSLGEQQYSVPPPVYGCHTPTDSCTGSQ

ALLLRTPYSSDN

LYQMTSQLECMTWNQMNLGATLKGHSTGYESDNHTTPILCGAQYRIHTHG

VFRGIQDVRRV

PGVAPTLVRSASETSEKRPFMCAYPGCNKRYFKLSHLQMHSRKHTGEKPY

QCDFKDCERRF

SRSDQLKRHQRRHTGVKPFQCKTCQRKFSRSDHLKTHTRTHTGEKPFSCR

WPSCQKKFARS DELVRHHNMHQRNMTKLQLAL (GenBank

Accession number NM_000378; SEQ ID NO: 196).

In another embodiment, the WT1 molecule has the sequence:

MQDPASTCVPEPASQHTLRSGPGCLQQPEQQGVRDPGGIWAKLGAAEASA

ERLQGRRSRGA

SGSEPQQMGSDVRDLNALLPAVPSLGGGGGCALPVSGAAQWAPVLDFAPP

GASAYGSLGGP

APPPAPPPPPPPPPHSFIKQEPSWGGAEPHEEQCLSAFTVHFSGQFTGTA

GACRYGPFGPPPPSQ

ASSGQARMFPNAPYLPSCLESQPAIRNQGYSTVTFDGTPSYGHTPSHHAA

QFPNHSFKHEDP

MGQQGSLGEQQYSVPPPVYGCHTPTDSCTGSQALLLRTPYSSDNLYQMTS

QLECMTWNQM

NLGATLKGVAAGSSSSVKWTEGQSNHSTGYESDNHTTPILCGAQYRIHTH

GVFRGIQDVRRV

PGVAPTLVRSASETSEKRPFMCAYPGCNKRYFKLSHLQMHSRKHTGEKPY

QCDFKDCERRF

SRSDQLKRHQRRHTGVKPFQCKTCQRKFSRSDHLKTHTRTHTGEKPFSCR

WPSCQKKFARS DELVRHHNMHQRNMTKLQLAL (GenBank

Accession number NP_077742; SEQ ID No: 197).

In another embodiment, the WT1 protein has the sequence set forth in GenBank Accession # NM_024426. In other embodiments, the WT1 protein has or comprises one of the sequences set forth in one of the following sequence entries: NM_024425, NM_024424, NM_000378, S95530, D13624, D12496, D 12497, or X77549. In another embodiment, the WT1 protein has any other WT1 sequence known in the art. This invention provides peptides, compositions, and immunogenic compositions such as vaccines comprising immunogenic peptides, and methods of treating, reducing the incidence of, and inducing immune responses to a WT1-expressing cancer, comprising administering immunogenic peptides.

In one embodiment, the present invention provides an isolated WT1 peptide having an amino acid (AA) sequence consisting of any one of the sequences SEQ ID NO:1-160, 162-185, 190, 191 and 193. In one embodiment, the present invention provides an isolated HLA class I binding WT1 peptide having an amino acid (AA) sequence consisting of any one of the sequences SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, and 183. In one embodiment, the present invention provides an isolated HLA class II binding WT1 peptide having an amino acid (AA) sequence consisting of any one of the sequences SEQ ID NO:149, 156, 173, 174 and 180. In another embodiment the HLA class I peptides consist of or comprise SEQ ID NO:142, 143, 144, 145, 146, 147, 148, 150 or 151, and the HLA class II peptide consists of or comprises SEQ ID NO:149.

In one embodiment, the present invention provides an isolated WT1 peptide having an amino acid (AA) sequence comprising any one of the sequences SEQ ID NO:1-53 or 43-XXX, or a fragment thereof. In one embodiment, the present invention provides an isolated HLA class I binding WT1 peptide having an amino acid (AA) sequence comprising of any one of the sequences SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, and 183. In one embodiment, the present invention provides an isolated HLA class II binding WT1 peptide having an amino acid (AA) sequence comprising of any one of the sequences SEQ ID NO:149, 156, 173, 174 and 180. In another embodiment the HLA class I peptides consist of or comprise SEQ ID NO:142, 143, 144, 145, 146, 147, 148, 150 or 151, and the HLA class II peptide consists of or comprises SEQ ID NO:149.

In another embodiment, the present invention provides a composition comprising (a) an antigen-presenting cell and (b) a peptide selected from SEQ ID NO:1-160, 162-185, 190, 191 and 193. In another embodiment, the present invention provides a composition comprising (a) an antigen-presenting cell and (b) an HLA class I binding peptide selected from SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, and 183. In another embodiment, the present invention provides a composition comprising (a) an antigen-presenting cell and (b) an HLA class II binding peptide selected from SEQ ID NO:149, 156, 173, 174 and 180. In another embodiment the HLA class I peptides consist of or comprise SEQ ID NO:142, 143, 144, 145, 146, 147, 148, 150 or 151, and the HLA class II peptide consists of or comprises SEQ ID NO:149.

In another embodiment, the present invention provides a vaccine comprising one or more peptides of SEQ ID NO:1-160, 162-185, 190, 191 and 193. In another embodiment, the present invention provides a vaccine comprising one or more HLA class I binding peptides selected from SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, and 183. In another embodiment, the present invention provides a vaccine comprising one or more HLA class II binding peptides selected from SEQ ID NO:149, 156, 173, 174 and 180. In another embodiment, the present invention provides a vaccine comprising one or more HLA class I binding peptides selected from SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, and 183, and one or more HLA class II binding peptides selected from SEQ ID NO:149, 156, 173, 174 and 180. In another embodiment the HLA class I peptides consist of or comprise SEQ ID NO:142, 143, 144, 145, 146, 147, 148, 150 or 151, and the HLA class II peptide consists of or comprises SEQ ID NO:149.

In another embodiment, the present invention provides a method of treating a subject with a WT1-expressing cancer, the method comprising administering to the subject a WT1 peptide or vaccine of the present invention, thereby treating a subject with a WT1-expressing cancer.

In another embodiment, the present invention provides a method of reducing the incidence of a WT1-expressing cancer, or its relapse, in a subject, the method comprising administering to the subject a WT1 peptide or vaccine of the present invention, thereby reducing the incidence of a WT1-expressing cancer, or its relapse, in a subject.

In another embodiment, the present invention provides a method of inducing an anti-cancer immune response in a subject, the method comprising the step of contacting the subject with an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby inducing an anti-mesothelioma immune response in a subject. In one embodiment, the fragment of a WT1 protein consists of a peptide or comprises a peptide from among SEQ ID NO:1-160, 162-185, 190, 191 and 193. In another embodiment the fragment consists of a peptide or comprises a peptide from among SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, and 183, or SEQ ID NO:149, 156, 173, 174 and 180.

In another embodiment, the present invention provides a method of treating a subject with a cancer, the method comprising the step of administering to the subject an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby treating a subject with a mesothelioma. In one embodiment, the fragment of a WT1 protein is a peptide from among SEQ ID NO:1-160, 162-185, 190, 191 and 193. In another embodiment the fragment consists of a peptide or comprises a peptide from among SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, and 183, or SEQ ID NO:149, 156, 173, 174 and 180. In another embodiment the HLA class I peptides consist of or comprise SEQ ID NO:142, 143, 144, 145, 146, 147, 148, 150 or 151, and the HLA class II peptide consists of or comprises SEQ ID NO:149.

In another embodiment, the present invention provides a method of reducing an incidence of a cancer, or its relapse, in a subject, the method comprising the step of administering to the subject an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby reducing an incidence of a mesothelioma, or its relapse, in a subject. In one embodiment, the fragment of a WT1 protein is a peptide from among SEQ ID NO:1-160, 162-185, 190, 191 or 193. In another embodiment the fragment consists of a peptide or comprises a peptide from among SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, and 183, or SEQ ID NO:149, 156, 173, 174 and 180. In another embodiment the HLA class I peptides consist of or comprise SEQ ID NO:142, 143, 144, 145, 146, 147, 148, 150 or 151, and the HLA class II peptide consists of or comprises SEQ ID NO:149.

In another embodiment, the present invention provides a method of treating a subject with a WT1-expressing cancer, the method comprising administering to the subject a WT1 peptide or vaccine of the present invention, thereby treating a subject with a WT1-expressing cancer.

In another embodiment, the present invention provides a method of reducing the incidence of a WT1-expressing cancer, or its relapse, in a subject, the method comprising administering to the subject a WT1 peptide or vaccine of the present invention, thereby reducing the incidence of a WT1-expressing cancer, or its relapse, in a subject.

In another embodiment, the present invention provides a method of inducing an anti-cancer immune response in a subject, the method comprising the step of contacting the subject with an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby inducing an anti-mesothelioma immune response in a subject. In one embodiment, the fragment of a WT1 protein is a peptide from among SEQ ID NO:1-160, 162-185, 190, 191 or 193. In another embodiment the fragment consists of a peptide or comprises a peptide from among SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, and 183, or SEQ ID NO:149, 156, 173, 174 and 180. In another embodiment the HLA class I peptides consist of or comprise SEQ ID NO:142, 143, 144, 145, 146, 147, 148, 150 or 151, and the HLA class II peptide consists of or comprises SEQ ID NO:149.

In another embodiment, the present invention provides a method of treating a subject with a cancer, the method comprising the step of administering to the subject an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby treating a subject with a mesothelioma. In one embodiment, the fragment of a WT1 protein is a peptide from among SEQ ID NO:1-160, 162-185, 190, 191 or 193.

In another embodiment, the present invention provides a method of reducing an incidence of a cancer, or its relapse, in a subject, the method comprising the step of administering to the subject an immunogenic composition comprising (a) a WT1 protein; (b) a fragment of a WT protein; (c) a nucleotide molecule encoding a WT1 protein; or (d) a nucleotide molecule encoding a fragment of a WT1 protein, thereby reducing an incidence of a mesothelioma, or its relapse, in a subject. In one embodiment, the fragment of a WT1 protein is a peptide from among SEQ ID NO:1-160, 162-185, 190, 191 or 193.

In another embodiment, the cancer is a WT1-expressing cancer. In one embodiment, the WT1-expressing cancer is an acute myelogenous leukemia (AML). In another embodiment, the WT1-expressing cancer is associated with a myelodysplastic syndrome (MDS). In another embodiment, the WT1-expressing cancer is an MDS. In another embodiment, the WT1-expressing cancer is a non-small cell lung cancer (NSCLC). In another embodiment, the WT1-expressing cancer is a Wilms' tumor. In another embodiment, the WT1-expressing cancer is a leukemia. In another embodiment, the WT1-expressing cancer is a hematological cancer. In another embodiment, the WT1-expressing cancer is a lymphoma. In another embodiment, the WT1-expressing cancer is a desmoplastic small round cell tumor. In another embodiment, the WT1-expressing cancer is a mesothelioma. In another embodiment, the WT1-expressing cancer is a malignant mesothelioma. In another embodiment, the WT1-expressing cancer is a gastric cancer. In another embodiment, the WT1-expressing cancer is a colon cancer. In another embodiment, the WT1-expressing cancer is a lung cancer. In another embodiment, the WT1-expressing cancer is a breast cancer. In another embodiment, the WT1-expressing cancer is a germ cell tumor. In another embodiment, the WT1-expressing cancer is an ovarian cancer. In another embodiment, the WT1-expressing cancer is a uterine cancer. In another embodiment, the WT1-expressing cancer is a thyroid cancer. In another embodiment, the WT1-expressing cancer is a hepatocellular carcinoma. In another embodiment, the WT1-expressing cancer is a thyroid cancer. In another embodiment, the WT1-expressing cancer is a liver cancer. In another embodiment, the WT1-expressing cancer is a renal cancer. In another embodiment, the WT1-expressing cancer is a Kaposi's sarcoma. In another embodiment, the WT1-expressing cancer is a sarcoma. In another embodiment, the WT1-expressing cancer is any other carcinoma or sarcoma.

In another embodiment, the WT1-expressing cancer is a solid tumor. In another embodiment, the solid tumor is associated with a WT1-expressing cancer. In another embodiment, the solid tumor is associated with a myelodysplastic syndrome (MDS). In another embodiment, the solid tumor is associated with a non-small cell lung cancer (NSCLC). In another embodiment, the solid tumor is associated with a lung cancer. In another embodiment, the solid tumor is associated with a breast cancer. In another embodiment, the solid tumor is associated with a colorectal cancer. In another embodiment, the solid tumor is associated with a prostate cancer. In another embodiment, the solid tumor is associated with an ovarian cancer. In another embodiment, the solid tumor is associated with a renal cancer. In another embodiment, the solid tumor is associated with a pancreatic cancer. In another embodiment, the solid tumor is associated with a brain cancer. In another embodiment, the solid tumor is associated with a gastrointestinal cancer. In another embodiment, the solid tumor is associated with a skin cancer. In another embodiment, the solid tumor is associated with a melanoma.

In another embodiment, the present invention provides a composition comprising an isolated peptide of the invention in combination with at least 1 additional WT1 peptide. In certain embodiments, a composition comprising at least 2 different isolated peptides of the present invention is provided. In certain embodiments, a composition comprising at least 3 or at least 4 different isolated peptides of the present invention is provided. Each possibility represents a separate embodiment of the present invention. In certain embodiments, the composition of the present invention is a vaccine.

In another embodiment, the present invention provides a method of treating a subject with a WT1-expressing cancer, the method comprising administering to the subject a peptide or composition of the present invention, thereby treating a subject with a WT1-expressing cancer.

In another embodiment, the present invention provides a method of reducing the incidence of a WT1-expressing cancer, or its relapse, in a subject, the method comprising administering to the subject a peptide or composition of the present invention, thereby reducing the incidence of a WT1-expressing cancer, or its relapse, in a subject.

In another embodiment, the present invention provides a method of inducing formation and proliferation of a WT1 protein-specific CTL, the method comprising contacting a lymphocyte population with a peptide or composition of the present invention, thereby inducing formation and proliferation of a WT1 protein-specific CTL.

In another embodiment, the present invention provides a method of inducing formation and proliferation of (a) a WT1 protein-specific $CD8^+$ lymphocyte; or (b) a $CD4^+$ lymphocyte specific for the WT1 protein, or the combination thereof, the method comprising contacting a lymphocyte population with a peptide or composition of the present invention, thereby inducing formation and proliferation of (a) a WT1 protein-specific $CD8^+$ lymphocyte; or (b) a $CD4^+$ lymphocyte specific for the WT1 protein; or a combination thereof.

In another embodiment, the invention is directed to a peptide of the invention with at least one amino acid change that increases the affinity of the peptide for binding to a HLA molecule.

"Peptide," in another embodiment of methods and compositions of the present invention, refers to a compound of subunit AA connected by peptide bonds. In another embodiment, the peptide comprises an AA analogue. In another embodiment, the peptide comprises a peptidomimetic. The different AA analogues and peptidomimetics that can be included in the peptides of methods and compositions of the present invention are enumerated herein below. The subunits are, in another embodiment, linked by peptide bonds. In another embodiment, the subunit is linked by another type of bond, e.g. ester, ether, etc. Each possibility represents a separate embodiment of the present invention.

The unaltered peptides of the present invention (as described both above and below) are referred to collectively herein as "WT1 peptides." Each of the embodiments enumerated below for "WT1 peptides" applies to unaltered WT1 peptides and HLA class I and class II heteroclitic peptides of the present invention. Each possibility represents a separate embodiment of the present invention.

In another embodiment, a WT1 peptide of the present invention binds to an HLA class I molecule or a class II molecule. In another embodiment the peptide binds to both a class I and a class II molecule. In another embodiment, the HLA class II molecule is an HLA-DRB molecule. In another embodiment, the HLA class Il-molecule is an HLA-DRA molecule. In another embodiment, the HLA molecule is an HLA-DQA1 molecule. In another embodiment, the HLA molecule is an HLA-DQB1 molecule. In another embodiment, the HLA molecule is an HLA-DPA1 molecule. In another embodiment, the HLA molecule is an HLA-DPB 1 molecule. In another embodiment, the HLA molecule is an HLA-DMA molecule. In another embodiment, the HLA molecule is an HLA-DMB molecule. In another embodiment, the HLA molecule is an HLA-DOA molecule. In another embodiment, the HLA molecule is an HLA-DOB molecule. In another embodiment, the HLA molecule is any other HLA class Il-molecule known in the art. Each possibility represents a separate embodiment of the present invention.

In another embodiment, the HLA class I molecule whose binding motif is contained in or comprising a peptide of the present invention is, in another embodiment, an HLA-A molecule. In another embodiment, the HLA class I molecule is an HLA-B molecule. In another embodiment, the HLA class I molecule is an HLA-C molecule. In another embodiment, the HLA class I molecule is an HLA-A0201 molecule. In another embodiment, the molecule is HLA A1. In another embodiment, the HLA class I molecule is HLA A2. In another embodiment, the HLA class I molecule is HLA A2.1. In another embodiment, the HLA class I molecule is HLA A3. In another embodiment, the HLA class I molecule is HLA A3.2. In another embodiment, the HLA class I molecule is HLA A11. In another embodiment, the HLA class I molecule is HLA A24. In another embodiment, the HLA class I molecule is HLA B7. In another embodiment, the HLA class I molecule is HLA B27. In another embodiment, the HLA class I molecule is HLA B8. Each possibility represents a separate embodiment of the present invention.

In another embodiment, the HLA class I molecule-binding WT1 peptide of methods and compositions of the present invention binds to a superfamily of HLA class I molecules. In another embodiment, the superfamily is the A2 superfamily. In another embodiment, the superfamily is the A3 superfamily. In another embodiment, the superfamily is the A24 superfamily. In another embodiment, the superfamily is the B7 superfamily. In another embodiment, the superfamily is the B27 superfamily. In another embodiment, the superfamily is the B44 superfamily. In another embodiment, the superfamily is the C1 superfamily. In another embodiment, the superfamily is the C4 superfamily. In another embodiment, the superfamily is any other superfamily known in the art. Each possibility represents a separate embodiment of the present invention.

In another embodiment, the HLA molecule is a A0101, A0201, A0203, A2402, A6901, B0702, A3101, B3501, B3503, B3508, B3802, B3801, B3901, B4001, B4402, B4701, B5701, C0401, C1701, DRB$_1$0101, DRB$_1$0402, DRB$_1$0402, DRB$_1$0401 or DRB$_1$1104 molecule. In another embodiment, the peptides of SEQ ID NO:142, 143, 144, 145, 146, 147, 148, 149, 150, 151, 152, 153, 154, 155, 156, 157, 158, 159, 160, 162, 163, 164, 165, 166, 167, 168, 169, 170, 171, 173, 174, 175, 176, 177, 178, 179, 180, 181, 182, and 183, and SEQ ID NO:149, 156, 173, 174 and 180, bind to the HLA class I or class II molecules described for each peptide in Tables 1 or 2. In another embodiment the HLA class I peptides consist of or comprise SEQ ID NO:142, 143, 144, 145, 146, 147, 148, 150 or 151, and the HLA class II peptide consists of or comprises SEQ ID NO:149, and bind to the corresponding HLA molecule or molecules indicated for each peptide in Table 1 or Table 2. In one embodiment, certain peptides can bind to more than one HLA allele.

In another embodiment, a modification of a peptide of the invention is provided. In one embodiment the modification comprises at least one heteroclitic amino acid change, also referred to as a mutation or mutated, or an anchor residue mutation (see below). An HLA class I molecule binding motif of a modified peptide of the present invention exhibits an increased affinity for the HLA class I molecule, relative to the unmutated counterpart of the peptide. In another embodiment, the point mutation increases the affinity of the isolated, mutated WT1 peptide for the HLA class I molecule. In another embodiment, the increase in affinity is relative to the affinity (for the same HLA class I molecule) of the isolated, unmutated WT1 peptide wherefrom the isolated, mutated WT1 peptide was derived. Each possibility represents a separate embodiment of the present invention.

In another embodiment, a WT1 peptide of methods and compositions of the present invention is so designed as to exhibit affinity for an HLA molecule. In another embodiment, the affinity is a high affinity, as described herein.

HLA molecules, known in another embodiment as major histocompatibility complex (MHC) molecules, bind peptides and present them to immune cells. Thus, in another embodiment, the immunogenicity of a peptide is partially determined by its affinity for HLA molecules. HLA class I molecules interact with CD8 molecules, which are generally present on cytotoxic T lymphocytes (CTL). HLA class II molecules interact with CD4 molecules, which are generally present on helper T lymphocytes.

In another embodiment, a peptide of the present invention is immunogenic. In another embodiment, "immunogenic" refers to an ability to stimulate, elicit or participate in an immune response. In another embodiment, the immune response elicited is a cell-mediated immune response. In another embodiment, the immune response is a combination of cell-mediated and humoral responses.

In another embodiment, T cells that bind to the MHC molecule-peptide complex become activated and induced to proliferate and lyse cells expressing a protein comprising the peptide. T cells are typically initially activated by "professional" antigen presenting cells ("APC"; e.g. dendritic cells, monocytes, and macrophages), which present costimulatory molecules that encourage T cell activation as opposed to anergy or apoptosis. In another embodiment, the response is heteroclitic, as described herein, such that the CTL lyses a neoplastic cell expressing a protein which has an AA sequence homologous to a peptide of this invention, or a different peptide than that used to first stimulate the T cell.

In another embodiment, an encounter of a T cell with a peptide of this invention induces its differentiation into an effector and/or memory T cell. Subsequent encounters between the effector or memory T cell and the same peptide, or, in another embodiment, with a related peptide of this invention, leads to a faster and more intense immune response. Such responses are gauged, in another embodiment, by measuring the degree of proliferation of the T cell population exposed to the peptide. In another embodiment, such responses are gauged by any of the methods enumerated herein below.

In another embodiment, the peptides of methods and compositions of the present invention bind an HLA class II molecule with high affinity. In other embodiments, the HLA class II molecule is any HLA class II molecule enumerated herein. Each possibility represents a separate embodiment of the present invention.

In another embodiment, derivatives of peptides of methods and compositions of the present invention bind an HLA class I molecule with high affinity. In other embodiments, the MHC class I molecule is any MHC class I molecule enumerated herein. Each possibility represents a separate embodiment of the present invention.

In another embodiment, a peptide of methods and compositions of the present invention binds an HLA class II molecule with significant affinity, while a peptide derived from the original peptide binds an HLA class I molecule with significant affinity.

In another embodiment, "affinity" refers to the concentration of peptide necessary for inhibiting binding of a standard peptide to the indicated MHC molecule by 50%. In another embodiment, "high affinity" refers to an affinity is such that a concentration of about 500 nanomolar (nM) or less of the peptide is required for 50% inhibition of binding of a standard peptide. In another embodiment, a concentration of about 400 nM or less of the peptide is required. In another embodiment, the binding affinity is 300 nM. In another embodiment, the binding affinity is 200 nM. In another embodiment, the binding affinity is 150 nM. In another embodiment, the binding affinity is 100 nM. In another embodiment, the binding affinity is 80 nM. In another embodiment, the binding affinity is 60 nM. In another embodiment, the binding affinity is 40 nM. In another embodiment, the binding affinity is 30 nM. In another embodiment, the binding affinity is 20 nM. In another embodiment, the binding affinity is 15 nM. In another embodiment, the binding affinity is 10 nM. In another embodiment, the binding affinity is 8 nM. In another embodiment, the binding affinity is 6 nM. In another embodiment, the binding affinity is 4 nM. In another embodiment, the binding affinity is 3 nM. In another embodiment, the binding affinity is 2 nM. In another embodiment, the binding affinity is 1.5 nM. In another embodiment, the binding affinity is 1 nM. In another embodiment, the binding affinity is 0.8 nM. In another embodiment, the binding affinity is 0.6 nM. In another embodiment, the binding affinity is 0.5 nM. In another embodiment, the binding affinity is 0.4 nM. In another embodiment, the binding affinity is 0.3 nM. In another embodiment, the binding affinity is less than 0.3 nM.

In another embodiment, "affinity" refers to a measure of binding strength to the MHC molecule. In another embodiment, affinity is measured using a method known in the art to measure competitive binding affinities. In another embodiment, affinity is measured using a method known in the art to measure relative binding affinities. In another embodiment, the method is a competitive binding assay. In another embodiment, the method is radioimmunoassay or RIA. In another embodiment, the method is BiaCore analyses. In another embodiment, the method is any other method known in the art. In another embodiment, the method yields an IC50 in relation to an IC50 of a reference peptide of known affinity.

Each type of affinity and method of measuring affinity represents a separate embodiment of the present invention.

In another embodiment, "high affinity" refers to an IC50 of 0.5-500 nM. In another embodiment, the IC50 is 1-300 nM. In another embodiment, the IC50 is 1.5-200 nM. In another embodiment, the IC50 is 2-100 nM. In another embodiment, the IC50 is 3-100 nM. In another embodiment, the IC50 is 4-100 nM. In another embodiment, the IC50 is 6-100 nM. In another embodiment, the IC50 is 10-100 nM. In another embodiment, the IC50 is 30-100 nM. In another embodiment, the IC50 is 3-80 nM. In another embodiment, the IC50 is 4-60 nM. In another embodiment, the IC50 is 5-50 nM. In another embodiment, the IC50 is 6-50 nM. In another embodiment, the IC50 is 8-50 nM. In another embodiment, the IC50 is 10-50 nM. In another embodiment, the IC50 is 20-50 nM. In another embodiment, the IC50 is 6-40 nM. In another embodiment, the IC50 is 8-30 nM. In another embodiment, the IC50 is 10-25 nM. In another embodiment, the IC50 is 15-25 nM. Each affinity and range of affinities represents a separate embodiment of the present invention.

In another embodiment, a peptide of methods and compositions of the present invention binds to a superfamily of HLA molecules. Superfamilies of HLA molecules share very similar or identical binding motifs. In another embodiment, the superfamily is a HLA class I superfamily. In another embodiment, the superfamily is a HLA class II superfamily. Each possibility represents a separate embodiment of the present invention.

The terms "HLA-binding peptide," "HLA class I molecule-binding peptide," and "HLA class II molecule-binding peptide" refer, in another embodiment, to a peptide that binds an HLA molecule with measurable affinity. In another embodiment, the terms refer to a peptide that binds an HLA molecule with high affinity. In another embodiment, the terms refer to a peptide that binds an HLA molecule with sufficient affinity to activate a T cell precursor. In another embodiment, the terms refer to a peptide that binds an HLA molecule with sufficient affinity to mediate recognition by a T cell. The HLA molecule is, in other embodiments, any of the HLA molecules enumerated herein. Each possibility represents a separate embodiment of the present invention.

"Heteroclitic" refers, in another embodiment, to a peptide that generates an immune response that recognizes the original peptide from which the heteroclitic peptide was derived (e.g. the peptide not containing the anchor residue mutations). In another embodiment, "original peptide" refers to a peptide of the present invention. In another embodiment, "heteroclitic" refers to a peptide that generates an immune response that recognizes the original peptide from which the heteroclitic peptide was derived, wherein the immune response generated by vaccination with the heteroclitic peptide is greater than the immune response generated by vaccination with the original peptide. In another embodiment, a "heteroclitic" immune response refers to an immune response that recognizes the original peptide from which the improved peptide was derived (e.g. the peptide not containing the anchor residue mutations). In another embodiment, a "heteroclitic" immune response refers to an immune response that recognizes the original peptide from which the heteroclitic peptide was derived, wherein the magnitude of the immune response generated by vaccination with the heteroclitic peptide is greater than the immune response generated by vaccination with the original peptide. In another embodiment, the magnitude of the immune response generated by vaccination with the heteroclitic peptide is greater than the immune response substantially equal to the response to vaccination with the original peptide. In another embodiment, the magnitude of the immune response generated by vaccination with the heteroclitic peptide is greater than the immune response less than the response to vaccination with the original peptide. In another embodiment, a heteroclitic peptide of the present invention is an HLA class I heteroclitic peptide. Methods for identifying HLA class I and class II residues, and for improving HLA binding by mutating the residues, are well known in the art, as described below. Each possibility represents a separate embodiment of the present invention.

In another embodiment, a heteroclitic peptide of the present invention induces an immune response that is increased at least 2-fold relative to the WT1 peptide from which the heteroclitic peptide was derived ("native peptide"). In another embodiment, the increase is 3-fold relative to the native peptide. In another embodiment, the increase is 5-fold relative to the native peptide. In another embodiment, the increase is 7-fold relative to the native peptide. In another embodiment, the increase is 10-fold relative to the native peptide. In another embodiment, the increase is 15-fold relative to the native peptide. In another embodiment, the increase is 20-fold relative to the native peptide. In another embodiment, the increase is 30-fold relative to the native peptide. In another embodiment, the increase is 50-fold relative to the native peptide. In another embodiment, the increase is 100-fold relative to the native peptide. In another embodiment, the increase is 150-fold relative to the native peptide. In another embodiment, the increase is 200-fold relative to the native peptide. In another embodiment, the increase is 300-fold relative to the native peptide. In another embodiment, the increase is 500-fold relative to the native peptide. In another embodiment, the increase is 1000-fold relative to the native peptide. In another embodiment, the increase is more than 1000-fold relative to the native peptide. Each possibility represents a separate embodiment of the present invention.

In another embodiment, the present invention provides a HLA class II heteroclitic peptide derived from an isolated WT1 peptide of the present invention. In another embodiment, the process of deriving comprises introducing a mutation that enhances a binding of the peptide to an HLA class II molecule. In another embodiment, the process of deriving consists of introducing a mutation that enhances a binding of the peptide to an HLA class I molecule. In another embodiment, the mutation is in an HLA class II anchor residue. In another embodiment, a heteroclitic class II peptide of the present invention is identified and tested in a manner analogous to identification and testing of HLA class I heteroclitic peptides, as exemplified herein. Each possibility represents a separate embodiment of the present invention.

In another embodiment, the HLA class II binding site in a peptide of the present invention is created or improved by mutation of an HLA class II motif anchor residue. In another embodiment, the anchor residue that is modified is in the P1 position. In another embodiment, the anchor residue is at the P2 position. In another embodiment, the anchor residue is at the P6 position. In another embodiment, the anchor residue is at the P9 position. In another embodiment, the anchor residue is selected from the P1, P2, P6, and P9 positions. In another embodiment, the anchor residue is at the P3 position. In another embodiment, the anchor residue is at the P4 position. In another embodiment, the anchor residue is at the P5 position. In another embodiment, the anchor residue is at the P6 position. In another embodiment, the anchor residue is at the P8 position. In another embodiment, the anchor residue is at the P10 position. In another embodiment, the anchor residue is at the P11 position. In another embodiment, the anchor residue is at the P12 position. In another embodiment, the anchor residue is at the P13 position. In another embodiment, the anchor residue is at any other anchor residue of an HLA class II molecule that is known in the art. In another embodiment, residues other than P1, P2, P6, and P9 serve as secondary anchor residues; therefore, mutating them can improve HLA class II binding. Each possibility represents a separate embodiment of the present invention.

In another embodiment, a heteroclitic peptide is generated by introduction of a mutation that creates an anchor motif. "Anchor motifs" or "anchor residues" refers, in another embodiment, to 1 or a set of preferred residues at particular positions in an HLA-binding sequence.

HLA-binding sequence is an HLA class II-binding sequence. In another embodiment, the HLA-binding sequence is an HLA class I-binding sequence. In another embodiment, the positions corresponding to the anchor motifs are those that play a significant role in binding the HLA molecule. In another embodiment, the anchor residue is a primary anchor motif. In another embodiment, the anchor residue is a secondary anchor motif. Each possibility represents a separate embodiment of the present invention.

Methods for predicting MHC class II epitopes are well known in the art. In another embodiment, the MHC class II epitope is predicted using TEPITOPE (Meister G E, Roberts C G et al, Vaccine 1995 13: 581-91). In another embodiment, the MHC class II epitope is predicted using EpiMatrix (De Groot A S, Jesdale B M et al, AIDS Res Hum Retroviruses 1997 13: 529-31). In another embodiment, the MHC class II epitope is predicted using the Predict Method (Yu K, Petrovsky N et al, Mol Med. 2002 8: 137-48). In another embodiment, the MHC class II epitope is predicted using the SYFPEITHI epitope prediction algorithm (Examples). In another embodiment, the MHC class II epitope is predicted using Rankpep. In another embodiment, the MHC class II epitope is predicted using any other method known in the art. Each possibility represents a separate embodiment of the present invention.

In another embodiment, in the case of HLA class II-binding peptides (e.g. HLA-DR-binding peptides), the anchor residue that is modified is in the P1 position. In another embodiment, the anchor residue is in the P2 position. In another embodiment, the anchor residue is in the P6 position. In another embodiment, the anchor residue is in the P9 position. In other embodiments, the anchor residue is the P3, P4, P5, P6, P8, P10, P11, P12, or P13 position. In another embodiment, the anchor residue is any other anchor residue of an HLA class II molecule that is known in the art. In another embodiment, residues other than P1, P2, P6, and P9 serve as secondary anchor residues; therefore, mutating them can improve HLA class II binding. In another embodiment, any combination of the above residues is mutated. Each possibility represents a separate embodiment of the present invention.

In another embodiment, a WT1 peptide of the present invention binds to 2 distinct HLA class II molecules. In another embodiment, the peptide binds to three distinct HLA class II molecules. In another embodiment, the peptide binds to four distinct HLA class II molecules. In another embodiment, the peptide binds to five distinct HLA class II molecules. In another embodiment, the peptide binds to six distinct HLA class II molecules. In another embodiment, the peptide binds to more than six distinct HLA class II molecules.

In another embodiment, the HLA class II molecules that are bound by a WT1 peptide of the present invention are encoded by two or more distinct alleles at a given HLA class II locus. In another embodiment, the HLA class II molecules are encoded by 3 distinct alleles at a locus. In another embodiment, the HLA class II molecules are encoded by 4 distinct alleles at a locus. In another embodiment, the HLA class II molecules are encoded by 5 distinct alleles at a locus.

In another embodiment, the HLA class II molecules are encoded by 6 distinct alleles at a locus. In another embodiment, the HLA class II molecules are encoded by more than six distinct alleles at a locus.

In another embodiment, the HLA class II molecules bound by the WT1 peptide are encoded by HLA class II genes at 2 distinct loci. In another embodiment, the HLA molecules bound are encoded by HLA class II genes at 2 or more distinct loci. In another embodiment, the HLA molecules bound are encoded by HLA class II genes at 3 distinct loci. In another embodiment, the HLA molecules bound are encoded by HLA class II genes at 3 or more distinct loci. In another embodiment, the HLA molecules bound are encoded by HLA class II genes at 4 distinct loci. In another embodiment, the HLA molecules bound are encoded by HLA class II genes at 4 or more distinct loci. In another embodiment, the HLA molecules bound are encoded by HLA class II genes at more than 4 distinct loci. In other embodiments, the loci are selected from HLA-DRB loci. In another embodiment, the HLA class II-binding peptide is an HLA-DRA binding peptide. In another embodiment, the peptide is an HLA-DQA1 binding peptide. In another embodiment, the peptide is an HLA-DQB 1 binding peptide. In another embodiment, the peptide is an HLA-DPA1 binding peptide. In another embodiment, the peptide is an HLA-DPB 1 binding peptide. In another embodiment, the peptide is an HLA-DMA binding peptide. In another embodiment, the peptide is an HLA-DMB binding peptide. In another embodiment, the peptide is an HLA-DOA binding peptide. In another embodiment, the peptide is an HLA-DOB binding peptide. In another embodiment, the peptide binds to any other HLA class II molecule known in the art. Each possibility represents a separate embodiment of the present invention.

In another embodiment, a WT1 peptide of the present invention binds to 2 distinct HLA-DRB molecules. In another embodiment, the peptide binds to 3 distinct HLA-DRB molecules. In another embodiment, the peptide binds to 4 distinct HLA-DRB molecules. In another embodiment, the peptide binds to 5 distinct HLA-DRB molecules. In another embodiment, the peptide binds to 6 distinct HLA-DRB molecules. In another embodiment, the peptide binds to more than 6 distinct HLA-DRB molecules.

In another embodiment, a WT1 peptide of the present invention binds to HLA-DRB molecules that are encoded by 2 distinct HLA-DRB alleles. In another embodiment, the HLA-DRB molecules are encoded by 3 distinct HLA-DRB alleles. In another embodiment, the HLA-DRB molecules are encoded by 4 distinct HLA-DRB alleles. In another embodiment, the HLA-DRB molecules are encoded by 5 distinct HLA-DRB alleles. In another embodiment, the HLA-DRB molecules are encoded by 6 distinct HLA-DRB alleles. In another embodiment, the HLA-DRB molecules are encoded by more than 6 distinct HLA-DRB alleles. Each possibility represents a separate embodiment of the present invention.

In another embodiment, a WT1 peptide of the present invention binds to HLA-DRB molecules that are encoded by 2 distinct HLA-DRB alleles selected from DRB 101, DRB 301, DRB 401, DRB 701, DRB 1101, and DRB 1501. In another embodiment, the WT1 peptide binds to HLA-DRB molecules encoded by 3 distinct HLA-DRB alleles selected from DRB 101, DRB 301, DRB 401, DRB 701, DRB 1101, and DRB 1501. In another embodiment, the WT1 peptide binds to HLA-DRB molecules encoded by 4 distinct HLA-DRB alleles selected from DRB 101, DRB 301, DRB 401, DRB 701, DRB 1101, and DRB 1501. In another embodiment, the WT1 peptide binds to HLA-DRB molecules encoded by 5 distinct HLA-DRB alleles selected from DRB 101, DRB 301, DRB 401, DRB 701, DRB 1101, and DRB 1501. In another embodiment, the WT1 peptide binds to HLA-DRB molecules encoded by each of the following HLA-DRB alleles: DRB 101, DRB 301, DRB 401, DRB 701, DRB 1101, and DRB 1501. Each possibility represents a separate embodiment of the present invention.

In another embodiment, the present invention provides a composition comprising 2 distinct WT1 peptides of the present invention. In another embodiment, the 2 distinct WT1 peptides are both unaltered. In another embodiment, 1 of the WT1 peptides is unaltered, while the other is heteroclitic. In another embodiment, both of the WT1 peptides are heteroclitic.

In another embodiment, the composition comprises 3 distinct WT1 peptides of the present invention. In another embodiment, the composition comprises 4 distinct WT1 peptides of the present invention. In another embodiment, the composition comprises 5 distinct WT1 peptides of the present invention. In another embodiment, the composition comprises more than 5 distinct isolated WT1 peptides of the present invention.

In another embodiment, 2 of the WT1 peptides in the composition are unaltered. In another embodiment, 2 of the WT1 peptides in the composition are heteroclitic. In another embodiment, 2 of the WT1 peptides in the composition are unaltered, and 2 are heteroclitic. In another embodiment, more than 2 of the WT1 peptides in the composition are unaltered. In another embodiment, more than 2 of the WT1 peptides in the composition are heteroclitic. In another embodiment, more than 2 of the WT1 peptides in the composition are unaltered, and more than 2 are heteroclitic. Each possibility represents a separate embodiment of the present invention.

In another embodiment, 1 of the additional WT1 peptides in a composition of the present invention has a sequence selected from the sequences set forth in SEQ ID No: 1-160, 162-185, 190, 191 or 193. In another embodiment, 2 of the additional WT1 peptides have a sequence selected from the sequences set forth in SEQ ID No: 1-160, 162-185, 190, 191 or 193. In another embodiment, 3 of the additional WT1 peptides have a sequence selected from the sequences set forth in SEQ ID No: 1-160, 162-185, 190, 191 or 193.

In another embodiment, any other immunogenic WT1 peptide known in the art is utilized as an additional WT1 peptide. In another embodiment, any combination of immunogenic WT1 peptides known in the art is utilized. Non-limiting sources of other WT peptides include WO2005053618, WO2007047764 and WO2007120673.

Each additional WT1 peptide, and each combination thereof, represents a separate embodiment of the present invention.

In another embodiment, a composition of the present invention contains 2 HLA class II heteroclitic peptides that are derived from the same isolated WT1 peptide of the present invention. In another embodiment, the 2 HLA class II heteroclitic peptides contain mutations in different HLA class II molecule anchor residues. In another embodiment, the 2 HLA class II heteroclitic peptides contain different mutations in the same anchor residues. In another embodiment, 2 of the HLA class II heteroclitic peptides are derived from different isolated WT1 peptides of the present invention. Each possibility represents a separate embodiment of the present invention.

In another embodiment, 2 WT1 peptides of the present invention, or the WT1 peptides that correspond to two HLA class II heteroclitic peptides of the present invention, overlap with one another. In another embodiment, the overlap between the peptides is at least 7 amino acids (AA). In another embodiment, the overlap is at least 8 AA. In another embodiment, the overlap is at least 9 AA. In another embodiment, the overlap is 7 AA. In another embodiment, the overlap is 8 AA. In another embodiment, the overlap is 9 AA. In another embodiment, the overlap is 10 AA. In another embodiment, the overlap is 11 AA. In another embodiment, the overlap is 12 AA. In another embodiment, the overlap is 13 AA. In another embodiment, the overlap is 14 AA. In another embodiment, the overlap is 15 AA. In another embodiment, the overlap is 16 AA. In another embodiment, the overlap is more than 16 AA. Each possibility represents a separate embodiment of the present invention.

In another embodiment, the peptides in a composition of the present invention bind to 2 distinct HLA class II molecules. In another embodiment, the peptides bind to 3 distinct HLA class II molecules. In another embodiment, the peptides bind to 4 distinct HLA class II molecules. In another embodiment, the peptides bind to 5 distinct HLA class II molecules. In another embodiment, the peptides bind to more than 5 distinct HLA class II molecules. In another embodiment, the peptides in the composition bind to the same HLA class II molecules.

In another embodiment, each of the WT 1 peptides in a composition of the present invention binds to a set of HLA class II molecules. In another embodiment, each of the WT1 peptides binds to a distinct set of HLA class II molecules. In another embodiment, the WT1 peptides in the composition bind to the same set of HLA class II molecules. In another embodiment, 2 of the WT1 peptides bind to a distinct but overlapping set of HLA class II molecules. In another embodiment, 2 or more of the WT1 peptides bind to the same set of HLA class II molecules, while another of the WT1 peptides binds to a distinct set. In another embodiment, 2 or more of the WT1 peptides bind to an overlapping set of HLA class II molecules, while another of the WT1 peptides binds to a distinct set.

In another embodiment, 2 or more of the WT1 peptides in a composition of the present invention each binds to more than 1 HLA-DRB molecule. In another embodiment, the 4 or more HLA-DRB molecules bound by the peptides in the composition are distinct from one another. In another embodiment, the HLA-DRB molecules are encoded by different HLA-DRB alleles. Each possibility represents a separate embodiment of the present invention.

In another embodiment, 2 or more of the HLA class II molecules bound by WT1 peptides in a composition of the present invention are HLA-DRB molecules. In another embodiment, 3 or more of the HLA class II molecules that are bound are HLA-DRB molecules. In other embodiments, the HLA class II molecules that are bound can be any of the HLA class II molecules enumerated herein. In another embodiment, the HLA class II molecules that are bound are encoded by 2 or more distinct HLA class II alleles at a given locus. In another embodiment, the HLA class II molecules that are bound are encoded by HLA class II genes at 2 or more distinct loci.

Each of the above compositions represents a separate embodiment of the present invention.

In another embodiment, a "set of HLA class II molecules" refers to the HLA class II molecules encoded by different alleles at a particular locus. In another embodiment, the term refers to HLA class II molecules with a particular binding specificity. In another embodiment, the term refers to HLA class II molecules with a particular peptide consensus sequence. In another embodiment, the term refers to a superfamily of HLA class II molecules. Each possibility represents a separate embodiment of the present invention.

In another embodiment, the present invention provides a composition comprising an unaltered HLA class II molecule-binding WT1 peptide of the present invention and a second, HLA class I molecule-binding WT1 peptide. In another embodiment, the composition comprises more than 1 HLA class II molecule-binding WT1 peptide of the present invention, in addition to the HLA class I molecule-binding WT1 peptide. In another embodiment, the composition comprises more than 1 HLA class I molecule-binding WT1 peptide, in addition to the HLA class II molecule-binding WT1 peptide. Each possibility represents a separate embodiment of the present invention.

In another embodiment, the AA sequence of the HLA class I molecule-binding WT1 peptide comprises a sequence selected from SEQ ID No: 1-160, 162-185, 190, 191 or 193. In another embodiment, the AA sequence of the HLA class I molecule-binding WT1 peptide is selected from the sequences set forth in SEQ ID No: 1-160, 162-185, 190, 191 or 193. Each possibility represents a separate embodiment of the present invention.

In another embodiment, the HLA class I molecule-binding WT1 peptide is an HLA class I heteroclitic peptide. In another embodiment, the HLA class I molecule-binding WT1 peptide contains a mutation in an HLA class I molecule anchor residue thereof, as described further herein. As provided herein, WT1-derived peptides were modified in HLA anchor residues to generate heteroclitic peptides with increased predicted binding to HLA-A0201 and HLA-A0301. Peptides with increased predicted binding also exhibited enhanced ability to bind HLA class I molecules and increased immunogenicity.

In another embodiment, the mutation that enhances MHC binding is in the residue at position 1 of the HLA class I heteroclitic peptide. In another embodiment, the residue is changed to tyrosine. In another embodiment, the residue is changed to glycine. In another embodiment, the residue is changed to threonine. In another embodiment, the residue is changed to phenylalanine. In another embodiment, the residue is changed to any other residue known in the art. In another embodiment, a substitution in position 1 (e.g. to tyrosine) stabilizes the binding of the position 2 anchor residue.

In another embodiment, the mutation is in position 2 of the HLA class I heteroclitic peptide. In another embodiment, the residue is changed to leucine. In another embodiment, the residue is changed to valine. In another embodiment, the residue is changed to isoleucine. In another embodiment, the residue is changed to methionine. In another embodiment, the residue is changed to any other residue known in the art.

In another embodiment, the mutation is in position 6 of the HLA class I heteroclitic peptide. In another embodiment, the residue is changed to valine. In another embodiment, the residue is changed to cysteine. In another embodiment, the residue is changed to glutamine. In another embodiment, the residue is changed to histidine. In another embodiment, the residue is changed to any other residue known in the art.

In another embodiment, the mutation is in position 9 of the HLA class I heteroclitic peptide. In another embodiment, the mutation changes the residue at the C-terminal position thereof. In another embodiment, the residue is changed to valine. In another embodiment, the residue is changed to threonine. In another embodiment, the residue is changed to isoleucine. In another embodiment, the residue is changed to leucine. In another embodiment, the residue is changed to alanine. In another embodiment, the residue is changed to cysteine. In another embodiment, the residue is changed to any other residue known in the art.

In another embodiment, the point mutation is in a primary anchor residue. In another embodiment, the HLA class I primary anchor residues are positions 2 and 9. In another embodiment, the point mutation is in a secondary anchor residue. In another embodiment, the HLA class I secondary anchor residues are positions 1 and 8. In another embodiment, the HLA class I secondary anchor residues are positions 1, 3, 6, 7, and 8. In another embodiment, the point mutation is in a position selected from positions 4, 5, and 8. Each possibility represents a separate embodiment of the present invention.

In another embodiment, the point mutation is in 1 or more residues in positions selected from positions 1, 2, 8, and 9 of the HLA class I binding motif. In another embodiment, the point mutation is in 1 or more residues in positions selected from positions 1, 3, 6, and 9. In another embodiment, the point mutation is in 1 or more residues in positions selected from positions 1, 2, 6, and 9. In another embodiment, the point mutation is in 1 or more residues in positions selected from positions 1, 6, and 9. In another embodiment, the point mutation is in 1 or more residues in positions selected from positions 1, 2, and 9. In another embodiment, the point mutation is in 1 or more residues in positions selected from positions 1, 3, and 9. In another embodiment, the point mutation is in 1 or more residues in positions selected from positions 2 and 9. In another embodiment, the point mutation is in 1 or more residues in positions selected from positions 6 and 9. Each possibility represents a separate embodiment of the present invention.

Each of the above anchor residues and substitutions represents a separate embodiment of the present invention.

In another embodiment, the HLA class I molecule-binding WT peptide has length of 9 AA. In another embodiment, the peptide has length of 10 AA. As provided herein, native and heteroclitic peptides of 9-10 AA exhibited substantial binding to HLA class I molecules and ability to elicit cytokine secretion and cytolysis by CTL.

In another embodiment, the HLA class I molecule that is bound by the HLA class I molecule-binding WT1 peptide is an HLA-A molecule. In another embodiment, the HLA class I-molecule is an HLA-A2 molecule. In another embodiment, the HLA class I-molecule is an HLA-A3 molecule. In another embodiment, the HLA class I-molecule is an HLA-A1 1 molecule. In another embodiment, the HLA class I-molecule is an HLA-B 8 molecule. In another embodiment, the HLA class I-molecule is an HLA-0201 molecule. In another embodiment, the HLA class I-molecule binds any other HLA class I molecule known in the art. Each possibility represents a separate embodiment of the present invention.

In another embodiment, a WT1 peptide of methods and compositions of the present invention has a length of 8-30 amino acids. In another embodiment, the peptide has a length of 9-11 AA. In another embodiment, the peptide ranges in size from 7-25 AA, or in another embodiment, 8-11, or in another embodiment, 8-15, or in another embodiment, 9-20, or in another embodiment, 9-18, or in another embodiment, 9-15, or in another embodiment, 8-12, or in another embodiment, 9-11 AA in length. In another embodiment, the peptide is 8 AA in length, or in another embodiment, 9 AA or in another embodiment, 10 AA or in another embodiment, 12 AA or in another embodiment, 25 AA in length, or in another embodiment, any length therebetween.

In another embodiment, the peptide is of greater length, for example 50, or 100, or more. In this embodiment, the cell processes the peptide to a length of 7 and 25 AA in length. In this embodiment, the cell processes the peptide to a length of 9-11 AA Each possibility represents a separate embodiment of the present invention.

In another embodiment, the peptide is 15-23 AA in length. In another embodiment, the length is 15-24 AA. In another embodiment, the length is 15-25 AA. In another embodiment, the length is 15-26 AA. In another embodiment, the length is 15-27 AA. In another embodiment, the length is 15-28 AA. In another embodiment, the length is 14-30 AA. In another embodiment, the length is 14-29 AA. In another embodiment, the length is 14-28 AA. In another embodiment, the length is 14-26 AA. In another embodiment, the length is 14-24 AA. In another embodiment, the length is 14-22 AA. In another embodiment, the length is 14-20 AA. In another embodiment, the length is 16-30 AA. In another embodiment, the length is 16-28 AA. In another embodiment, the length is 16-26 AA. In another embodiment, the length is 16-24 AA. In another embodiment, the length is 16-22 AA. In another embodiment, the length is 18-30 AA. In another embodiment, the length is 18-28 AA. In another embodiment, the length is 18-26 AA. In another embodiment, the length is 18-24 AA. In another embodiment, the length is 18-22 AA. In another embodiment, the length is 18-20 AA. In another embodiment, the length is 20-30 AA. In another embodiment, the length is 20-28 AA. In another embodiment, the length is 20-26 AA. In another embodiment, the length is 20-24 AA. In another embodiment, the length is 22-30 AA. In another embodiment, the length is 22-28 AA. In another embodiment, the length is 22-26 AA. In another embodiment, the length is 24-30 AA. In another embodiment, the length is 24-28 AA. In another embodiment, the length is 24-26 AA.

Each of the above peptides, peptide lengths, and types of peptides represents a separate embodiment of the present invention.

In another embodiment, minor modifications are made to peptides of the present invention without decreasing their affinity for HLA molecules or changing their TCR specificity, utilizing principles well known in the art. In the case of HLA class I-binding peptides, "minor modifications" refers, in another embodiment, to e.g. insertion, deletion, or substitution of one AA, inclusive, or deletion or addition of 1-3 AA outside of the residues between 2 and 9, inclusive. While the computer algorithms described herein are useful for predicting the MHC class I-binding potential of peptides, they have 60-80% predictive accuracy; and thus, the peptides should be evaluated empirically before a final determination of MHC class I-binding affinity is made. Thus, peptides of the present invention are not limited to peptides predicated by the algorithms to exhibit strong MHC class I-binding affinity. The types are modifications that can be made are listed below. Each modification represents a separate embodiment of the present invention.

In another embodiment, a peptide enumerated in the Examples of the present invention is further modified by mutating an anchor residue to an MHC class I preferred anchor residue, which can be, in other embodiments, any of the anchor residues enumerated herein. In another embodiment, a peptide of the present invention containing an MHC class I preferred anchor residue is further modified by mutating the anchor residue to a different MHC class I preferred residue for that location. The different preferred residue can be, in other embodiments, any of the preferred residues enumerated herein.

In another embodiment, the anchor residue that is further modified is in the 1 position. In another embodiment, the anchor residue is in the 2 position. In another embodiment, the anchor residue is in the 3 position. In another embodiment, the anchor residue is in the 4 position. In another embodiment, the anchor residue is in the 5 position. In another embodiment, the anchor residue is in the 6 position. In another embodiment, the anchor residue is in the 7 position. In another embodiment, the anchor residue is in the 8 position. In another embodiment, the anchor residue is in the 9 position. In the case of HLA class I-binding peptides, residues other than 2 and 9 can serve as secondary anchor residues; therefore, mutating them can improve MHC class I binding. Each possibility represents a separate embodiment of the present invention.

In another embodiment, a peptide of methods and compositions of the present invention is a length variant of a peptide enumerated in the Examples. In another embodiment, the length variant is one amino acid (AA) shorter than the peptide from the Examples. In another embodiment, the length variant is two AA shorter than the peptide from the Examples. In another embodiment, the length variant is more than two AA shorter than the peptide from the Examples. In another embodiment, the shorter peptide is truncated on the N-terminal end. In another embodiment, the shorter peptide is truncated on the C-terminal end. In another embodiment, the truncated peptide is truncated on both the N-terminal and C-terminal ends. Peptides are, in another embodiment, amenable to truncation without changing affinity for HLA molecules, as is well known in the art.

Each of the above truncated peptides represents a separate embodiment of the present invention.

In another embodiment, the length variant is longer than a peptide enumerated in the Examples of the present invention. In another embodiment, the longer peptide is extended on the N-terminal end in accordance with the surrounding WT1 sequence. Peptides are, in another embodiment, amenable to extension on the N-terminal end without changing affinity for HLA molecules, as is well known in the art. Such peptides are thus equivalents of the peptides enumerated in the Examples. In another embodiment, the N-terminal extended peptide is extended by one residue. In another embodiment, the N-terminal extended peptide is extended by two residues. In another embodiment, the N-terminal extended peptide is extended by three residues. In another embodiment, the N-terminal extended peptide is extended by more than three residues.

In another embodiment, the longer peptide is extended on the C terminal end in accordance with the surrounding WT1 sequence. Peptides are, in another embodiment, amenable to extension on the C-terminal end without changing affinity for HLA molecules, as is well known in the art. Such peptides are thus equivalents of the peptides enumerated in the Examples of the present invention. In another embodiment, the C-terminal extended peptide is extended by one residue. In another embodiment, the C-terminal extended peptide is extended by two residues. In another embodiment, the C-terminal extended peptide is extended by three residues. In another embodiment, the C-terminal extended peptide is extended by more than three residues.

In another embodiment, the extended peptide is extended on both the N-terminal and C-terminal ends in accordance with the surrounding WT1 sequence.

Each of the above extended peptides represents a separate embodiment of the present invention.

In another embodiment, a truncated peptide of the present invention retains the HLA anchor residues (e.g. the HLA class I anchor residues) on the second residue and the C-terminal residue, with a smaller number of intervening residues (e.g. 5) than a peptide enumerated in the Examples of the present invention. Peptides are, in another embodiment, amenable to such mutation without changing affinity for HLA molecules. In another embodiment, such a truncated peptide is designed by removing one of the intervening residues of one of the above sequences. In another embodiment, the HLA anchor residues are retained on the second and eighth residues. In another embodiment, the HLA anchor residues are retained on the first and eighth residues. Each possibility represents a separate embodiment of the present invention.

In another embodiment, an extended peptide of the present invention retains the HLA anchor residues (e.g. the HLA class I anchor residues) on the second residue and the C-terminal residue, with a larger number of intervening residues (e.g. 7 or 8) than a peptide enumerated in the Examples of the present invention. In another embodiment, such an extended peptide is designed by adding one or more residues between two of the intervening residues of one of the above sequences. It is well known in the art that residues can be removed from or added between the intervening sequences of HLA-binding peptides without changing affinity for HLA. Such peptides are thus equivalents of the peptides enumerated in the Examples of the present invention. In another embodiment, the HLA anchor residues are retained on the second and ninth residues. In another embodiment, the HLA anchor residues are retained on the first and eighth residues. In another embodiment, the HLA anchor residues are retained on the two residues separated by six intervening residues. Each possibility represents a separate embodiment of the present invention.

"Fragment," in another embodiment, refers to a peptide of 11 or more AA in length. In another embodiment, a peptide fragment of the present invention is 16 or more AA long. In another embodiment, the fragment is 12 or more AA long. In another embodiment, the fragment is 13 or more AA. In another embodiment, the fragment is 14 or more AA. In another embodiment, the fragment is 15 or more AA. In another embodiment, the fragment is 17 or more AA. In another embodiment, the fragment is 18 or more AA. In another embodiment, the fragment is 19 or more AA. In another embodiment, the fragment is 22 or more AA. In another embodiment, the fragment is 8-12 AA. In another embodiment, the fragment is about 8-12 AA. In another embodiment, the fragment is 16-19 AA. In another embodiment, the fragment is about 16-19 AA. In another embodiment, the fragment 10-25 AA. In another embodiment, the fragment is about 10-25 AA. In another embodiment, the fragment has any other length. Each possibility represents a separate embodiment of the present invention.

"Fragment of a WT1 protein," in another embodiment, refers to any of the definitions of "fragment" found herein. Each definition represents a separate embodiment of the present invention.

In another embodiment, a peptide of the present invention is homologous to a peptide enumerated in the Examples. The terms "homology," "homologous," etc., when in reference to any protein or peptide, refer, in another embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, the term "homology," when in reference to any nucleic acid sequence similarly indicates a percentage of nucleotides in a candidate sequence that are identical with the nucleotides of a corresponding native nucleic acid sequence.

Homology is, in another embodiment, determined by computer algorithm for sequence alignment, by methods well described in the art. In other embodiments, computer algorithm analysis of nucleic acid sequence homology includes the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from SEQ ID No: 1-160, 162-185, 190, 191 or 193 of greater than 70%. In another embodiment, "homology" refers to identity to a sequence selected from SEQ ID No: 1-160, 162-185, 190, 191 or 193 of greater than 72%. In another embodiment, "homology" refers to identity to one of SEQ ID No: 1-160, 162-185, 190, 191 or 193 of greater than 75%. In another embodiment, "homology" refers to identity to a sequence selected from SEQ ID No: 1-160, 162-185, 190, 191 or 193 of greater than 78%. In another embodiment, "homology" refers to identity to one of SEQ ID No: 1-160, 162-185, 190, 191 or 193 of greater than 80%. In another embodiment, "homology" refers to identity to one of SEQ ID No: 1-160, 162-185, 190, 191 or 193 of greater than 82%. In another embodiment, "homology" refers to identity to a sequence selected from SEQ ID No: 1-160, 162-185, 190, 191 or 193 of greater than 83%. In another embodiment, "homology" refers to identity to one of SEQ ID No: 1-160, 162-185, 190, 191 or 193 of greater than 85%. In another embodiment, "homology" refers to identity to one of SEQ ID No: 1-160, 162-185, 190, 191 or 193 of greater than 87%. In another embodiment, "homology" refers to identity to a sequence selected from SEQ ID No: 1-160, 162-185, 190, 191 or 193 of greater than [0128] 88%. In another embodiment, "homology" refers to identity to one of SEQ ID No: 1-160, 162-185, 190, 191 or 193 of greater than 90%. In another embodiment, "homology" refers to identity to one of SEQ ID No: 1-160, 162-185, 190, 191 or 193 of greater than 92%. In another embodiment, "homology" refers to identity to a sequence selected from SEQ ID No: 1-160, 162-185, 190, 191 or 193 of greater than 93%. In another embodiment, "homology" refers to identity to one of SEQ ID No: 1-160, 162-185, 190, 191 or 193 of greater than 95%. In another embodiment, "homology" refers to identity to a sequence selected from SEQ ID No: 1-160, 162-185, 190, 191 or 193 of greater than 96%. In another embodiment, "homology" refers to identity to one of SEQ ID No: 1-160, 162-185, 190, 191 or 193 of greater than 97%. In another embodiment, "homology" refers to identity to one of SEQ ID No: 1-160, 162-185, 190, 191 or 193 of greater than 98%. In another embodiment, "homology" refers to identity to one of SEQ ID No: 1-160, 162-185, 190, 191 or 193 of greater than 99%. In another embodiment, "homology" refers to identity to one of SEQ ID No: 1-160, 162-185, 190, 191 or 193 of 100%. Each possibility represents a separate embodiment of the present invention. [00114] In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N. Y). In another embodiments, methods of hybridization are carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA.

Each of the above homologues and variants of peptides enumerated in the Examples represents a separate embodiment of the present invention.

In another embodiment, the present invention provides a composition comprising a peptide of this invention. In another embodiment, the composition further comprises a pharmaceutically acceptable carrier. In another embodiment, the composition further comprises an adjuvant. In another embodiment, the composition comprises 2 or more peptides of the present invention. In another embodiment, the composition further comprises any of the additives, compounds, or excipients set forth hereinbelow. In another embodiment, the adjuvant is KLH, QS21, Freund's complete or incomplete adjuvant, aluminum phosphate, aluminum hydroxide, BCG or alum. In other embodiments, the carrier is any carrier enumerated herein. In other embodiments, the adjuvant is any adjuvant enumerated herein. Each possibility represents a separate embodiment of the present invention.

In another embodiment, this invention provides a vaccine comprising a peptide of this invention. In another embodiment, this invention provides a vaccine comprising an antigen-presenting cell (APC) and a peptide of this invention. In another embodiment, the vaccine further comprises a carrier. In another embodiment, the vaccine further comprises an adjuvant. In another embodiment, the vaccine further comprises an APC. In another embodiment, the vaccine further comprises a combination of more than 1 of an antigen, carrier, and/or APC. In another embodiment, the vaccine is a cell-based composition. Each possibility represents a separate embodiment of the present invention.

In another embodiment, the term "vaccine" refers to a material or composition that, when introduced into a subject, provides a prophylactic or therapeutic response for a particular disease, condition, or symptom of same. In another embodiment, this invention comprises peptide-based vaccines, wherein the peptide comprises any embodiment listed herein, including immunomodulating compounds such as cytokines, adjuvants, etc.

In another embodiment, a vaccine of methods and compositions of the present invention further comprises an adjuvant. In another embodiment, the adjuvant is a Montanide. In another embodiment the adjuvant is Montanide ISA 51. Montanide ISA 51 contains a natural metabolizable oil and a refined emulsifier. In another embodiment, the adjuvant is GM-CSF. Recombinant GM-CSF is a human protein grown, in another embodiment, in a yeast (S. cerevisiae) vector. GM-CSF promotes clonal expansion and differentiation of hematopoietic progenitor cells, APC, and dendritic cells and T cells.

In another embodiment, the adjuvant is a cytokine. In another embodiment, the adjuvant is a growth factor. In another embodiment, the adjuvant is a cell population. In another embodiment, the adjuvant is QS21. In another embodiment, the adjuvant is Freund's incomplete adjuvant. In another embodiment, the adjuvant is aluminum phosphate. In another embodiment, the adjuvant is aluminum hydroxide. In another embodiment, the adjuvant is BCG. In another embodiment, the adjuvant is alum.

In another embodiment, the adjuvant is an interleukin. In another embodiment, the adjuvant is a chemokine. In another embodiment, the adjuvant is any other type of adjuvant known in the art. In another embodiment, the WT1 vaccine comprises two the above adjuvants. In another embodiment, the WT1 vaccine comprises more than two the above adjuvants. Each possibility represents a separate embodiment of the present invention.

In other embodiments, a vaccine or composition of the present invention can comprise any of the embodiments of WT1 peptides of the present invention and combinations thereof. Each possibility represents a separate embodiment of the present invention.

It is to be understood that any embodiments described herein, regarding peptides, vaccines and compositions of this invention can be employed in any of the methods of this invention. Each combination of peptide, vaccine, or composition with a method represents an embodiment thereof.

In another embodiment, the present invention provides a method of treating a subject with a WT1-expressing cancer, the method comprising administering to the subject a WT1 vaccine of the present invention, thereby treating a subject with a WT1-expressing cancer.

In another embodiment, the present invention provides a method of treating a subject with an MDS, the method comprising administering to the subject a WT1 vaccine of the present invention, thereby treating a subject with an MDS.

In another embodiment, the present invention provides a method of suppressing or halting the progression of a WT1-expressing cancer in a subject, the method comprising administering to the subject a WT1 vaccine of the present invention, thereby suppressing or halting the progression of a WT1-expressing cancer.

In another embodiment, the present invention provides a method of reducing the incidence of a WT1-expressing cancer in a subject, the method comprising administering to the subject a WT1 vaccine of the present invention, thereby reducing the incidence of a WT1-expressing cancer in a subject.

In another embodiment, the present invention provides a method of reducing the incidence of an AML in a subject, the method comprising administering to the subject a WT1 vaccine of the present invention, thereby reducing the incidence of an AML.

In another embodiment, the present invention provides a method of reducing the incidence of relapse of a WT1-expressing cancer in a subject, the method comprising administering to the subject a WT1 vaccine of the present invention, thereby reducing the incidence of relapse of a WT1-expressing cancer in a subject.

In another embodiment, the present invention provides a method of reducing the incidence of relapse of an AML in a subject, the method comprising administering to the subject a WT1 vaccine of the present invention, thereby reducing the incidence of relapse of an AML in a subject.

In another embodiment, the present invention provides a method of breaking a T cell tolerance of a subject to a WT1-expressing cancer, the method comprising administering to the subject a WT1 vaccine of the present invention, thereby breaking a T cell tolerance to a WT1-expressing cancer.

In another embodiment, the present invention provides a method of treating a subject having a WT1-expressing cancer, comprising (a) inducing in a donor formation and proliferation of human cytotoxic T lymphocytes (CTL) that recognize a malignant cell of the cancer by a method of the present invention; and (b) infusing the human CTL into the subject, thereby treating a subject having a cancer.

In another embodiment, the present invention provides a method of treating a subject having a WT 1-expressing cancer, comprising (a) inducing ex vivo formation and proliferation of human CTL that recognize a malignant cell of the cancer by a method of the present invention, wherein the human immune cells are obtained from a donor; and (b) infusing the human CTL into the subject, thereby treating a subject having a cancer.

In another embodiment, the present invention provides a method of inducing formation and proliferation of (a) a WT1 protein-specific CD8$^+$ lymphocyte; or (b) a CD4$^+$ lymphocyte specific for the WT1 protein, or the combination thereof, the method comprising contacting a lymphocyte population with a peptide or composition of the present invention, thereby inducing formation and proliferation of (a) a WT1 protein-specific CD8$^+$ lymphocyte; or (b) a CD4$^+$ lymphocyte specific for the WT1 protein; or a combination thereof. This method can be conducted in vitro, ex vivo or in vivo. When conducted in vitro or ex vivo, these CTL can then be infused into a patient for therapeutic effect.

Methods for ex vivo immunotherapy are well known in the art and are described, for example, in United States Patent Application Ser. Nos. 2006/0057130, 2005/0221481, 2005/0214268, 2003/0175272, 2002/0127718, and U.S. Pat. No. 5,229,115, which are incorporated herein by reference. Additional methods are well known in the art and are described, for example, in Davis I D et al (Blood dendritic cells generated with Flt3 ligand and CD40 ligand prime CD8+ T cells efficiently in cancer patients. J Immunother. 2006 Sep.-Oct.; 29(5):499-511) and Mitchell M S et al (The cytotoxic T cell response to peptide analogs of the HLA-A*0201-restricted MUC1 signal sequence epitope, M1.2. Cancer Immunol Immunother. 2006 Jul. 28). Each method represents a separate embodiment of the present invention.

In another embodiment, the present invention provides a method of inducing the formation and proliferation of CTL specific for cells of a WT1-expressing cancer, the method comprising contacting a lymphocyte population with a vaccine of the present invention. In another embodiment, the vaccine is an APC associated with a peptide of the present invention. In another embodiment, the vaccine is an APC associated with a mixture of peptides of the present invention. Each possibility represents a separate embodiment of the present invention.

In another embodiment, this invention provides a method of generating a heteroclitic immune response in a subject, wherein the heteroclitic immune response is directed against a WT1-expressing cancer, the method comprising administering to the subject a vaccine of the present invention, thereby generating a heteroclitic immune response.

In another embodiment, the present invention provides a method of inducing an anti-mesothelioma immune response in a subject, the method comprising the step of contacting the subject with an immunogenic composition comprising (a) a WT1 protein; or (b) a fragment of a WT protein, thereby inducing an anti-mesothelioma immune response in a subject. In another embodiment, the mesothelioma is a malignant mesothelioma. Each possibility represents a separate embodiment of the present invention.

In another embodiment, the present invention provides a method of inducing an anti-mesothelioma immune response in a subject, the method comprising the step of contacting the subject with an immunogenic composition comprising a nucleotide molecule encoding (a) a WT1 protein; or (b) a fragment of a WT1 protein, thereby inducing an anti-mesothelioma immune response in a subject. In another embodiment, the mesothelioma is a malignant mesothelioma. Each possibility represents a separate embodiment of the present invention.

In another embodiment, the present invention provides a method of treating a subject with a mesothelioma, the method comprising the step of administering to the subject an immunogenic composition comprising (a) a WT1 protein; or (b) a fragment of a WT protein, thereby treating a subject with a mesothelioma. In another embodiment, the mesothelioma is a malignant mesothelioma. Each possibility represents a separate embodiment of the present invention.

In another embodiment, the present invention provides a method of treating a subject with a mesothelioma, the method comprising the step of administering to the subject an immunogenic composition comprising a nucleotide molecule encoding (a) a WT1 protein; or (b) a fragment of a WT1 protein, thereby treating a subject with a mesothelioma. In another embodiment, the mesothelioma is a malignant mesothelioma. Each possibility represents a separate embodiment of the present invention.

In another embodiment, the present invention provides a method of reducing an incidence of a mesothelioma, or its relapse, in a subject, the method comprising the step of administering to the subject an immunogenic composition comprising (a) a WT1 protein; or (b) a fragment of a WT protein, thereby reducing an incidence of a mesothelioma, or its relapse, in a subject. In another embodiment, the mesothelioma is a malignant mesothelioma. Each possibility represents a separate embodiment of the present invention.

In another embodiment, the present invention provides a method of reducing an incidence of a mesothelioma, or its relapse, in a subject, the method comprising the step of administering to the subject an immunogenic composition comprising a nucleotide molecule encoding (a) a WT1 protein; or (b) a fragment of a WT1 protein, thereby reducing an incidence of a mesothelioma, or its relapse, in a subject. In another embodiment, the mesothelioma is a malignant mesothelioma. Each possibility represents a separate embodiment of the present invention.

In another embodiment, a target cell of an immune response elicited by a method of the present invention presents the WT1 peptide of the present invention, or a corresponding WT1 fragment, on an HLA molecule. In another embodiment, the HLA molecule is an HLA class I molecule. In other embodiments, the HLA molecule is any HLA class I subtype or HLA class I molecule known in the art. In another embodiment, the immune response against the WT1 peptide or fragment is a heteroclitic immune response. Each possibility represents a separate embodiment of the present invention.

In another embodiment, the WT1-expressing cancer is an acute myelogenous leukemia (AML). In another embodiment, the WT1-expressing cancer is associated with a myelodysplastic syndrome (MDS). In another embodiment, the WT1-expressing cancer is an MDS. In another embodiment, the WT1-expressing cancer is a non-small cell lung cancer (NSCLC). In another embodiment, the WT1-expressing cancer is a Wilms' tumor. In another embodiment, the WT1-expressing cancer is a leukemia. In another embodiment, the WT1-expressing cancer is a hematological cancer. In another embodiment, the WT1-expressing cancer is a lymphoma. In another embodiment, the WT1-expressing cancer is a desmoplastic small round cell tumor. In another embodiment, the WT1-expressing cancer is a mesothelioma.

In another embodiment, the WT1-expressing cancer is a malignant mesothelioma. In another embodiment, the WT1-expressing cancer is a gastric cancer. In another embodiment, the WT1-expressing cancer is a colon cancer. In another embodiment, the WT1-expressing cancer is a lung cancer. In another embodiment, the WT1-expressing cancer is a breast cancer. In another embodiment, the WT1-expressing cancer is a germ cell tumor. In another embodiment, the WT1-expressing cancer is an ovarian cancer. In another embodiment, the WT 1-expressing cancer is a uterine cancer. In another embodiment, the WT 1-expressing cancer is a thyroid cancer. In another embodiment, the WT1-expressing cancer is a hepatocellular carcinoma. In another embodiment, the WT1-expressing cancer is a thyroid cancer. In another embodiment, the WT1-expressing cancer is a liver cancer. In another embodiment, the WT1-expressing cancer is a renal cancer. In another embodiment, the WT1-expressing cancer is a Kaposi's sarcoma. In another embodiment, the WT1-expressing cancer is a sarcoma. In another embodiment, the WT1-expressing cancer is any other carcinoma or sarcoma.

In another embodiment, the WT1-expressing cancer is a solid tumor. In another embodiment, the solid tumor is associated with a WT1-expressing cancer. In another embodiment, the solid tumor is associated with a myelodysplastic syndrome (MDS). In another embodiment, the solid tumor is associated with a non-small cell lung cancer (NSCLC). In another embodiment, the solid tumor is associated with a lung cancer. In another embodiment, the solid tumor is associated with a breast cancer. In another embodiment, the solid tumor is associated with a colorectal cancer. In another embodiment, the solid tumor is associated with a prostate cancer. In another embodiment, the solid tumor is associated with an ovarian cancer. In another embodiment, the solid tumor is associated with a renal cancer. In another embodiment, the solid tumor is associated with a pancreatic cancer. In another embodiment, the solid tumor is associated with a brain cancer. In another embodiment, the solid tumor is associated with a gastrointestinal cancer. In another embodiment, the solid tumor is associated with a skin cancer. In another embodiment, the solid tumor is associated with a melanoma.

In another embodiment, a cancer or tumor treated by a method of the present invention is suspected to express WT1. In another embodiment, WT1 expression has not been verified by testing of the actual tumor sample. In another embodiment, the cancer or tumor is of a type known to express WT1 in many cases. In another embodiment, the type expresses WT1 in the majority of cases.

Each type of WT1-expressing cancer or tumor, and cancer or tumor suspected to express WT1, represents a separate embodiment of the present invention.

Any embodiments enumerated herein, regarding peptides, vaccines and compositions of this invention can be employed in any of the methods of this invention, and each represents an embodiment thereof.

In another embodiment, multiple peptides of this invention are used to stimulate an immune response in methods of the present invention.

The methods disclosed herein will be understood by those in the art to enable design of other WT1-derived peptides. The methods further enable design of peptides binding to other HLA molecules. The methods further enable design of vaccines combining WT1-derived peptides of the present invention. Each possibility represents a separate embodiment of the present invention.

In another embodiment, vaccines of the present invention have the advantage of activating or eliciting WT1-specific CD4+ T cells containing a variety of different HLA class II alleles. In another embodiment, the vaccines have the advantage of activating or eliciting WT1-specific CD4+ T cells in a substantial proportion of the population (e.g. in different embodiments, 50%, 55%, 60%, 65%, 70%, 75%, 80%. 85%, 90%, 95%, or greater than 95%). In another embodiment, the vaccines activate or elicit WT1-specific CD4+ T cells in a substantial proportion of a particular population (e.g. American Caucasians). Each possibility represents a separate embodiment of the present invention.

In another embodiment, methods of the present invention provide for an improvement in an immune response that has already been mounted by a subject. In another embodiment, methods of the present invention comprise administering the peptide, composition, or vaccine 2 or more times. In another embodiment, the peptides are varied in their composition, concentration, or a combination thereof. In another embodiment, the peptides provide for the initiation of an immune response against an antigen of interest in a subject who has not yet initiated an immune response against the antigen. In another embodiment, the CTL that are induced proliferate in response to presentation of the peptide on the APC or cancer cell. In other embodiments, reference to modulation of the immune response involves, either or both the humoral and cell-mediated arms of the immune system, which is accompanied by the presence of Th2 and Th1 T helper cells, respectively, or in another embodiment, each arm individually.

In other embodiments, the methods affecting the growth of a tumor result in (1) the direct inhibition of tumor cell division, or (2) immune cell mediated tumor cell lysis, or both, which leads to a suppression in the net expansion of tumor cells.

Inhibition of tumor growth by either of these two mechanisms can be readily determined by one of ordinary skill in the art based upon a number of well-known methods. In another embodiment, tumor inhibition is determined by measuring the actual tumor size over a period of time. In another embodiment, tumor inhibition can be determined by estimating the size of a tumor (over a period of time) utilizing methods well known to those of skill in the art. More specifically, a variety of radiologic imaging methods (e.g., single photon and positron emission computerized tomography; see generally, "Nuclear Medicine in Clinical Oncology," Winkler, C. (ed.) Springer-Verlag, New York, 1986), can be utilized to estimate tumor size. Such methods can also utilize a variety of imaging agents, including for example, conventional imaging agents (e.g., Gallium-67 citrate), as well as specialized reagents for metabolite imaging, receptor imaging, or immunologic imaging (e.g., radio-labeled monoclonal antibody specific tumor markers). In addition, non-radioactive methods such as ultrasound (see, "Ultrasonic Differential Diagnosis of Tumors", Kossoff and Fukuda, (eds.), Igaku-Shoin, New York, 1984), can also be utilized to estimate the size of a tumor.

In addition to the in vivo methods for determining tumor inhibition discussed above, a variety of in vitro methods can be utilized in order to predict in vivo tumor inhibition. Representative examples include lymphocyte mediated anti-tumor cytolytic activity determined for example, by a $^{51}$Cr release assay (Examples), tumor dependent lymphocyte proliferation (Ioannides, et al., J. Immunol. 146(5):1700-1707, 1991), in vitro generation of tumor specific antibodies (Herlyn, et al., J. Immunol. Meth. 73:157-167, 1984), cell (e.g., CTL, helper T-cell) or humoral (e.g., antibody) mediated inhibition of cell growth in vitro (Gazit, et al., Cancer Immunol Immunother 35:135-144, 1992), and, for any of these assays, determination of cell precursor frequency (Vose, Int. J. Cancer 30:135-142 (1982), and others.

In another embodiment, methods of suppressing tumor growth indicate a growth state that is curtailed compared to growth without contact with, or exposure to a peptide of this invention. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth refers, in other embodiments, to slowing, delaying, or stopping tumor growth, or to tumor shrinkage. Each possibility represents a separate embodiment of the present invention.

In another embodiment of methods and compositions of the present invention, WT1 expression is measured. In another embodiment, WT1 transcript expression is measured. In another embodiment, WT1 protein levels in the tumor are measured. Each possibility represents a separate embodiment of the present invention.

Methods of determining the presence and magnitude of an immune response are well known in the art. In another embodiment, lymphocyte proliferation assays, wherein T cell uptake of a radioactive substance, e.g. $^3$H-thymidine is measured as a function of cell proliferation. In other embodiments, detection of T cell proliferation is accomplished by measuring increases in interleukin-2 (IL-2) production, $Ca^{2+}$ flux, or dye uptake, such as 3-(4,5-dimethylthiazol-2-yl)-2, 5-diphenyl-tetrazolium. Each possibility represents a separate embodiment of the present invention.

In another embodiment, CTL stimulation is determined by means known to those skilled in the art, including, detection of cell proliferation, cytokine production and others. Analysis of the types and quantities of cytokines secreted by T cells upon contacting ligand-pulsed targets can be a measure of functional activity. Cytokines can be measured by ELISA or ELISPOT assays to determine the rate and total amount of cytokine production. (Fujihashi K. et al. (1993) J. Immunol. Meth. 160: 181; Tanguay S. and Killion J. J. (1994) Lymphokine Cytokine Res. 13:259).

In another embodiment, CTL activity is determined by $^{51}$Cr-release lysis assay. Lysis of peptide-pulsed $^{51}$Cr-labeled targets by antigen-specific T cells can be compared for target cells pulsed with control peptide. In another embodiment, T cells are stimulated with a peptide of this invention, and lysis of target cells expressing the native peptide in the context of MHC can be determined. The kinetics of lysis as well as overall target lysis at a fixed timepoint (e.g., 4 hours) are used, in another embodiment, to evaluate ligand performance (Ware C. F. et al. (1983) J Immunol 131: 1312).

Methods of determining affinity of a peptide for an HLA molecule are well known in the art. In another embodiment, affinity is determined by TAP stabilization assays.

In another embodiment, affinity is determined by competition radioimmunoassay. In another embodiment, the following protocol is utilized: Target cells are washed two times in PBS with 1% bovine serum albumin (BSA; Fisher Chemicals, Fairlawn, N.J.). Cells are resuspended at $10^7$/ml on ice, and the native cell surface bound peptides are stripped for 2 minutes at 0[deg.] C using citrate-phosphate buffer in the presence of 3 mg/ml beta2 microglobulin. The pellet is resuspended at $5 \times 10^6$ cells/ml in PBS/1% BSA in the presence of 3 mg/ml beta2 microglobulin and 30 mg/ml deoxyribonuclease, and 200 ml aliquots are incubated in the presence or absence of HLA-specific peptides for 10 min at 20° C., then with $^{125}$I-labeled peptide for 30 min at 20° C.

Total bound $^{125}$I is determined after two washes with PBS/ 2% BSA and one wash with PBS. Relative affinities are determined by comparison of escalating concentrations of the test peptide versus a known binding peptide.

In another embodiment, a specificity analysis of the binding of peptide to HLA on surface of live cells (e.g. SKLY-16 cells) is conducted to confirm that the binding is to the appropriate HLA molecule and to characterize its restriction. This includes, in another embodiment, competition with excess unlabeled peptides known to bind to the same or disparate HLA molecules and use of target cells which express the same or disparate HLA types. This assay is performed, in another embodiment, on live fresh or 0.25% paraformaldehyde-fixed human PBMC, leukemia cell lines and EBV-transformed T-cell lines of specific HLA types. The relative avidity of the peptides found to bind MHC molecules on the specific cells are assayed by competition assays as described above against $^{125}$I-labeled peptides of known high affinity for the relevant HLA molecule, e.g., tyrosinase or HBV peptide sequence. In another embodiment, an HLA class II-binding peptide of methods and compositions of the present invention is longer than the minimum length for binding to an HLA class II molecule, which is, in another embodiment, about 12 AA. In another embodiment, increasing the length of the HLA class II-binding peptide enables binding to more than one HLA class II molecule. In another embodiment, increasing the length enables binding to an HLA class II molecule whose binding motif is not known. In another embodiment, increasing the length enables binding to an HLA class I molecule. In another embodiment, the binding motif of the HLA class I molecule is known. In another embodiment, the binding motif of the HLA class I molecule is not known. Each possibility represents a separate embodiment of the present invention.

In another embodiment, the peptides utilized in methods and compositions of the present invention comprise a non-classical amino acid such as: 1,2,3,4-tetrahydroisoquinoline-3-carboxylate (Kazmierski et al. (1991) J. Am Chem. Soc. 113:2275-2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby (1991) Tetrahedron Lett. 32(41): 5769-5772); 2-aminotetrahydronaphthalene-2-carboxylic acid (Landis (1989) Ph.D. Thesis, University of Arizona); hydroxy-1,2,3,4-tetrahydroisoquinoline-3-carboxylate (Miyake et al. (1984) J. Takeda Res. Labs. 43:53-76) histidine isoquinoline carboxylic acid (Zechel et al. (1991) Int. J. Pep. Protein Res. 38(2):131-138); and HIC (histidine cyclic urea), (Dharanipragada et al. (1993) Int. J. Pep. Protein Res. 42(1):68-77) and ((1992) Acta. Crst., Crystal Struc. Comm 48(IV): 1239-124).

In another embodiment, a peptide of this invention comprises an AA analog or peptidomimetic, which, in other embodiments, induces or favors specific secondary structures. Such peptides comprise, in other embodiments, the following: LL-Acp (LL-3-amino-2-propenidone-6-carboxylic acid), a [beta]-turn inducing dipeptide analog (Kemp et al. (1985) J. Org. Chem. 50:5834-5838); [beta]-sheet inducing analogs (Kemp et al. (1988) Tetrahedron Lett. 29:5081-5082); [beta]-turn inducing analogs (Kemp et al. (1988) Tetrahedron Left. 29:5057-5060); alpha-helix inducing analogs (Kemp et al. (1988) Tetrahedron Left. 29:4935-4938); gamma-turn inducing analogs (Kemp et al. (1989) J. Org. Chem. 54:109:115); analogs provided by the following references: Nagai and Sato (1985) Tetrahedron Lett. 26:647-650; and DiMaio et al. (1989) J. Chem. Soc. Perkin Trans, p. 1687; a Gly-Ala turn analog (Kahn et al. (1989) Tetrahedron Lett. 30:2317); amide bond isostere (Jones et al. (1988) Tetrahedron Left. 29(31):3853-3856); tretrazol (Zabrocki et al. (1988) J. Am. Chem. Soc. 110:5875-5880); DTC (Samanen et al. (1990) Int. J. Protein Pep. Res. 35:501:509); and analogs taught in Olson et al. (1990) J. Am. Chem. Sci. 112:323-333 and Garvey et al. (1990) J. Org. Chem. 55(3):936-940. Conformationally restricted mimetics of beta turns and beta bulges, and peptides containing them, are described in U.S. Pat. No. 5,440,013, issued Aug. 8, 1995 to Kahn.

In other embodiments, a peptide of this invention is conjugated to one of various other molecules, as described hereinbelow, which can be via covalent or non-covalent linkage (complexed), the nature of which varies, in another embodiment, depending on the particular purpose. In another embodiment, the peptide is covalently or non-covalently complexed to a macromolecular carrier, (e.g. an immunogenic carrier), including, but not limited to, natural and synthetic polymers, proteins, polysaccharides, polypeptides (amino acids), polyvinyl alcohol, polyvinyl pyrrolidone, and lipids. In another embodiment, a peptide of this invention is linked to a substrate. In another embodiment, the peptide is conjugated to a fatty acid, for introduction into a liposome (U.S. Pat. No. 5,837,249). In another embodiment, a peptide of the invention is complexed covalently or non-covalently with a solid support, a variety of which are known in the art. In another embodiment, linkage of the peptide to the carrier, substrate, fatty acid, or solid support serves to increase an elicited an immune response.

In other embodiments, the carrier is thyroglobulin, an albumin (e.g. human serum albumin), tetanus toxoid, polyamino acids such as poly (lysine: glutamic acid), an influenza protein, hepatitis B virus core protein, keyhole limpet hemocyanin, an albumin, or another carrier protein or carrier peptide; hepatitis B virus recombinant vaccine, or an APC. Each possibility represents a separate embodiment of the present invention.

In another embodiment, the term "amino acid" (AA) refers to a natural or, in another embodiment, an unnatural or synthetic AA, and can include, in other embodiments, glycine, D- or L optical isomers, AA analogs, peptidomimetics, or combinations thereof.

In another embodiment, the terms "cancer," "neoplasm," "neoplastic" or "tumor," are used interchangeably and refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. In another embodiment, a tumor is detectable on the basis of tumor mass; e.g., by such procedures as CAT scan, magnetic resonance imaging (MRI), X-ray, ultrasound or palpation, and in another embodiment, is identified by biochemical or immunologic findings, the latter which is used to identify cancerous cells, as well, in other embodiments.

Methods for synthesizing peptides are well known in the art. In another embodiment, the peptides of this invention are synthesized using an appropriate solid-state synthetic procedure (see for example, Steward and Young, Solid Phase Peptide Synthesis, Freemantle, San Francisco, Calif. (1968); Merrifield (1967) Recent Progress in Hormone Res 23: 451). The activity of these peptides is tested, in other embodiments, using assays as described herein.

In another embodiment, the peptides of this invention are purified by standard methods including chromatography (e.g., ion exchange, affinity, and sizing column chromatography), centrifugation, differential solubility, or by any other standard technique for protein purification. In another embodiment, immuno-affinity chromatography is used, whereby an epitope is isolated by binding it to an affinity column comprising antibodies that were raised against that peptide, or a related peptide of the invention, and were affixed to a stationary support.

In another embodiment, affinity tags such as hexa-His (Invitrogen), Maltose binding domain (New England Biolabs), influenza coat sequence (Kolodziej et al. (1991) Meth. Enzymol. 194:508-509), glutathione-S-transferase, or others, are attached to the peptides of this invention to allow easy purification by passage over an appropriate affinity column. Isolated peptides can also be physically characterized, in other embodiments, using such techniques as proteolysis, nuclear magnetic resonance, and x-ray crystallography.

In another embodiment, the peptides of this invention are produced by in vitro translation, through known techniques, as will be evident to one skilled in the art. In another embodiment, the peptides are differentially modified during or after translation, e.g., by phosphorylation, glycosylation, cross-linking, acylation, proteolytic cleavage, linkage to an antibody molecule, membrane molecule or other ligand, (Ferguson et al. (1988) Ann. Rev. Biochem. 57:285-320).

In another embodiment, the peptides of this invention further comprise a detectable label, which in another embodiment, is fluorescent, or in another embodiment, luminescent, or in another embodiment, radioactive, or in another embodiment, electron dense. In other embodiments, the detectable label comprises, for example, green fluorescent protein (GFP), DS-Red (red fluorescent protein), secreted alkaline phosphatase (SEAP), beta-galactosidase, luciferase, $^{32}P$, $^{125}I$, $^{3}H$ and $^{14}C$, fluorescein and its derivatives, rhodamine and its derivatives, dansyl and umbelliferone, luciferin or any number of other such labels known to one skilled in the art. The particular label used will depend upon the type of immunoassay used.

In another embodiment, a peptide of this invention is linked to a substrate, which, in another embodiment, serves as a carrier. In another embodiment, linkage of the peptide to a substrate serves to increase an elicited an immune response.

In another embodiment, peptides of this invention are linked to other molecules, as described herein, using conventional cross-linking agents such as carbodiimide. Examples of carbodiimide are 1-cyclohexyl-3-(2-morpholinyl-(4-ethyl) carbodiimide (CMC), 1-ethyl-3-(3-dimethylaminopropyl) carbodiimide (EDC) and 1-ethyl-3-(4-azonia-44-dimethylpentyl) carbodiimide.

In other embodiments, the cross-linking agents comprise cyanogen bromide, glutaraldehyde and succinic anhydride. In general, any of a number of homo-bifunctional agents including a homo-bifunctional aldehyde, a homo-bifunctional epoxide, a homo-bifunctional imido-ester, a homo-bifunctional N-hydroxysuccinimide ester, a homo-bifunctional maleimide, a homo-bifunctional alkyl halide, a homo-bifunctional pyridyl disulfide, a homo-bifunctional aryl halide, a homo-bifunctional hydrazide, a homo-bifunctional diazonium derivative and a homo-bifunctional photoreactive compound can be used. Also envisioned, in other embodiments, are hetero-bifunctional compounds, for example, compounds having an amine-reactive and a sulfhydryl-reactive group, compounds with an amine-reactive and a photoreactive group and compounds with a carbonyl-reactive and a sulfhydryl-reactive group.

In other embodiments, the homo-bifunctional cross-linking agents include the bifunctional N-hydroxysuccinimide esters dithiobis(succinimidylpropionate), disuccinimidyl suberate, and disuccinimidyl tartarate; the bifunctional imido-esters dimethyl adipimidate, dimethyl pimelimidate, and dimethyl suberimidate; the bifunctional sulfhydryl-reactive crosslinkers 1,4-di-[3'-(2'-pyridyldithio)propionamido]butane, bismaleimidohexane, and bis-N-maleimido-1, 8-octane; the bifunctional aryl halides 1,5-difluoro-2,4-dinitrobenzene and 4,4'-difluoro-3,3'-dinitrophenylsulfone; bifunctional photoreactive agents such as bis-[b-(4-azidosalicylamido)ethyl]disulfide; the bifunctional aldehydes formaldehyde, malondialdehyde, succinaldehyde, glutaraldehyde, and adipaldehyde; a bifunctional epoxide such as 1,4-butaneodiol diglycidyl ether; the bifunctional hydrazides adipic acid dihydrazide, carbohydrazide, and succinic acid dihydrazide; the bifunctional diazoniums o-tolidine, diazotized and bis-diazotized benzidine; the bifunctional alkylhalides N,N'-ethylene-bis(iodoacetamide), N1N'-hexamethylene-bis(iodoacetamide), N,N'-undecamethylene-bis (iodoacetamide), as well as benzylhalides and halomustards, such as a 1a'-diiodo-p-xylene sulfonic acid and tri(2-chloroethyl)amine, respectively, In other embodiments, hetero-bifunctional cross-linking agents used to link the peptides to other molecules, as described herein, include, but are not limited to, SMCC (succinimidyl-4-(N-maleimidomethyl)cyclohexane-1-carboxylate), MB S (m-maleimidobenzoyl-N-hydroxysuccinimide ester), SIAB (N-succinimidyl(4-iodoacteyl)aminobenzoate), SMPB (succinimidyl-4-(p-maleimidophenyl) butyrate), GMBS (N-(.gamma.-maleimidobutyryloxy) succmimide ester), MPBH (4-(4-N-maleimidopohenyl) butyric acid hydrazide), M2C2H (4-(N-maleimidomethyl) cyclohexane-1-carboxyl-hydrazide), SMPT (succinimidyloxycarbonyl-a-methyl-a-(2-pyridyldithio)toluene), and SPDP (N-succinimidyl 3-(2-pyridyldithio)propionate).

In another embodiment, the peptides of the invention are formulated as non-covalent attachment of monomers through ionic, adsorptive, or biospecific interactions. Complexes of peptides with highly positively or negatively charged molecules can be accomplished, in another embodiment, through salt bridge formation under low ionic strength environments, such as in deionized water. Large complexes can be created, in another embodiment, using charged polymers such as poly-(L-glutamic acid) or poly-(L-lysine), which contain numerous negative and positive charges, respectively. In another embodiment, peptides are adsorbed to surfaces such as microparticle latex beads or to other hydrophobic polymers, of D-biotin (NHS-biotin), which reacts with available amine groups.

In another embodiment, a peptide of the present invention is linked to a carrier. In another embodiment, the carrier is KLH. In other embodiments, the carrier is any other carrier known in the art, including, for example, thyroglobulin, albumins such as human serum albumin, tetanus toxoid, polyamino acids such as poly (lysine:glutamic acid), influenza, hepatitis B virus core protein, hepatitis B virus recombinant vaccine and the like. Each possibility represents a separate embodiment of the present invention.

In another embodiment, the peptides of this invention are conjugated to a lipid, such as P3 CSS. In another embodiment, the peptides of this invention are conjugated to a bead.

In another embodiment, the compositions of this invention further comprise immunomodulating compounds. In other embodiments, the immunomodulating compound is a cytokine, chemokine, or complement component that enhances expression of immune system accessory or adhesion molecules, their receptors, or combinations thereof. In some embodiments, the immunomodulating compound include interleukins, for example interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-Ia and MIP-Ib, complement components, or combinations thereof. In other embodiments, the immunomodulating compound stimulate expression, or enhanced expression of OX40, OX40L (gp34), lymphotactin, CD40, CD40L, B7.1, B7.2, TRAP, ICAM-1, 2 or 3, cytokine receptors, or combination thereof.

In another embodiment, the immunomodulatory compound induces or enhances expression of co-stimulatory molecules that participate in the immune response, which include, in some embodiments, CD40 or its ligand, CD28, CTLA-4 or a B7 molecule. In another embodiment, the immunomodulatory compound induces or enhances expression of a heat stable antigen (HSA) (Liu Y. et al. (1992) J. Exp. Med. 175:437-445), chondroitin sulfate-modified MHC invariant chain (Ii-CS) (Naujokas M. F. et al (1993) Cell 74:257-268), or an intracellular adhesion molecule 1 (ICAM-I) (Van R. H. (1992) Cell 71: 1065-1068), which assists, in another embodiment, co-stimulation by interacting with their cognate ligands on the T cells.

In another embodiment, the composition comprises a solvent, including water, dispersion media, cell culture media, isotonic agents and the like. In another embodiment, the solvent is an aqueous isotonic buffered solution with a pH of around 7.0. In another embodiment, the composition comprises a diluent such as water, phosphate buffered saline, or saline. In another embodiment, the composition comprises a solvent, which is non-aqueous, such as propyl ethylene glycol, polyethylene glycol and vegetable oils.

In another embodiment, the composition is formulated for administration by any of the many techniques known to those of skill in the art. For example, this invention provides for administration of the pharmaceutical composition parenterally, intravenously, subcutaneously, intradermally, intramucosally, topically, orally, or by inhalation.

In another embodiment, the vaccine comprising a peptide of this invention further comprises a cell population, which, in another embodiment, comprises lymphocytes, monocytes, macrophages, dendritic cells, endothelial cells, stem cells or combinations thereof, which, in another embodiment are autologous, syngeneic or allogeneic, with respect to each other. In another embodiment, the cell population comprises a peptide of the present invention. In another embodiment, the cell population takes up the peptide. Each possibility represents a separate embodiment of the present invention.

In another embodiment, the cell populations of this invention are obtained from in vivo sources, such as, for example, peripheral blood, leukopheresis blood product, apheresis blood product, peripheral lymph nodes, gut associated lymphoid tissue, spleen, thymus, cord blood, mesenteric lymph nodes, liver, sites of immunologic lesions, e.g. synovial fluid, pancreas, cerebrospinal fluid, tumor samples, granulomatous tissue, or any other source where such cells can be obtained. In another embodiment, the cell populations are obtained from human sources, which are, in other embodiments, from human fetal, neonatal, child, or adult sources. In another embodiment, the cell populations of this invention are obtained from animal sources, such as, for example, porcine or simian, or any other animal of interest. In another embodiment, the cell populations of this invention are obtained from subjects that are normal, or in another embodiment, diseased, or in another embodiment, susceptible to a disease of interest.

In another embodiment, the cell populations of this invention are separated via affinity-based separation methods. Techniques for affinity separation include, in other embodiments, magnetic separation, using antibody-coated magnetic beads, affinity chromatography, cytotoxic agents joined to a monoclonal antibody or use in conjunction with a monoclonal antibody, for example, complement and cytotoxins, and "panning" with an antibody attached to a solid matrix, such as a plate, or any other convenient technique. In other embodiment, separation techniques include the use of fluorescence activated cell sorters, which can have varying degrees of sophistication, such as multiple color channels, low angle and obtuse light scattering detecting channels, impedance channels, etc. In other embodiments, any technique that enables separation of the cell populations of this invention can be employed, and is to be considered as part of this invention.

In another embodiment, the dendritic cells are from the diverse population of morphologically similar cell types found in a variety of lymphoid and non-lymphoid tissues, qualified as such (Steinman (1991) Ann. Rev. Immunol. 9:271-296). In another embodiment, the dendritic cells used in this invention are isolated from bone marrow, or in another embodiment, derived from bone marrow progenitor cells, or, in another embodiment, from isolated from/derived from peripheral blood, or in another embodiment, derived from, or are a cell line.

In another embodiment, the cell populations described herein are isolated from the white blood cell fraction of a mammal, such as a murine, simian or a human (See, e.g., WO 96/23060). The white blood cell fraction can be, in another embodiment, isolated from the peripheral blood of the mammal.

Methods of isolating dendritic cells are well known in the art. In another embodiment, the DC are isolated via a method which includes the following steps: (a) providing a white blood cell fraction obtained from a mammalian source by methods known in the art such as leukophoresis; (b) separating the white blood cell fraction of step (a) into four or more subfractions by countercurrent centrifugal elutriation; (c) stimulating conversion of monocytes in one or more fractions from step (b) to dendritic cells by contacting the cells with calcium ionophore, GM-CSF and IL-13 or GM-CSF and IL-4, (d) identifying the dendritic cell-enriched fraction from step (c); and (e) collecting the enriched fraction of step (d), preferably at about 4[deg.] C.

In another embodiment, the dendritic cell-enriched fraction is identified by fluorescence-activated cell sorting, which identifies at least one of the following markers: HLA-DR, HLA-DQ, or B7.2, and the simultaneous absence of the following markers: CD3, CD14, CD16, 56, 57, and CD 19, 20.

In another embodiment, the cell population comprises lymphocytes, which are, in another embodiment, T cells, or in another embodiment, B cells. The T cells are, in other embodiments, characterized as NK cells, helper T cells, cytotoxic T lymphocytes (CTL), TBLs, native T cells, or combinations thereof. It is to be understood that T cells which are primary, or cell lines, clones, etc. are to be considered as part of this invention. In another embodiment, the T cells are CTL, or CTL lines, CTL clones, or CTLs isolated from tumor, inflammatory, or other infiltrates.

In another embodiment, hematopoietic stem or early progenitor cells comprise the cell populations used in this invention. In another embodiment, such populations are isolated or derived, by leukapheresis. In another embodiment, the leukapheresis follows cytokine administration, from bone marrow, peripheral blood (PB) or neonatal umbilical cord blood. In another embodiment, the stem or progenitor cells are characterized by their surface expression of the surface antigen marker known as $CD34^+$, and exclusion of expression of the surface lineage antigen markers, Lin−.

In another embodiment, the subject is administered a peptide, composition or vaccine of this invention, in conjunction with bone marrow cells. In another embodiment, the administration together with bone marrow cells embodiment follows previous irradiation of the subject, as part of the course of therapy, in order to suppress, inhibit or treat cancer in the subject.

In another embodiment, the phrase "contacting a cell" or "contacting a population" refers to a method of exposure, which can be, in other embodiments, direct or indirect. In another embodiment, such contact comprises direct injection of the cell through any means well known in the art, such as microinjection. It is also envisaged, in another embodiment, that supply to the cell is indirect, such as via provision in a culture medium that surrounds the cell, or administration to a subject, via any route well known in the art, and as described herein.

In another embodiment, CTL generation of methods of the present invention is accomplished in vivo, and is effected by introducing into a subject an antigen presenting cell contacted in vitro with a peptide of this invention (See for example Paglia et al. (1996) J. Exp. Med. 183:317-322).

In another embodiment, the peptides of methods and compositions of the present invention are delivered to APC. In another embodiment, the peptide-pulsed APC are administered to a subject to elicit and immune response or treat or inhibit growth or recurrence of a tumor. Each possibility represents a separate embodiment of the present invention.

In another embodiment, the peptides are delivered to APC in the form of cDNA encoding the peptides. In another embodiment, the term "antigen-presenting cells" (APC) refers to dendritic cells (DC), monocytes/macrophages, B lymphocytes or other cell type(s) expressing the necessary MHC/co-stimulatory molecules, which effectively allow for T cell recognition of the presented peptide. In another embodiment, the APC is a cancer cell. Each possibility represents a separate embodiment of the present invention.

In another embodiment, the CTL are contacted with 2 or more APC populations. In another embodiment, the 2 or more APC populations present different peptides. Each possibility represents a separate embodiment of the present invention.

In another embodiment, techniques that lead to the expression of antigen in the cytosol of APC (e.g. DC) are used to deliver the peptides to the APC. Methods for expressing antigens on APC are well known in the art. In another embodiment, the techniques include (1) the introduction into the APC of naked DNA encoding a peptide of this invention, (2) infection of APC with recombinant vectors expressing a peptide of this invention, and (3) introduction of a peptide of this invention into the cytosol of an APC using liposomes. (See Boczkowski D. et al. (1996) J. Exp. Med. 184:465-472; Rouse et al. (1994) J. Virol. 68:5685-5689; and Nair et al. (1992) J. Exp. Med. 175:609-612).

In another embodiment, foster APC such as those derived from the human cell line 174×CEM.T2, referred to as T2, which contains a mutation in its antigen processing pathway that restricts the association of endogenous peptides with cell surface MHC class I molecules (Zweerink et al. (1993) J. Immunol. 150:1763-1771), are used, as exemplified herein.

In another embodiment, as described herein, the subject is exposed to a peptide, or a composition/cell population comprising a peptide of this invention, which differs from the native protein expressed, wherein subsequently a host immune cross-reactive with the native protein/antigen develops.

In another embodiment, the subject, as referred to in any of the methods or embodiments of this invention is a human. In other embodiments, the subject is a mammal, which can be a mouse, rat, rabbit, hamster, guinea pig, horse, cow, sheep, goat, pig, cat, dog, monkey, or ape. Each possibility represents a separate embodiment of the present invention.

In another embodiment, peptides, vaccines, and compositions of this invention stimulate an immune response that results in tumor cell lysis.

In another embodiment, any of the methods described herein is used to elicit CTL, which are elicited in vitro. In another embodiment, the CTL are elicited ex-vivo. In another embodiment, the CTL are elicited in vitro. The resulting CTL, are, in another embodiment, administered to the subject, thereby treating the condition associated with the peptide, an expression product comprising the peptide, or a homologue thereof. Each possibility represents a separate embodiment of the present invention.

In another embodiment, the method entails introduction of the genetic sequence that encodes the peptides of this invention using, e.g., one or more nucleic acid delivery techniques. Nucleic acids of the invention include, in another embodiment, DNA, RNA and mixtures of DNA and RNA, alone or in conjunction with non-nucleic acid components. In another embodiment, the method comprises administering to the subject a vector comprising a nucleotide sequence, which encodes a peptide of the present invention (Tindle, R. W. et al. Virology (1994) 200:54). In another embodiment, the method comprises administering to the subject naked DNA which encodes a peptide, or in another embodiment, two or more peptides of this invention (Nabel, et al. PNAS-USA (1990) 90: 11307). In another embodiment, multi-epitope, analogue-based cancer vaccines are utilized (Fikes et al, Design of multi-epitope, analogue-based cancer vaccines. Expert Opin Biol Ther. 2003 September; 3(6):985-93). Each possibility represents a separate embodiment of the present invention.

Nucleic acids can be administered to a subject via any means as is known in the art, including parenteral or intravenous administration, or in another embodiment, by means of a gene gun. In another embodiment, the nucleic acids are administered in a composition, which correspond, in other embodiments, to any embodiment listed herein.

Vectors for use according to methods of this invention can comprise any vector that facilitates or allows for the expression of a peptide of this invention. Vectors comprise, in some embodiments, attenuated viruses, such as vaccinia or fowlpox, such as described in, e.g., U.S. Pat. No. 4,722,848, incorporated herein by reference. In another embodiment, the vector is BCG (Bacille Calmette Guerin), such as described in Stover et al. (Nature 351:456-460 (1991)). A wide variety of other vectors useful for therapeutic administration or immunization of the peptides of the invention, e.g., *Salmonella typhi* vectors and the like, will be apparent to those skilled in the art from the description herein.

In another embodiment, the vector further encodes for an immunomodulatory compound, as described herein. In another embodiment, the subject is administered an additional vector encoding same, concurrent, prior to or following administration of the vector encoding a peptide of this invention to the subject.

In another embodiment, the peptides, compositions and vaccines of this invention are administered to a subject, or utilized in the methods of this invention, in combination with other anticancer compounds and chemotherapeutics, including monoclonal antibodies directed against alternate cancer antigens, or, in another embodiment, epitopes that consist of an AA sequence which corresponds to, or in part to, that from which the peptides of this invention are derived.

Various embodiments of dosage ranges are contemplated by this invention. In another embodiment, the dosage is 20 µg per peptide per day. In another embodiment, the dosage is 10 µg/peptide/day. In another embodiment, the dosage is 30 µg/peptide/day. In another embodiment, the dosage is 40 µg/peptide/day. In another embodiment, the dosage is 60 µg/peptide/day. In another embodiment, the dosage is 80 µg/peptide/day. In another embodiment, the dosage is 100 µg/peptide/day. In another embodiment, the dosage is 150 µg/peptide/day. In another embodiment, the dosage is 200 µg/peptide/day. In another embodiment, the dosage is 300 µg/peptide/day. In another embodiment, the dosage is 400 µg/peptide/day. In another embodiment, the dosage is 600 µg/peptide/day. In another embodiment, the dosage is 800 µg/peptide/day. In another embodiment, the dosage is 1000 µg/peptide/day. In another embodiment, the dosage is 1500 µg/peptide/day. In another embodiment, the dosage is 2000 µg/peptide/day.

In another embodiment, the dosage is 10 µg/peptide/dose. In another embodiment, the dosage is 30 µg/peptide/dose. In another embodiment, the dosage is 40 µg/peptide/dose. In another embodiment, the dosage is 60 µg/peptide/dose. In another embodiment, the dosage is 80 µg/peptide/dose. In another embodiment, the dosage is 100 µg/peptide/dose. In another embodiment, the dosage is 150 µg/peptide/dose. In another embodiment, the dosage is 200 µg/peptide/dose. In another embodiment, the dosage is 300 µg/peptide/dose. In another embodiment, the dosage is 400 µg/peptide/dose. In another embodiment, the dosage is 600 µg/peptide/dose. In another embodiment, the dosage is 800 µg/peptide/dose. In another embodiment, the dosage is 1000 µg/peptide/dose. In another embodiment, the dosage is 1500 µg/peptide/dose. In another embodiment, the dosage is 2000 µg/peptide/dose.

In another embodiment, the dosage is 10-20 µg/peptide/dose. In another embodiment, the dosage is 20-30 µg/peptide/dose. In another embodiment, the dosage is 20-40 µg/peptide/dose. In another embodiment, the dosage is 30-60 µg/peptide/dose. In another embodiment, the dosage is 40-80 µg/peptide/dose. In another embodiment, the dosage is 50-100 µg/peptide/dose. In another embodiment, the dosage is 50-150 µg/peptide/dose. In another embodiment, the dosage is 100-200 µg/peptide/dose. In another embodiment, the dosage is 200-300 µg/peptide/dose. In another embodiment, the dosage is 300-400 µg/peptide/dose. In another embodiment, the dosage is 400-600 µg/peptide/dose. In another embodiment, the dosage is 500-800 µg/peptide/dose. In another embodiment, the dosage is 800-1000 µg/peptide/dose. In another embodiment, the dosage is 1000-1500 µg/peptide/dose. In another embodiment, the dosage is 1500-2000 µg/peptide/dose.

In another embodiment, the total amount of peptide per dose or per day is one of the above amounts. In another embodiment, the total peptide dose per dose is one of the above amounts.

Each of the above doses represents a separate embodiment of the present invention.

Various embodiments of dosage ranges are contemplated by this invention. In another embodiment, the dosage is 20 mg per peptide per day. In another embodiment, the dosage is 10 mg/peptide/day. In another embodiment, the dosage is 30 mg/peptide/day. In another embodiment, the dosage is 40 mg/peptide/day. In another embodiment, the dosage is 60 mg/peptide/day. In another embodiment, the dosage is 80 mg/peptide/day. In another embodiment, the dosage is 100 mg/peptide/day. In another embodiment, the dosage is 150 mg/peptide/day. In another embodiment, the dosage is 200 mg/peptide/day. In another embodiment, the dosage is 300 mg/peptide/day. In another embodiment, the dosage is 400 mg/peptide/day. In another embodiment, the dosage is 600 mg/peptide/day. In another embodiment, the dosage is 800 mg/peptide/day. In another embodiment, the dosage is 1000 mg/peptide/day.

In another embodiment, the dosage is 10 mg/peptide/dose. In another embodiment, the dosage is 30 mg/peptide/dose. In another embodiment, the dosage is 40 mg/peptide/dose. In another embodiment, the dosage is 60 mg/peptide/dose. In another embodiment, the dosage is 80 mg/peptide/dose. In another embodiment, the dosage is 100 mg/peptide/dose. In another embodiment, the dosage is 150 mg/peptide/dose. In another embodiment, the dosage is 200 mg/peptide/dose. In another embodiment, the dosage is 300 mg/peptide/dose. In another embodiment, the dosage is 400 mg/peptide/dose. In another embodiment, the dosage is 600 mg/peptide/dose. In another embodiment, the dosage is 800 mg/peptide/dose. In another embodiment, the dosage is 1000 mg/peptide/dose.

In another embodiment, the dosage is 10-20 mg/peptide/dose. In another embodiment, the dosage is 20-30 mg/peptide/dose. In another embodiment, the dosage is 20-40 mg/peptide/dose. In another embodiment, the dosage is 30-60 mg/peptide/dose. In another embodiment, the dosage is 40-80 mg/peptide/dose. In another embodiment, the dosage is 50-100 mg/peptide/dose. In another embodiment, the dosage is 50-150 mg/peptide/dose. In another embodiment, the dosage is 100-200 mg/peptide/dose. In another embodiment, the dosage is 200-300 mg/peptide/dose. In another embodiment, the dosage is 300-400 mg/peptide/dose. In another embodiment, the dosage is 400-600 mg/peptide/dose. In another embodiment, the dosage is 500-800 mg/peptide/dose. In another embodiment, the dosage is 800-1000 mg/peptide/dose.

In another embodiment, the total amount of peptide per dose or per day is one of the above amounts. In another embodiment, the total peptide dose per dose is one of the above amounts.

Each of the above doses represents a separate embodiment of the present invention.

In another embodiment, the present invention provides a kit comprising a peptide, composition or vaccine of the present invention. In another embodiment, the kit further comprises a label or packaging insert. In another embodiment, the kit is used for detecting a WT1-specific CD4 response through the use of a delayed-type hypersensitivity test. In another embodiment, the kit is used for any other method enumerated herein. In another embodiment, the kit is used for any other method known in the art. Each possibility represents a separate embodiment of the present invention.

Among those antigens uniquely or differentially expressed by malignant cells, WT1 is considered one of the most promising (47). However, the number of immunogenic WT1 peptide antigens previously identified and reported is very limited, and largely confined to a set of peptides presented by the HLA alleles A0201, A2402 and DRB10401. As will be seen from the examples presented below, using a pool of overlapping 15-mer peptides spanning the amino acid sequence of WT1 loaded on autologous APCs for sensitization, WT1 peptide-specific IFNγ+CD4+ and CD8 T-cell responses were generated from the blood of 41/56 (78%) normal donors, and thereafter the epitopes eliciting these responses and their presenting HLA alleles were identified. Of the 42 WT1 peptide antigens described, all but one have not been heretofore identified. The new immunogenic peptides identified include 36 peptides presented by class I HLA alleles and 5 presented by class II HLA alleles. Of the peptides presented by class I HLA alleles, 10 nonamer epitopes were identified which could be presented by from 2-4 different HLA alleles. Also identified, within 4 pentadecapeptides, were overlapping 11-mer and nonamer sequences that co-induced distinguishable CD4+ IFNγ+ and CD8+ IFNγ+ T-cells. Whether and to what degree epitopes that can be presented by more than one allele can elicit enhanced WT1 specific responses in individuals inheriting both presenting HLA alleles or both the class I and class II presenting HLA alleles in those instances in which overlapping sequences are contained in the same 15-mer is readily determinable; however, inclusion of such peptides in WT1 vaccines could significantly broaden their applicability particularly among patients not inheriting HLA-A0201 or A2402.

As shown in the examples, those peptides presented by class I HLA alleles elicited IFNγ+CD8+ T-cells that were able to lyse peptide loaded autologous APCs as well as allogeneic APCs sharing the T-cells' restricting HLA allele in 50/51 (99%) and 48/51 (94%)cultures tested respectively (Table 1, 2). More importantly, of 36 HLA-restricted WT1 peptide specific T-cell lines that could be tested, T-cell lines specific for 29 epitopes including 2/4 epitopes presented by class II and 27/32 presented by class I alleles, were also able to lyse WT1+ leukemic blasts sharing the T-cells' restricting HLA allele. The failure of the HLA-restricted WT1 epitope-specific T-cells to lyse allogeneic PHA blasts from the same leukemic patients (Table 3A), coupled with the differential leukemocidal activity of T-cells sensitized with WT1 peptide-loaded autologous EBVBLCL when compared to aliquots of the same T-cells sensitized with autologous EBVBLCL alone (Table 3B) indicates that the leukemocidal activity is WT1 peptide-specific and not a result of contaminating alloreactive T-cells. Thus, these data show that 29/36 immunogenic peptides of WT1 identified (80%) can be processed and presented by WT1+ leukemic cells at concentrations adequate for WT1 epitope-specific T-cell recognition and cytolysis.

In FIG. 4, maps are shown of the WT1 protein. FIG. 4C defines the localization of all previously reported antigenic epitopes presented by HLA class I and II alleles; FIG. 4D depicts the location of immunogenic peptides identified in this report. As can be seen, the 11 epitopes previously reported to be presented by class I and 10 presented by class II HLA alleles are principally clustered in sequences encoded by exons 1, 7 and 10, while the epitopes recognized by normal T-cells sensitized with the WT1 peptide pool are principally clustered in sequences encoded by the first 5 exons. Thus, 26 of the new epitopes are included in each of the four major isoforms of WT1 resulting from splice variants that do or do not include the 17 amino acid sequence (aas 250-266) in exon 5 or the three amino acid sequence ($_{400-410}$KTS) between zinc fingers 3 and 4. While the epitopes are broadly distributed, clusters of epitopes were detected in the RNA recognition domain in exon 1 and the activation domain (aa 181-250) (FIG. 4F) proximal to the spliced 17aa segment in exon 5. The latter area also contained those epitopes most frequently recognized by multiple donors (FIG. 4E). Interestingly, 9 newly identified epitopes map to a 126 amino acid sequence at the N terminus encoded by a segment of the WT1 gene initially described by Gessler et al (37) that is centromeric to exon 1 of the (Exon 5+, KTS+) isoform of WT1 and includes the long isoform of WT1 initiated at a CUG codon upstream of the AUG initiator for exon 1.50 Strikingly, each of the epitopes identified in this sequence elicits IFNγ+ T-cells that are cytolytic against leukemic blasts coexpressing WT1 and the T-cells' restricting HLA allele.

Of the several "self" proteins such as WT1, NY-ESO-1, HER2/neu, MAGE, and others, differentially expressed by specific tumors, only WT1 and MART-1 have been shown to elicit responses in normal donors (31,32,51-54). In contrast, T-cells specific for each of these proteins have been recorded in a proportion of patients with tumors overexpressing them (55). In particular, T-cells specific for the RMF and CMT peptides of WT1 have been detected in patients with leukemias, myeloma, carcinoma of the breast and prostate and other solid tumors (31,32,56-61). Responses to several of the WT1 epitopes identified in the present study in 50-60% of patients with ovarian cancer have been documented. Given the high number of potentially immunogenic epitopes in proteins such as NY-ESO-1 and HER2/neu that have elicited responses in tumor-bearing hosts (62), the number of immunogenic WT1 peptides we have identified is not sufficiently different to account for the differential presence of WT1 responses in normal donors. Furthermore, Pospori et al (63) have shown that HSCs expressing a transduced TCR specific for a WT1 peptide presented by HLA-A0201 are not deleted in the thymus of HLA-A0201 transgenic mice and generate functional memory T-cells. However, while the basis for this lack of "self" tolerance is unclear, the studies of Rezvani et al (31) and data herein (FIG. 1A) indicate that the frequencies of WT1 specific T-cells in the blood of healthy donors is low. In part, this may reflect the low levels and limited tissue distribution of WT1 expression in normal individuals (18-20). Recently, Rezvani et al (64) also demonstrated declining T-cell responses to WT1 in patients repeatedly vaccinated with WT1 peptides, suggesting that these responses are highly regulated. Lehe et al (65) have also recently shown that sensitization of T-cells with a WT1 peptide presented by DRB10402 in the presence of high concentrations of IL-2 preferentially stimulates the generation of CD25+ FOX P3+ GITR+CD127-regulatory T-cells capable of inhibiting CD8+WT1 specific T-cell responses.

Under the culture conditions employed herein, autologous DCs and EBVBLCL loaded with the WT1 peptide pool preferentially induced the generation of CD8+ and CD4+ IFNγ+WT1 peptide-specific T-cells from 41/56 normal donors (73%). Although each donor recognized only 1-3 epitopes of WT1, the fact that T-cells specific for 80% of these epitopes could recognize WT1+ leukemic cells sharing the T-cells' presenting HLA allele suggests that the turnover and processing of the aberrantly expressed WT1 is high, permitting the simultaneous presentation of several different WT1 epitopes by the restricting HLA allele expressed by these leukemic cells. Identification of these epitopes is useful both for in vitro generation of potent tumoricidal WT1 specific T-cells for adoptive cell therapies and for the generation of more broadly applicable vaccines for stimulating T-cell responses for eradication of clonogenic tumor cells expressing WT1 in vivo.

In one embodiment, peptides from the WT1 protein sequence that are upstream from exon 1, i.e., within the first 126 amino acids of SEQ ID NO:194, are heretofore unrecognized sites of immunogenic epitopes and therefore peptides useful for the purposes herein.

EXAMPLE 1

Binding of HLA-A0201 and -A0301 by Synthetic Peptide Analogues Derived from WT1

Materials and Experimental Methods. Peptides were synthesized by Genemed Synthesis Inc, CA using fluorenyl-methoxycarbonyl chemistry and solid phase synthesis, and were purified by high pressure liquid chromatography (HPLC). The quality of the peptides was assessed by HPLC analysis, and the expected molecular weight was measured using matrix-assisted laser desorption mass spectrometry. Peptides were sterile and >90% pure. The peptides were dissolved in DMSO and diluted in PBS at pH 7.4 or saline solution to yield a concentration of 5 milligrams per milliliter (mg/ml) and were stored at −80° C. For in vitro experiments, an irrelevant control peptide, HLA A24 consensus, was used.

Peptide sequence analysis. Peptide sequence analysis was performed using 2 databases. The first was the software of the Bioinformatics & Molecular Analysis Section (National Institutes of Health, Washington, D.C.) (Parker K C et al, Scheme for ranking potential HLA-A2 binding peptides based on independent binding of individual peptide sidechains. J Immunol 152: 163-175, 1994), which ranks 9-mer or 10-mer peptides on a predicted half-time dissociation coefficient from HLA class I molecules. The second database, SYFPEITHI prediction software, is described in Rammensee H G et al (SYFPEITHI: database for MHC ligands and peptide motifs. Immunogenetics 50: 213-219, 1999). Irrelevant control peptides used in in vitro experiments were: RAS (TEYKLVVVGAPGVGKSALTIQ; SEQ ID No: 198) or CML b2a2 (VHSIPLTINKEEALQRPVASDFE; SEQ ID No: 199) for Class II, and HIV pol (ILKEPVHGV; SEQ ID No: 200) or CML F (YLKALQRPY; SEQ ID No: 201) for Class I.

Cell lines. Cell lines were cultured in RPMI 1640 medium supplemented with 5% FCS, penicillin, streptomycin, 2 mM glutamine and 2-mercaptoethanol at 37° C. in humidified air containing 5% CO2. T2 is a human cell line lacking TAP1 and TAP2 and therefore unable to present peptides derived from cytosolic proteins. Raji cells are a human Burkitt lymphoma cells that exhibit a high level of TAP expression.

Human mesothelioma cell lines studied included: sarcomatoid (VAMT, H2373, H28), epithelioid (H2452) and biphasic (JMN, MSTO and H-Meso1A). Cell lines were obtained from the following sources: H-Meso1A: NCI, Bethesda, Md.; JMN and VAMT: Dr. Sirotnak, Memorial Sloan Kettering Cancer Center (MSKCC); H-2452 and H2373: Dr. Pass, Karmanos Cancer Institute, Wayne State University, Detroit, Mich.; H28 and MSTO: American Type Culture Collection (ATCC, Manassas, Va.). Cell lines were maintained in media recommended by the suppliers and incubated in a humidified incubator with 5% CO2.

Mesothelioma cell lines Meso 11, Meso 34, Meso 37, Meso 47 and Meso 56 were obtained from Dr. M Gregoire (Institute of Biology, Nantes, France) and cultured in RPMI 1640 (Life Technologies)+10% fetal calf serum (FCS), 1% penicillin—streptomycin, and 1% L-glutamine. All cells were HLA typed by the Department of Cellular Immunology at MSKCC. Melanoma cell line Mewo (WT1− A201+) was obtained from the ATCC. SKRC-52 renal cell carcinoma was obtained from L. Old of the Ludwig Institute. Leukemia cell lines were cultured in RPMI 1640+10% FCS, 1% penicillin-streptomycin, 2 mM glutamine and 2-mercaptoethanol at 37oC/5% CO2. LAMA81, BV173 and 697, Ph+ leukemias that are all WT1+ and A0201+, were provided by Dr. HJ Stauss (University College London). SKLY-16 is a human B cell lymphoma (WT1−, A0201+); K562, RwLeu4 and HL60, all WT1+ leukemias, were obtained from the ATCC.

T2 assay for peptide binding and stabilization of HLA A0201 molecules. T2 cells (TAP−, HLA-A0201$^+$) were incubated overnight at 27° C. at a concentration of 1×10$^6$ cells/ml in FCS-free RPMI medium supplemented with 5 μg/ml human $\beta_{2m}$ (Sigma, St Louis, Mo.) in the absence (negative control) or presence of either a positive reference tyrosinase peptide or test peptides at various final concentrations (50, 10, 1, and 0.1 micrograms (μg)/ml). Following a 4-hour incubation with 5 μg/ml brefeldin A (Sigma), T2 cells were labeled for 30 minutes at 4° C. with a saturating concentration of anti-HLA-A2.1 (BB7.2) mAb, then washed twice. Cells were then incubated for 30 minutes, 4° C. with a saturating concentration of FITC-conjugated goat IgG F(ab')2 anti-mouse Ig (Caltag, San Francisco, Calif.), washed twice, fixed in PBS/1% paraformaldehyde and analyzed using a FACS Calibur® cytofluorometer (Becton Dickinson, Immunocytometry Systems, San Jose, Calif.).

The mean intensity of fluorescence (MIF) observed for each peptide concentration (after dividing by the MIF in the absence of peptide) was used as an indication of peptide binding and expressed as a "fluorescence index." Stabilization assays were performed similarly. Following initial evaluation of peptide binding at time 0, cells were washed in RPMI complete medium to remove free peptides and incubated in the continuous presence of 0.5 μg/ml brefeldin-A for 2, 4, 6 or 8 hours.

The number of stable peptide-HLA-A2.1 complexes was estimated as described above by immunofluorescence. The half time of complexes is an estimate of the time required for a 50% reduction of the MIF value at time=0.

WT1 peptides. The sequence of the WT1 protein published by Gessler et al. (37) which comprises 575 aminoacids and includes the first 126 aminoacids in the N-terminus missing in the (Exon 5+, KTS+) isoform of WT116, was used to design the peptide sequences (SEQ ID NO:194; FIG. 2A). 141 pentadecapeptides spanning this sequence, each overlapping the next by 11aa, were synthesized by Invitrogen (Baltimore, Md.) to specifications of validated sequence, 95% purity, sterility and absence of endotoxin. These 141 15-mers were mixed in equal amounts to form a total pool of peptides, in which each peptide is at a concentration of 0.35 mcg/ml. This pool was used for the T-cell sensitization. To identify peptides eliciting responses, subpools containing 12 pentadecapeptides (4.17 mcg/ml/peptide) were established to form a mapping matrix in which each peptide is included in only two overlapping subpools (FIG. 2B).

Generation of WT1 specific T-cells: Peripheral blood was obtained from 56 consenting normal donors according to protocols approved by the Institutional Review Board of Memorial Sloan-Kettering Cancer Center (New York, N.Y.). All donors were typed for HLA-A, B, C, DR and DQ at high resolution by standard techniques.

Cytokine-activated monocytes (CAMs) were used as antigen presenting cells (APCs), and generated as previously described (32). Briefly, peripheral blood monocytes were separated by adherence on plastic and cultured in RPMI1640 containing 1% autologous serum. GM-CSF (Berlex, Montville, N.J.) and interleukin-4 (IL-4) (R&D Systems, Minneapolis, Minn.) were added to final concentrations of 2000 U/ml and 1000 U/ml respectively on days 0, 2, 4. On day 5, these cells were additionally treated with TNFα (10 ng/ml), interleukin-6 (IL-6) (1000 IU/ml), IL1β (400 IU/ml), PGE2 (25 mM-3) (R&D Systems, Minneapolis, Minn.) together with GM-CSF and IL-4 at the same doses. CAMs harvested on day 7 of culture expressed CD83, CD80, CD86, and HLA class I and II alleles as determined by FACS analysis.

EBV-BLCL were also used as WT1 peptide loaded and control APCs or as targets as specified in the experiments. They were generated by infection of peripheral blood mononuclear cells (PBMC) with EBV strain B95.8 (38,39) as previously described. The EBV transformed BLCL (EBV-BLCL) were cultured in RPMI1640(Gemini) with 10% fetal calf serum (Gemini) in the presence of Acyclovir.

Sensitization and propagation of WT1 specific T-cells. To generate WT1-specific CTLs, PBMC were isolated by Ficoll-Hypaque density gradient centrifugation. Monocytes were depleted by adherence on plastic and NK cells by absorption to immunomagnetic CD56 pre-coated microbeads (Miltenyi Biotech Inc, MA) as previously described (32). Enriched T-cell fractions were stimulated at a 20:1 responder:stimulator ratio with autologous CAMs or EBV-BLCL that had been pre-loaded for 3 hours with the total pool of the WT1 pentadecapeptides in serum-free medium and irradiated to 3000 cGy. T-cells were cultured in Yssel's medium supplemented with 5% AB human serum (YHS, Gemini), re-stimulated weekly with the autologous WT1 total pool-loaded CAMs or EBV-BLCL and fed with inter-leukin-2(IL-2) (Collaborative Biomedical Products, Bedford, Mass.) every 2-3 days at 10-50 U/ml.

Cell targets—leukemic cells: Twenty-four primary leukemic cells and 1 leukemic cell line were characterized for their expression of WT1 by intracellular FACS staining using murine anti-human WT1 monoclonal antibodies (Neomarkers, Fremont, Calif.) as previously described (32,38) The WT1+ leukemias included blast cells from 11 primary AMLs, 3 primary ALLs and 1 B-cell precursor ALL cell line. Ten WT1− leukemias, were used as controls, and included 3 B-cell precursor ALLs and 7 AMLs.

All EBV BLCL and leukemia cells were typed for HLA A, B, C, DR and DQ alleles at high resolution by standard techniques.

Assessment of T-Cell Response.

IFNγ production by WT1 specific T-cells. The proportion and phenotype (CD4 and CD8) of T-cells generating IFNγ in response to secondary stimulation with the WT1 total pool, WT1 subpools or single WT1 15-mer or 9-mer WT1 peptides loaded on autologous PBMC were measured by FACS analysis of T-cells containing intracellular IFNγ as previously described (38,40).

Mapping of timmunogenic epiopes. Aliquots of the T-cells stimulated with the WT1 total pool for 35-42 days were washed and re-stimulated overnight with autologous PBMC loaded with one of each of the subpools of WT1 pentadecapeptides. T-cell responses to each subpool were quantitated by FACS analysis of T-cells bearing intracellular IFNγ as previously described (41). The mapping grid (FIG. 2B) was then used to identify specific WT1 15-mers uniquely shared by 2 subpools eliciting T-cell responses. These 15-mers and 9-mer or 11-mer sequences within the 15-mers were then analyzed as secondary single peptide stimulators to confirm their immunogenicity and define the immunogenic epitope(s) within the 15-mer eliciting responses.

Cytotoxic activity. The W-1-specific and HLA-restricted cytotoxic activity of sensitized T-cells was measured in standard Cr51 release assays against a panel of HLA-matched and mismatched CAM targets either unmodified or loaded with the total pool, the identified 15-mer, or the 9-mer or 11-mer epitope of WT1 eliciting T-cell responses, as previously described (32). In addition, the restricting HLA allele presenting each immunogenic epitope was identified by measuring the cytotoxicity of the sensitized T-cells against a panel of allogeneic CAMs pre-loaded with the peptide, each sharing a single HLA allele expressed on the responding WT1-specific T-cells as previously described (41). The cytotoxic activity of the WT1 epitope-specific CTLs against WT1− and WT1+ leukemia cell lines or primary leukemic cells expressing the restricting HLA alleles was also assessed in this cytotoxicity assay Cr51 assay as previously described (32).

Immunogenicity of the identified immunodominant WT1 derived epitopes. To estimate the immunogenicity of identified WT1 peptide epitopes in different individuals, enriched T-cells separated from PBMC of groups of normal donors expressing one of a series of prevalent HLA alleles (i.e. HLA-A0201, A0301, A2402, B0702) which were previously identified as a presenter of a newly identified WT1 epitope were sensitized in vitro with artificial antigen-presenting cells (AAPC) (42) expressing that HLA allele and loaded with the pre-identified WT1 epitope or an irrelevant peptide. The panel of AAPCs includes AAPCs expressing one of the following single HLA alleles: HLA A0201, A0101, A0301, A2402, B0702 or B0801, which were generated as previously described (42). After 35 days of co-culture of T-cells with the peptide-loaded AAPCs in the presence of IL2, CTLs were secondarily stimulated overnight with autologous PBMC loaded with the sensitizing peptide or an unrelated peptide and tested for their IFNγ response. The responses were registered as positive if the proportion of T-cells producing IFNγ in response to the secondary stimulation with autologous PBMC loaded with the stimulating WT1 derived peptide exceeded the background proportion of IFNγ T-cells incubated with PBMC alone by two fold or more.

EXAMPLE 2

Responses of Normal Donors to the WT1 Total Pool of Pentadecapeptides

Frequencies of WT1-specific IFNγ+ T-cells in the PBMC of 41 normal donors were measured initially. These frequencies ranged between 0.01% to 1.82%, and exceeded the background of IFNγ+ T-cells detected in T-cells stimulated with autologous PBMC alone in only 10/41 individuals (FIG. 1A). In vitro sensitization of T-cells from 56 normal donors with autologous CAMs loaded with the total pool of WT1 pentadecapeptides for periods of 35-42 days resulted in significant expansion of IFNγ+ T-cells in 41/56 cases (73%) (FIG. 1A). T-cells generated from 38/56 donors also exhibited cytotoxic activity against autologous PHA blasts loaded with the WT1 total pool (FIG. 1B), including T-cells from 38 of the 41 donors that produced IFNγ in response to secondary stimulation with the WT1 peptide pool.

The capacity of one of the previously reported WT1 epitopes predicted to bind the HLA-A0201 allele, $_{126\text{-}134}$RMFPNAPYL (SEQ ID NO:161; RMF) (43) were compared with the total pool of WT1 pentadecapeptides to stimulate WT1 reactive T-cells in HLA-A0201+ normal donors (n=14) when loaded on autologous CAMs. Increased frequencies of IFNγ+ T-cells initially sensitized with the RMF peptide were detected in 9/14 donors, 7 of whom also responded to secondary simulation with the pooled peptides (FIG. 1C). In contrast, 12/14 CTL lines initially sensitized with the WT1 peptide pool, generated high frequencies of IFNγ+ T-cells after secondary stimulation with the WT1 total pool, including 6 CTL lines that also responded to RMF. The epitopes of WT1 recognized by the T-cells sensitized with the total pool (vide infra) were mapped and epitopes other than RMF in 12/14 donors were identified. The magnitude of the responses to those epitopes was much higher than to the RMF peptide (FIG. 1C). Only 4/14 CTL lines initially sensitized with RMF exhibited cytotoxic activity against RMF-loaded autologous PHA blasts; of which 3 could also lyse autologous PHA blasts loaded with the WT1pool (FIG. 1D). In contrast, 10/14 CTL sensitized with the pool of WT1 peptides were cytotoxic against PHA blasts loaded with the WT1 total pool including 3/14 that lysed RMF peptide loaded blasts (FIG. 1D). Thus, in a high proportion of HLA A0201+ donors, stimulation of T-cells with the WT1 total pool more consistently elicited WT1-specific T-cell responses than stimulation with the single HLA A0201 binding RMF peptide.

Detailed description of FIG. 1. WT1 specific responses of CTL generated from PBMC of normal donors (n=56) by stimulation with autologous APCs loaded with total pool of WT1 derived pentadecapeptides: A. production of IFNγ in PBMC alone (as a background), PBMC co-incubated overnight with the total pool of pentadecapeptides spanning the whole sequence of WT1 protein (PBMC+WT1 pool) and pre-generated WT1 specific T cells co-incubated overnight with WT1 peptide loaded PBMC; B. cytotoxic activity of the WT1 specific CTLs generated in vitro by stimulation with WT1 total pool against WT1- (autologous PHA stimulated blasts) and WT1+(autologous PHA stimulated blasts loaded with the total pool of WT1 pentadecapeptides) targets at 50:1 effector:stimulator ratio; C. IFNγ response measured by FACS staining in different responder cell populations (peripheral blood derived PBMC, pre-generated CTLs sensitized in vitro with the RMF peptide loaded on autologous CAM and pre-generated CTLs sensitized with the total pool of WT1 15-mers) after secondary overnight stimulation with autologous PBMC either unmodified or loaded with one of the following: RMF peptide, dominant epitopes of WT1 identified by the epitope mapping approach in the WT1-total pool sensitized CTL, WT1 total pool of the 141 pentadecapeptides; D. Cytotoxic activity of the WT specific T cells generated in vitro by sensitization with autologous CAMs loaded with the RMF 9-mer or with the total pool of the WT1 15-mers. The cytotoxicity of the T cells was assessed against autologous WT1 negative targets(PHA activated blasts) and the same targets loaded with RMF peptide, the total pool of WT1 15-mers or the dominant WT1 epitope identified for the same T cell line.

EXAMPLE 3

Identification of Immunogenic Epitopes of WT1 Protein Recognized by the WT1-Reactive T-Cells WT1 CTLs generated by sensitization with the pooled peptides are epitope specific and HLA restricted. The epitopes recognized by T-cells sensitized in vitro with the total pool of overlapping WT1 pentadecapeptides (FIG. 2A) were identified by quantitating IFNγ+ T-cells responding to a mapping grid of subpools of WT1 15-mers formed so that any single 15-mer is shared by only 2 intersecting subpools (FIG. 2B). As shown for a representative example in FIG. 2C, significantly increased numbers of IFNγ+ T-cells are selectively generated in response to subpools #3 and #19 which share the pentadecapeptide #75. The T-cells were then stimulated with neighboring 15-mers, each overlapping peptide #75 by 11aa. As can be seen, IFNγ+ T-cells are selectively generated in response to peptide #75 (FIG. 2D). The newly identified immunogenic WT1 epitope is $_{174\text{-}182}$HSFKHEDPM. Subsequently, the cytotoxic activity of these T-cells was assessed against a panel of allogeneic CAMs either unmodified or loaded with this peptide, each sharing one HLA allele expressed by the tested CTLs. As shown in FIG. 2E, the T-cells selectively lysed peptide loaded autologous targets and targets expressing the HLA-B3501 allele, and did not lyse peptide-loaded targets sharing other HLA alleles inherited by the T-cell donor. These T-cells also lysed WT1+ BALL cells coexpressing the HLA-B3501 allele.

Detailed description of FIG. 2. Strategy for the generation of the total pool of overlapping pentadecapeptides spanning the whole sequence of the WT1 protein and epitope mapping: A. The sequence of the WT1 protein consisting of 575 amino acids and the principle of 11 amino acid overlapping pentadecapeptides are illustrated. A total of 141 pentadecapeptides are required to span the entire protein. The sequence of 575 aminoacids published by Gessler et al. (37), was employed. This sequence includes an additional 126 aminoacids in the N-terminus. In order to match the sequential numbers of aminoacids within the WT1 sequence used with the longest, most frequently described WT1 isoform D we numbered the first 126aa with negative values and used the positive values to number the subsequent 449 aminoacids described in the longest isoform D; B. The mapping grid consisting of 24 subpools each containing up to 12 WT1-derived pentadecapeptides. Each peptide is uniquely contained within two intersecting subpools: for example peptide 75 is uniquely shared by subpools 3 and 19; C. IFNγ production by WT1 sensitized CTLs in response to secondary overnight stimulation with the subpools of WT1 pentadecapeptides loaded on autologous PBMC. Dominant responses are observed for the subpools #3 and #19 both containing one common pentadecapeptide #75; D. IFNγ production by the WT1 CTLs in response to secondary overnight stimulation with the single pentadecapeptide contained within the subpools eliciting the highest responses as per the analysis determined in 2C of this figure confirms that the dominant immunogenic sequence is contained within pentadecapeptide #75; E. HLA restriction of the WT1 specific T cells responding to peptide #75 identified by Cr51 release assay against a panel of allogeneic CAMs or PHA blasts matching single HLA alleles expressed by the WT1 CTL donors. These are presented along the X axis of the graph. The CAMs or PHA blasts used in the assay are unmodified (grey bars) or loaded with the WT1 dominant epitope (black bars). The WT1 specific cytotoxic activity of the WT1 CTLs is restricted by the B3501 HLA allele.

Mapping of WT1 peptides eliciting T-cell responses identifies a diversity of immunogenic epitopes presented by different class I and II HLA alleles. The same approach was used to map and ultimately identify WT1 epitopes eliciting responses by T-cells from the other 40 responding normal donors. Of these donors, 8 (19%) responded exclusively to one WT1 peptide, while 18 (43%) responded to two and 16

(39%) to 3 peptides. In cultures eliciting responses to more than one WT-1 peptide, the patterns of IFNγ+ T-cell responses to the subpools were sufficiently distinctive to permit initial segregation of potentially immunogenic peptides. Each candidate peptide was then evaluated individually to ascertain the specific peptide inducing a T-cell response.

The immunogenic peptides of WT1 that were identified and their presenting HLA alleles are listed in Table 1. Of the 42 WT1 peptides eliciting T-cell responses, 41 are newly identified; only one of these WT1 peptides, the $_{126-134}$RMFPNAPYL nonamer presented by HLA-A0201, has been previously described and shown to be immunogenic when presented by this allele (43) Peptide 91, $_{235-249}$CMTWNQMNLGATLKG contains an epitope which, in the study, elicited CD4+ T-cell responses restricted by HLA DRB1 0402, but also contains the 235-243CMT nonamer known to be presented by HLA A0201 and HLA A2402 (29). For 26 of the peptides presented by class I HLA alleles, a single presenting HLA allele was identified in the initially studied donor. However, when the HLA-restrictions of T-cells responding to these peptides in different donors was examined, 10 of these peptides were found that could elicit T-cell responses when presented by 2 or 3 different class I HLA alleles. One sequence, the $_{238-246}$WNQMNL-GAT peptide, elicited strong IFNγ+CD8+ T-cell responses when presented in different donors by any one of 4 distinct HLA class I alleles.

TABLE 1

WT1 derived immunogenic epitopes identified by IFNγ production assay for T cells responses using pool of overlapping pentadecapeptides spanning the whole sequence of WT1protein. Bolded peptide sequences represent those tested in Example 5 and results shown in Table 3.

| 15-mer number (SEQ ID, Table IV) Containing the dominant epitope | Sequence identified | Presenting HLA allele | IFNg response of cells, % IFNg + cells | | Cytotoxic CTL response, % (at 50:1) E:T ratio vs WT1 peptide loaded | | |
|---|---|---|---|---|---|---|---|
| | | | No WT1 peptide | WT1 peptide loaded | WT1- Autologous APC | WT1- autologous APC | WT1 − leukemia | WT1 + leukemia |
| #1 | (−125)-(−117) RQRPHPGAL (SEQ ID NO: 142) | B0702 | 0.9 | 11.3 | 0 | 27 | 1 | 67 |
| #2 | (−119)-(−111) GALRNPTAC (SEQ ID NO: 143) | B0702 | 0.5 | 14.0 | 0 | 30 | 1 | 60 |
| #4 | (−110)-(−102) PLPHFPPSL (SEQ ID NO: 144) | A0201 | 0.98 | 5.75 | 0 | 30 | 2 | 22 |
| #5 | (−107)-(−99) HFPPSLPPT (SEQ ID NO: 145) | A3101 | 0.73 | 4.82 | 0 | 42 | ND | ND |
| #7 **** | (−99)-(−91) THSPTHPPR (SEQ ID NO: 146) | B4001 A0201 | 1.5 0.4 | 12.8 5 | 0 2 | 45 50 | 3 0 | 65 38 |
| #13 | (−75)-(−67) AILDFLLLQ (SEQ ID NO: 147) | A0201 | 0.61 | 5.07 | 0 | 18 | 3 | 19 |
| #20 ** | (−47)-(−39) PGCLQQPEQ** (SEQ ID NO: 148) (−47)-(−37) PGCLQQPEQQG (SEQ ID NO: 149) | A0201 B4701 DRB10101 | 0.2 0.5 0.33 | 3.67 4.6 3.1 | 6 6 6 | 54 54 54 | 5 ND ND | 19 ND ND |
| #24-25 | (−27)-(−19) KLGAAEASA (SEQ ID NO: 150) | A0201 | 1.05 | 4.48 | 3 | 41 | 10 | 37 |
| #29-30 | (−8)-(1) ASGSEPQQM (SEQ ID NO: 151) | B3501 | 0.07 | 1.0 | 5 | 73 | 5 | 39 |
| #33 **** | 6-15 RDLNALLPAV** (SEQ ID NO: 152) | A0201 B5701 | 1.1 0.19 | 11.0 1.24 | 2 3 | 51 44 | 0 ND | 9 ND |
| #37 | 22-31 GGCALPVSGA (SEQ ID NO: 153) | A0201 | 0.07 | 0.9 | 8 | 32 | 3 | 47 |

TABLE 1-continued

WT1 derived immunogenic epitopes identified by IFNγ production
assay for T cells responses using pool of overlapping pentadecapeptides spanning the whole
sequence of WT1protein. Bolded peptide sequences represent those tested in Example 5 and
results shown in Table 3.

| 15-mer number (SEQ ID, Table IV) Containing the dominant epitope | Sequence identified | Presenting HLA allele | IFNg response of cells, % IFNg + cells | | Cytotoxic CTL response, % (at 50:1) E:T ratio vs | | | |
|---|---|---|---|---|---|---|---|---|
| | | | No WT1 peptide | WT1 peptide loaded | WT1- Autologous APC | WT1 peptide loaded autologous APC | WT1 - leukemia | WT1 + leukemia |
| #39 | 30-38 GAAQWAPVL (SEQ ID NO: 154) | B3901 | 0.1 | 1.3 | 2 | 31 | ND | ND |
| #41 ** | 38-46 LDFAPPGAS** (SEQ ID NO: 155) | A0201 | 0.2 | 4.18 | 0 | 73 | 0 | 40 |
| | 38-48 LDFAPPGASAY (SEQ ID NO: 156) | DRB10402 | 0.2 | 1.41 | 0 | 73 | 0 | 40 |
| #43 **** | 46-54 SAYGSLGGP* (SEQ ID NO: 157)* | A0201 B4001 | 1.2 1.09 | 6.46 6.84 | 2 2 | 51 41 | 0 3 | 0 68 |
| #46 | 58-66 PAPPPPPPP** (SEQ ID NO: 158) | A0201 | 1.15 | 6.69 | 2 | 40 | 0 | 0 |
| #58 | 106-114 ACRYGPFGP (SEQ ID NO: 159) | B4402 | 0.92 | 5.65 | 8 | 46 | ND | ND |
| #62 **** | 122-130 SGQARMFPN*** (SEQ ID NO: 160) | B3503 C0401 | 0.78 0.78 | 2.0 2.0 | 0 0 | 84 84 | ND ND | ND ND |
| #62-63 | 126-134 RMFPNAPYL* (SEQ ID NO: 161) | A0201 | 0.52 | 2.17 | 3 | 41 | 2 | 25 |
| #65-66 | 135-143 PSCLESQPA (SEQ ID NO: 162) | B3501 | 0.07 | 0.61 | 0 | 35 | ND | ND |
| #68 | 146-154 NQGYSTVTF (SEQ ID NO: 163) | A0101 | 0.92 | 4.0 | 2 | 19 | ND | ND |
| #73 | 166-174 HHAAQFPNH (SEQ ID NO: 164) | B3801 | 0.81 | 3.14 | 0 | 26 | ND | ND |
| #74-75 | 174-182 HSFKHEDPM (SEQ ID NO: 165) | B3501 | 1.3 | 18.0 | 0 | 50 | 5 | 45 |
| #82 | 202-210 CHTPTDSCT (SEQ ID NO: 166) | B4402 | 1.02 | 3.77 | 8 | 37 | ND | ND |
| #83-84 | 209-217 CTGSQALLL (SEQ ID NO: 167) | A0101 | 0.03 | 0.29 | 0 | 21 | 3 | 33 |
| #83 **** | 206-214 TDSCTGSQA (SEQ ID NO: 168) | B3802 B4402 | 0.71 1.01 | 4.02 4.2 | 0 1 | 88 36 | ND 1 | ND 56 |
| #86 **** | 218-226 RTPYSSDNL*** (SEQ ID NO: 169) | B3503 C0401 | 0.84 0.84 | 3.0 3.0 | 0 0 | 84 84 | 4 4 | 48 48 |

TABLE 1-continued

WT1 derived immunogenic epitopes identified by IFNγ production assay for T cells responses using pool of overlapping pentadecapeptides spanning the whole sequence of WT1 protein. Bolded peptide sequences represent those tested in Example 5 and results shown in Table 3.

| 15-mer number (SEQ ID, Table IV) Containing the dominant epitope | Sequence identified | Presenting HLA allele | IFNg response of cells, % IFNg + cells | | Cytotoxic CTL response, % (at 50:1) E:T ratio vs | | | |
|---|---|---|---|---|---|---|---|---|
| | | | No WT1 peptide | WT1 peptide loaded | WT1-Autologous APC | WT1 peptide loaded autologous APC | WT1 - leukemia | WT1 + leukemia |
| #87 | 225-233 NLYQMTSQLE** (SEQ ID NO: 170) | A0201 | 0.13 | 0.9 | 3 | 87 | 0 | 0 |
| #91 **** | 238-246 WNQMNLGAT (SEQ ID NO: 171) | A0201 | 1.34 | 8.0 | 0 | 18 | 1 | 19 |
| | | C1701 | 2.1 | 12.0 | 0 | 10 | 1 | 16 |
| | | A0101 | 2.1 | 7.31 | 0 | 26 | ND | ND |
| | | B3508 | 1.23 | 5.0 | 0 | 18 | 4 | 19 |
| #91-92 | 239-248 NQMNLGATL (SEQ ID NO: 172) | A2402 | 0.02 | 0.14 | 4 | 9 | 1 | 17 |
| #91 **** | 238-248 WNQMNLGATLK (SEQ ID NO: 173) | DRB11104 | 0.59 | 6.0 | 0 | 8 | 0 | 0 |
| | 235-249 CMTWNQMNLGATLKG (SEQ ID NO: 174) | DRB10402 | 0.07 | 0.53 | 4 | 16 | 1 | 17 |
| #92 **** | 242-250 NLGATLKGV (SEQ ID NO: 175) | A0101 | 0.32 | 1.83 | 2 | 19 | ND | ND |
| | | A0201 | 0.06 | 0.75 | 1 | 18 | 2 | 19 |
| #92-93 | 243-252 LGATLKGVAA (SEQ ID NO: 176) | A0203 | 0.54 | 2.1 | 0 | 35 | ND | ND |
| #93 | 246-253 TLGVAAGS (SEQ ID NO: 177) | A6901 | 0.09 | 1.85 | 4 | 80 | ND | ND |
| #99-100 **** | 269-278 GYESDNHTT (SEQ ID NO: 178) | A0101 | 0.12 | 2.43 | 0 | 27 | 0 | 33 |
| | | B3501 | 0.1 | 0.61 | 0 | 35 | ND | ND |
| #112-113 **** | 323-332 FMCAYPGCNK (SEQ ID NO: 179) | B3501 | 1.3 | 18.0 | 0 | 70 | 5 | 45 |
| | 320-334 KRPFMCAYPGC (SEQ ID NO: 180) | DRB10401 | 0.91 | 3.48 | 9 | 5 | 5 | 5 |
| #129 | 390-398 RKFSRSDHL (SEQ ID NO: 181) | A0201 | 1.08 | 5.81 | 3 | 40 | ND | ND |
| #131 | 398-406 LKTHTRTHT (SEQ ID NO: 182) | A0201 | 1.56 | 14.0 | 0 | 38 | ND | ND |
| #141 **** | 436-445 NMHQRNHTKL** (SEQ ID NO: 183) | A0201 | 1.78 | 6.69 | 2 | 40 | 0 | 0 |
| | | B4001 | 2.1 | 7.71 | 0 | 31 | 3 | 72 |
| | | A2402 | 0.61 | 2.79 | 19 | 47 | 0 | 0 |

* - the epitope previously predicted by the computer algorithm or described in the literature
** - T-cells cytotoxic against autologous WT1 peptide loaded APCs but not leukemia cells
*** - assignment of HLA restriction to one or other allele cannot be made due to lack of targets inheriting one allele without the other
**** - rows represent peptides that can be presented by more than one HLA allele.

Using this epitope mapping strategy, 5 new 11-mer peptides were identified that stimulated CD4+ T-cell responses restricted by HLA class II alleles. The CD4+ T-cells generated in response to each of these epitopes expressed high levels of IFNγ+ T-cells. The CD4+ T-cells responding to 3 of these 5 peptide epitopes also exhibited specific cytotoxic activity against peptide loaded PHA blasts as well as unmodified WT1+ leukemic blasts selectively sharing the restricting class II HLA allele.

In 4 of the 56 donors tested, epitope mapping of T-cells sensitized with the complete pool of WT1 15-mers identified specific 15-mers eliciting both CD4+ and CD8+ T-cell responses (15-mer peptides #20, 41, 91, 112). Fine mapping of the sequences eliciting these responses identified four 11-mers that stimulated HLA class II-restricted CD4+ T-cell responses which also contained, within their sequences, 9-mers that elicited HLA class I-restricted CD8+ T-cell responses. A representative example of one of these dual stimulating peptides is presented in FIG. 3. In this case, peptide 41 was found to elicit both CD4+ and CD8+ IFNγ+ T-cell responses (FIG. 3A). Fine mapping of the 11-mers within peptide 41 eliciting the CD4+ IFNγ+ T-cell response (FIG. 3A) suggested the $_{38\text{-}48}$LDFAPPGASAY peptide as the most immunogenic sequence inducing both CD4+ and CD8+ IFNγ+ T-cell responses. Strikingly, the peptide 41 sensitized T-cells lysed PHA blasts sensitized with either the 9aa sequence ($_{38\text{-}46}$LDFAPPGAS) or the 11aa sequence ($_{38\text{-}48}$LDFAPPGASAY), but did not lyse PHA blasts loaded with the $_{36\text{-}46}$PVLDFAPPGAS or $_{37\text{-}47}$VLDFAPPGASA 11-mers. Subsequent examination of the HLA restriction of the T-cells in the culture (FIG. 3D) revealed that the class II HLA-restricted T-cells were selectively cytotoxic against targets sharing the alleles DRB1 0402 and DQB1 0302 only when loaded with the LDF 11-mer, while the T-cells restricted by HLA A0201 were able to lyse targets loaded with either the 11-mer or the 9-mer LDF peptide. In this case, it was not possible to ascertain whether DRB1 0402 or DQB1 0302 was the restricting class II HLA allele because cells were not available in the panel expressing one without the other.

Detailed description of FIG. 3. HLA class I and II restricted WT1 specific T cell respond to the same immunodominant peptide 15-mer derived from WT1 protein in the WT1 CTL sensitized with the WT1 total pool of overlapping 15-mers loaded on autologous CAMs. A. Production of IFNg by the CD8+ and CD4+WT1 specific T cells in response to secondary overnight stimulation with the same dominant WT1 derived 15-mer #41; B. Identification of the immunogenic sequence of aminoacids within pentadecapeptide #41 by IFNg production after secondary overnight stimulation with autologous PBMC loaded with a panel of 9-mers either unique for the peptide #41 (LDF—LDFAAPGAS) or contained within the neighboring overlapping 15-mer #40 (PVL—PVLDFAPPG, VLD—VLDFAPPGA) and #42 (DFA—DFAPPGASA). Only the 9-mer uniquely presented within the 15-mer #41, LDF, elicits an IFNg response; C. Peptide-specific cytotoxic activity of WT1 CTL against the panel of 9-mers and 11-mers contained within peptide #41 and loaded on autologous PHA stimulated blasts is observed against both the 11-mer LDF and 9-mer LDF contained within the 11-mer LDF as determined in a standard Cr51 release assay at 25:1 E:T ratio; D. HLA restriction of the cytotoxic activity of the WT1 CTL: T-cells restricted by HLA-A0201 lyse targets loaded with either the 11-mer or the 9-mer, while those restricted by HLA DRB10402 only lysed targets loaded with the 11-mer.

EXAMPLE 4

T-Cells Generated Against Newly Identified WT1 Epitopes Exhibit Cytotoxic Activity Against WT1+ Leukemias Once the WT1 peptide specificity was established and HLA restrictions of the IFNγ+ T-cells responding to the pool of WT1 peptides, their cytotoxic activity was examined against unmodified and peptide loaded autologous PHA blasts and against a series of allogeneic PHA blasts loaded with the identified peptides as well as primary acute leukemic cell blasts expressing WT1 protein that coexpressed the WT1 specific T-cells' restricting HLA allele. For the latter tests, WT1+ leukemic cells not expressing the restricting allele and WT1− cells sharing the restricting allele served as controls. Results are summarized in Tables 1 and 2.

As can be seen in Table 1, of 51 cultures generating IFNγ+CD8+ T-cells after secondary stimulation with an identified peptide loaded autologous APC, 50 also exhibited significant specific cytotoxic activity against autologous PHA blasts loaded with the targeted peptide. Of these, 48 also lysed allogeneic peptide loaded PHA blasts or DCs sharing the restricting HLA allele of the responding T-cells. CD4+ IFNγ+ T-cells responding to 3/5 identified 11-mer peptides presented by class II HLA alleles also lysed peptide loaded autologous and HLA-sharing allogeneic class II+ targets.

Of the T-cell cultures exhibiting epitope-specific cytotoxic activity against peptide loaded targets, 36 could be tested for cytotoxic activity against WT1+ leukemic cells coexpressing the T-cell's restricting HLA allele. Of these 36, 27 exhibited HLA-restricted cytotoxic activity against the WT1+ leukemic cells (Table 2). T-cells specific for five peptides, $_{6\text{-}15}$RDL, $_{46\text{-}54}$SAY, $_{58\text{-}66}$PAP, $_{225\text{-}233}$NLY, and $_{436\text{-}445}$NMH, presented by HLA A0201, could not lyse HLA-A0201⁺ WT1+ leukemic cells. However, HLA B4001 restricted T-cells specific for the $_{46\text{-}54}$SAY peptide, could lyse WT1+ leukemic coexpressing this HLA allele. Similarly, NMH peptide-specific HLA-restricted T-cell lines that lysed targets loaded with the NMH peptide coexpressing HLA A0201, B4001 or A2402 were only able to lyse WT1+ leukemic cells expressing the HLA B4001 allele.

TABLE 2

WT1 derived immunogenic epitopes identified by IFNγ production assay for T cells responses using pool of overlapping pentadecapeptides spanning the whole sequence of WT1 protein. Bold sequences indicate peptides tested as described in Example 5 and results provided in Table 3.

| Presenting HLA allele | Sequence identified | Prediction algorithm Binding index | Dissociation time | Cytotoxic CTL response, % (at 50:1) E:T ratio vs WT1-allo APC with restricting HLA allele | WT1 + allo APC with restricting HLA allele loaded with WT1 peptide | WT1- leukemia | WT1+ leukemia |
|---|---|---|---|---|---|---|---|
| A0101 | 146-154 NQGYSTVTF SEQ ID NO: 163 | 3 | 0.001 | 4 | 15 | ND | ND |
|  | 209-217 CTGSQALLL SEQ ID NO: 167 | 12 | 0.125 | 0 | 26 | 3 | 33 |
|  | 238-246 WNQMNLGAT SEQ ID NO: 171 | 2 | 0 | 3 | 19 | ND | ND |
|  | 242-250 NLGATLKGV SEQ ID NO: 175 | 3 | 0.01 | 1 | 17 | ND | ND |
|  | 269-278 GYESDNHTT SEQ ID NO: 178 | 15 | 1.5 | 0 | 26 | 0 | 33 |
|  | 323-332 FMCAYPGCNK** SEQ ID NO: 179 | 0 | 0.1 | 2 | 0 | 5 | 0 |
| A0201 | (-110)-(-102) PLPHFPPPSL SEQ ID NO: 144 | 21 | 2 | 1 | 24 | 2 | 22 |
|  | (-99)-(-91) THSPTHPPR SEQ ID NO: 146 | 3 | 0 | 1 | 21 | 0 | 38 |
|  | (-75)-(-67) AILDFLLLQ SEQ ID NO: 147 | 19 | 0.272 | 3 | 17 | 3 | 19 |
|  | (-47)-(-39) PGCLQQPEQ SEQ ID NO: 148 | 0 | 0 | 7 | 27 | 5 | 19 |
|  | (-27)-(-19) KLGAAEASA SEQ ID NO: 150 | 19 | 17 | 2 | 22 | 10 | 37 |
|  | 6-15 RDLNALLPAV SEQ ID NO: 152 | 18 | 0.2 | 4 | 31 | 0 | 9 |
|  | 22-31 GGCALPVSGA SEQ ID NO: 153 | 13 | 0.003 | 3 | 25 | 3 | 47 |
|  | 38-46 LDFAPPGAS SEQ ID NO: 155 | 11 | 0 | 1 | 62 | 0 | 40 |
|  | 46-54 SAYGSLGGP** SEQ ID NO: 157 | 14 | 0 | 5 | 31 | 0 | 0 |
|  | 58-66 PAPPPPPPP** SEQ ID NO: 158 | 5 | 0 | 1 | 18 | 0 | 0 |
|  | 126-134 RMFPNAPYL* SEQ ID NO: 161 | 22 | 313 | 1 | 52 | 2 | 25 |
|  | 225-233 NLYQMTSQLE** SEQ ID NO: 170 | 23 | 68 | 3 | 28 | 0 | 0 |
|  | 238-246 WNQMNLGAT SEQ ID NO: 171 | 19 | 0.3 | 0 | 21 | 1 | 19 |
|  | 242-250 NLGATLKGV SEQ ID NO: 175 | 24 | 160 | 1 | 14 | 2 | 19 |
|  | 390-398 RKFSRSDHL SEQ ID NO: 181 | 11 | 0.054 | 1 | 27 | ND | ND |

TABLE 2-continued

WT1 derived immunogenic epitopes identified by IFNγ production
assay for T cells responses using pool of overlapping pentadecapeptides spanning the whole
sequence of WT1 protein. Bold sequences indicate peptides tested as described in Example 5
and results provided in Table 3.

| Presenting HLA allele | Sequence identified | Prediction algorithm | | Cytotoxic CTL response, % (at 50:1)E:T ratio vs | | | |
|---|---|---|---|---|---|---|---|
| | | Binding index | Dissociation time | WT1-allo APC with restricting HLA allele | WT1 + allo APC with restricting HLA allele loaded with WT1 peptide | WT1-leukemia | WT1+ leukemia |
| | 398-406 LKTHTRTHT SEQ ID NO: 182 | 5 | 0.18 | 1 | 22 | ND | ND |
| | 436-445 NMHQRNHTKL** SEQ ID NO: 183 | 20 | 15 | 4 | 32 | 0 | 0 |
| A0203 | 243-252 LGATLKGVAA SEQ ID NO: 176 | 19 | NA | 0 | 21 | ND | ND |
| A2402 | 239-248 NQMNLGATL SEQ ID NO: 172 | 10 | 7.2 | 0 | 2 | 1 | 17 |
| | 436-445 NMHQRNHTKL** SEQ ID NO: 183 | 13 | 0.6 | 13 | 27 | 0 | 0 |
| A6901 | 246-253 TLGVAAGS SEQ ID NO: 177 | NA | NA | 0 | 57 | ND | ND |
| B0702 | (-125)-(-117) RQRPHPGAL SEQ ID NO: 142 | 15 | 40 | 1 | 53 | 1 | 67 |
| | (-119)-(-111) GALRNPTAC SEQ ID NO: 143 | 2 | 0.3 | 5 | 22 | 1 | 60 |
| A3101 | (-107)-(-99) HFPPSLPPT SEQ ID NO: 145 | NA | 0.01 | 0 | 27 | ND | ND |
| B3501 | (-8)-(-1) ASGSEPQQM SEQ ID NO: 151 | NA | 15 | 3 | 51 | 5 | 39 |
| | 135-143 PSCLESQPA SEQ ID NO: 162 | NA | 0.075 | 0 | 21 | ND | ND |
| | 174-182 HSFKHEDPM SEQ ID NO: 165 | NA | 10 | 3 | 63 | 5 | 45 |
| | 269-278 GYESDNHTT SEQ ID NO: 178 | NA | 0.004 | 0 | 23 | ND | ND |
| | 323-332 FMCAYPGCNK SEQ ID NO: 179 | NA | 0.01 | 0 | 61 | 5 | 45 |
| B3503 | 122-130 SGQARMFPN SEQ ID NO: 160 | NA | NA | 3 | 41 | ND | ND |
| | 218-226 RTPYSSDNL SEQ ID NO: 169 | NA | NA | 3 | 31 | 4 | 48 |
| B3508 | 238-246 WNQMNLGAT SEQ ID NO: 171 | NA | NA | 2 | 21 | 4 | 19 |
| B3802 | 206-214 TDSCTGSQA SEQ ID NO: 168 | NA | NA | 1 | 53 | ND | ND |

TABLE 2-continued

WT1 derived immunogenic epitopes identified by IFNγ production assay for T cells responses using pool of overlapping pentadecapeptides spanning the whole sequence of WT1 protein. Bold sequences indicate peptides tested as described in Example 5 and results provided in Table 3.

| Presenting HLA allele | Sequence identified | Prediction algorithm | | WT1-allo APC with restricting HLA allele | Cytotoxic CTL response, % (at 50:1) E:T ratio vs | | |
|---|---|---|---|---|---|---|---|
| | | Binding index | Dissociation time | | WT1 + allo APC with restricting HLA allele loaded with WT1 peptide | WT1- leukemia | WT1+ leukemia |
| B3801 | 166-174<br>HHAAQFPNH<br>SEQ ID NO: 164 | 11 | 0.3 | 1 | 17 | ND | ND |
| B3901 | 30-38<br>GAAQWAPVL<br>SEQ ID NO: 154 | 12 | 3 | 0 | 19 | ND | ND |
| B4001 | (-99)-(-91)<br>THSPTHPPR<br>SEQ ID NO: 146 | 3 | 0.02 | 0 | 31 | 3 | 65 |
| | 46-54<br>SAYGSLGGP<br>SEQ ID NO: 157 | 1 | 0.002 | 8 | 24 | 3 | 68 |
| | 436-445<br>NMHQRNHTKL<br>SEQ ID NO: 183 | 1 | 0.002 | 1 | 26 | 3 | 72 |
| B4402 | 202-210<br>CHTPTDSCT<br>SEQ ID NO: 166 | 3 | NA | 7 | 19 | ND | ND |
| | 206-214<br>TDSCTGSQA<br>SEQ ID NO: 168 | 2 | NA | 0 | 88 | 1 | 56 |
| | 106-114<br>ACRYGPFGP<br>SEQ ID NO: 159 | 4 | NA | 7 | 23 | ND | ND |
| B4701 | (-47)-(-37)<br>PGCLQQPEQ<br>SEQ ID NO: 148 | 1 | NA | 1 | 25 | ND | ND |
| B5701 | 6-15<br>RDLNALLPAV<br>SEQ ID NO: 152 | NA | NA | 1 | 22 | ND | ND |
| C0401 | 122-130<br>SGQARMFPN<br>SEQ ID NO: 160 | NA | NA | 3 | 41 | ND | ND |
| C1701 | 238-246<br>WNQMNLGAT<br>SEQ ID NO: 171 | NA | NA | 0 | 7 | 1 | 16 |
| DRB$_1$0101 | (-47)-(-37)<br>PGCLQQPEQQG<br>SEQ ID NO: 149 | 8 | NA | 1 | 25 | ND | ND |
| DRB$_1$0402 | 38-48<br>LDFAPPGASAY<br>SEQ ID NO: 156 | NA | NA | 1 | 71 | 0 | 40 |
| DRB$_1$0402 | 235-249<br>CMTWNQMNLGA<br>TLKG<br>SEQ ID NO: 174 | NA | NA | 2 | 15 | 1 | 17 |
| DRB$_1$0401 | 320-334<br>KRPFMCAYPGC<br>SEQ ID NO: 180 | 22 | NA | 3 | 0 | 5 | 5 |

TABLE 2-continued

WT1 derived immunogenic epitopes identified by IFNγ production assay for T cells responses using pool of overlapping pentadecapeptides spanning the whole sequence of WT1 protein. Bold sequences indicate peptides tested as described in Example 5 and results provided in Table 3.

| Presenting HLA allele | Sequence identified | Prediction algorithm | | Cytotoxic CTL response, % (at 50:1) E:T ratio vs | | | |
|---|---|---|---|---|---|---|---|
| | | Binding index | Dissociation time | WT1-allo APC with restricting HLA allele | WT1 + allo APC with restricting HLA allele loaded with WT1 peptide | WT1-leukemia | WT1+ leukemia |
| DRB₁1104 | 238-248 WNQMNLGATLK SEQ ID NO: 173 | NA | NA | 2 | 1 | 0 | 0 |

\* - previously reported epitopes;
\*\* - T cells cytotoxic against the autologous WT1 peptide loaded APC but not the leukemic cells.

To ascertain that the cytotoxic activity of the WT1 peptide-specific T-cells observed against allogeneic WT1+ leukemic cells sharing the T-cells restricting allele does not reflect the presence of alloresponsive T-cells in the T-cell lines, we tested the cytotoxic activity of 13 of these HLA-restricted WT1 peptide specific T-cell lines against WT1+ leukemic cells and WT1− PHA blasts cultured from the same leukemic patient. As shown in Table 3a, the WT1 specific T-cells lysed the WT1+ leukemic cells but not PHA blasts from the same patient.

TABLE 3a

Cytotoxic activity of the T cells specific for WT1 derived immunogenic epitopes identified by IFNγ production assay for T cells responses using pool of overlapping pentadecapeptides spanning the whole sequence of WT1 protein and tested against WT1 positive primary leukemic cells and PHA blasts of the same origin.

| 15-mer number Containing the dominant epitope | Sequence identified | Presenting HLA allele | Cytotoxic CTL response, % (at 50:1) E:T ratio vs | |
|---|---|---|---|---|
| | | | WT1+ Leukemia ** | PHA blasts *** |
| #1 | $_{(-125)-(-117)}$RQRPHPGAL SEQ ID NO: 142 | B0702 | 67 | 2 |
| #2 | $_{(-119)-(-111)}$GALRNPTAC SEQ ID NO: 143 | B0702 | 60 | 1 |
| #4 | $_{(-110)-(-102)}$PLPHFPPSL SEQ ID NO: 144 | A0201 | 22 | 1 |
| #7 | $_{(-99)-(-91)}$THSPTHPPR SEQ ID NO: 146 | B4001 A0201 | 65 38 | 5 3 |
| #24-25 | $_{(-27)-(-19)}$KLGAAEASA SEQ ID NO: 150 | A0201 | 37 | 8 |
| #29-30 | $_{(-8)-(-1)}$ ASGSEPQQM SEQ ID NO: 151 | B3501 | 39 | 9 |
| #37 | $_{22-31}$GGCALPVSGA SEQ ID NO: 153 | A0201 | 47 | 6 |
| #43 | $_{46-54}$SAYGSLGGP* SEQ ID NO: 157 | B4001 | 68 | 3 |
| #62-63 | $_{126-134}$RMFPNAPYL* SEQ ID NO: 161 | A0201 | 25 | 3 |
| #86 | $_{218-226}$RTPYSSDNL SEQ ID NO: 169 | B3503 C0401 | 48 48 | 1 1 |

TABLE 3a-continued

Cytotoxic activity of the T cells specific for WT1 derived immunogenic epitopes identified by IFNγ production assay for T cells responses using pool of overlapping pentadecapeptides spanning the whole sequence of WT1 protein and tested against WT1 positive primary leukemic cells and PHA blasts of the same origin.

| 15-mer number Containing the dominant epitope | Sequence identified | Presenting HLA allele | Cytotoxic CTL response, % (at 50:1) E:T ratio vs | |
|---|---|---|---|---|
| | | | WT1+ Leukemia ** | PHA blasts *** |
| #141 | $_{436-445}$NMHQRNHTKL* SEQ ID NO: 183 | B4001 | 72 | 1 |
| | | | P < 0.001 | |

\* - the epitope previously predicted by the computer algorithm or described in the literature
\*\* - leukemia samples were presented either by immortalized leukemia cell lines or by primary leukemia cells obtained from patients with WT1+ leukemia
\*\*\* - PHA blasts were generated from PBMC derived from the same patients as the WT1+ primary leukemia PHA blasts were not available from every patient that provided leukemia blasts for this study. Nevertheless, these results provide evidence that the cytotoxicity of the WT1 specific T-cells is not ascribable to contaminating alloreactivity. A second, more inclusive, but less direct line of evidence is provided by a paired comparison of the responses of T-cells derived from 35 of the donors that had been contemporaneously sensitized in vitro against either WT1 peptide pool loaded or unmodified autologous EBVBLCL, against these primary leukemias. As shown in Table 3b, T-cells sensitized with the WT1 peptide pool-loaded EBVBLCL lysed WT1+ leukemic cells sharing the T-cells' restricting HLA allele in 25 of 35 cases. In contrast, T-cells sensitized with autologous EBVBLCL alone consistently failed to lyse the same WT1+ leukemia targets.

TABLE 3b

Leukemocidal activity of defined epitope-specific and HLA restricted T cells from normal donors sensitized with either autologous EBV BLCL or EBV BLCL loaded with pooled WT1 peptides against primary WT1⁺ leukemia sharing the T cells restricting HLA alleles.

| 15-mer number Containing the dominant epitope | Sequence identified | Presenting HLA allele | Cytotoxic CTL response, %(at 50:1) E:T ratio vs WT1⁺ leukemia expressing restricting HLA allele | |
|---|---|---|---|---|
| | | | WT1 CTL | EBV CTL |
| #1 | $_{(-125)-(-117)}$RQRPHPGAL SEQ ID NO: 142 | B0702 | 67 | 1 |
| #2 | $_{(-119)-(-111)}$GALRNPTAC SEQ ID NO: 143 | B0702 | 60 | 2 |
| #4 | $_{(-110)-(-102)}$PLPHFPPSL SEQ ID NO: 144 | A0201 | 22 | 3 |
| #7 | $_{(-99)-(-91)}$THSPTHPPR SEQ ID NO: 146 | B4001 A0201 | 65 38 | 0 3 |
| #13 | $_{(-75)-(67)}$AILDFLLLQ SEQ ID NO: 142 | A0201 | 19 | 5 |
| #20 | $_{(-47)-(39)}$PGCLQQPEQ SEQ ID NO: 1148 | A0201 | 19 | 10 |
| #24-25 | $_{(-27)-(-19)}$KLGAAEASA SEQ ID NO: 150 | A0201 | 37 | 5 |
| #29-30 | $_{(-8)-(-1)}$ASGSEPQQM SEQ ID NO: 151 | B3501 | 39 | 0 |
| #33 | $_{6-15}$RDLNALLPAV** SEQ ID NO: 152 | A0201 | 9 | 0 |
| #37 | $_{22-31}$GGCALPVSGA SEQ ID NO: 153 | A0201 | 47 | 3 |

TABLE 3b-continued

Leukemocidal activity of defined epitope-specific and HLA restricted T cells from normal donors sensitized with either autologous EBV BLCL or EBV BLCL loaded with pooled WT1 peptides against primary WT1+ leukemia sharing the T cells restricting HLA alleles.

| 15-mer number Containing the dominant epitope | Sequence identified | Presenting HLA allele | Cytotoxic CTL response, %(at 50:1) E:T ratio vs WT1+ leukemia expressing restricting HLA allele | |
|---|---|---|---|---|
| | | | WT1 CTL | EBV CTL |
| #41 | $_{38-46}$LDFAPPGAS SEQ ID NO: 1554 | A0201 | 40 | 0 |
| | $_{38-48}$LDFAPPGASAY SEQ ID NO: 156 | DRB$_1$0402 | 40 | 0 |
| #43 | $_{46-54}$SAYGSLGGP* SEQ ID NO: 157 | A0201 | 0 | 0 |
| | | B4001 | 68 | 3 |
| #46 | $_{58-66}$PAPPPPPPP* SEQ ID NO: 158 | A0201 | 0 | 0 |
| #62-63 | $_{126-134}$RMFPNAPYL* SEQ ID NO: 161 | A0201 | 25 | 2 |
| #74-75 | $_{174-182}$HSFKHEDPM SEQ ID NO: 165 | B3501 | 45 | 5 |
| #83-84 | $_{209-217}$CTGSQALLL SEQ ID NO: 167 | A0101 | 33 | 3 |
| #83 | $_{206-214}$TDSCTGSQA SEQ ID NO: 168 | B4402 | 56 | 1 |
| #86 | $_{218-226}$KTPYSSDNL SEQ ID NO: 169 | B3503 | 48 | 4 |
| | | C0401 | 48 | 4 |
| #87 | $_{225-233}$NLYQMTSQLE* SEQ ID NO: 170 | A0201 | 0 | 0 |
| #91 | $_{238-246}$WNQMNLGAT SEQ ID NO: 171 | A0201 | 19 | 1 |
| | | C1701 | 16 | 1 |
| | | B3508 | 19 | 4 |
| #91-92 | $_{239-248}$NQMNLGATL SEQ ID NO: 172 | A2402 | 17 | 1 |
| #91 | $_{238-248}$WNQMNLGATLK SEQ ID NO: 173 | DRB$_1$1104 | 0 | 0 |
| | $_{235-249}$CMTWNQMNLGATLKG SEQ ID NO: 174 | DRB$_1$0402 | 17 | 1 |
| #92 | $_{242-250}$NLGATLKGV SEQ ID NO: 175 | A0201 | 19 | 2 |
| #99-100 | $_{269-278}$GYESDNHTT SEQ ID NO: 178 | A0101 | 33 | 0 |
| #112-113 | $_{323-332}$FMCAYPGCNK SEQ ID NO: 179 | B3501 | 45 | 5 |
| | $_{320-334}$KRPFMCAYPGC SEQ ID NO: 180 | DBB$_1$0401 | 5 | 5 |
| #141 | $_{436-445}$NMHQRNHTKL* SEQ ID NO: 183 | A0201 | 0 | 0 |
| | | B4001 | 72 | 3 |
| | | A2402 | 0 | 0 |
| | | | | p < 0.001 |

\* - the epitope previously predicted by the computer algorithm or described in the literature

EXAMPLE 5

Immunogenicity of the Newly Identified WT1 Epitopes

In order to ascertain that that the peptides identified by mapping responses in single donors were also immunogenic in a high proportion of individuals bearing the same presenting HLA allele, it was determined whether these epitopes could elicit appropriately restricted T-cell responses in groups of 6-12 individuals expressing that HLA allele. For this purpose, the T-cells from each donor were sensitized with the identified epitope loaded on a panel of artificial antigen presenting cells (AAPC) (42) each expressing a single HLA allele, specifically A0201, A0301, A2402 or B0702. As shown in Table 4, of 9 peptides identified that are presented by HLA-A0201, all were able to stimulate WT1-specific IFNγ+ T-cell responses in a proportion of HLA-A0201+ individuals. The previously reported 126-134RM-FPNAPYL peptide presented by HLA-A0201 allele elicited responses in 5/12 (42%) HLA-A0201+ normal donors tested. In comparison, 5 of the other 8 peptides tested elicited WT1 peptide-specific responses in 50-75% of the same HLA-A0201+ donors. Two WT1 epitopes presented by the HLA-B0702 allele also elicited WT1 specific T-cell responses in 50% and 63% of the tested individuals respectively (Table 4). All of the peptides tested elicited specific responses in at least 2 additional donors bearing their presenting HLA allele.

TABLE 4

Proportion of normal donors responding to identified WT1 peptides loaded on AAPCs expressing a single HLA allele.

| HLA allele expressed by AAPC | Sequence previously identified to be presented by the HLA allele expressed by the AAPC | Identified in # of donors after total pool stimulation on CAMs | Proportion of normal donors responding to the peptide loaded on AAPCs (%) | Predicted Binding index | Predicted Dissociation time | WT1 sequence predicted to be immunogenic when presented by the HLA alleles expressed by the AAPC | Predicted Binding index | Predicted Dissociation time | Proportion of responses in normal donors to the peptide stimulation |
|---|---|---|---|---|---|---|---|---|---|
| A0201 | (−99)-(−91) THSPTHPPR SEQ ID NO: 146 | 1 | 6/12 (50%) | 3 | 0 | (−99)-(−91) THSPTHPPR SEQ ID NO: 146 | 3 | 0 | 6/12 (50%) |
|  | (−75)-(−67) AILDFLLLQ SEQ ID NO: 147 | 1 | 8/12 (67%) | 19 | 0.272 | (−78)-(−70) LLAAILDFL SEQ ID NO: 184 | 28 | 225 | 8/12 (67%) |
|  | (−47)-(−39) PGCLQQPEQ SEQ ID NO: 148 | 2 | 2/12 (16%) | 0 | 0 | (−45)-(−36) CLQQPEQQGV SEQ ID NO: 185 | 21 | 70 | 2/12 (16%) |
|  | (−27)-(−19) KLGAAEASA SEQ ID NO: 149 | 1 | 8/12 (67%) | 19 | 17 | (−27)-(−19) KLGAAEASA SEQ ID NO: 150 | 19 | 17 | 8/12 (67%) |
|  | 6-15 RDLNALLPAV SEQ ID NO: 152 | 1 | 3/12 (25%) | 18 | 0.2 | 7-15 DLNALLPAV SEQ ID NO: 186 | 27 | 12 | 3/12 (25%) |
|  |  |  |  |  |  | 10-18 ALLPAVPSL SEQ ID NO: 187 | 33 | 181 | 3/12 (25%) |
|  | 22-31 GGCALPVSGA SEQ ID NO: 153 | 3 | 9/12 (75%) | 13 | 0.003 | 22-31 GGCALPVSGA SEQ ID NO: 153 | 13 | 0.003 | 9/12 (75%) |
|  | 38-46 LDFAPPGAS SEQ ID NO: 155 | 2 | 8/12 (67%) | 11 | 0 | 37-45 VLDFAPPGA SEQ ID NO: 188 | 16 | 4 | 0/12 (0%) |
|  | 126-134 RMFPNAPYL SEQ ID NO: 161 | 1 | 5/12 (42%) | 22 | 313 | 126-134 RMFPNAPYL SEQ ID NO: 161 | 22 | 313 | 5/12 (42%) |
|  | 238-246 WNQMNLGAT SEQ ID NO: 171 | 2 | 3/12 (25%) | 19 | 0.3 | 235-243 CMTWNQMNL SEQ ID NO: 189 | 17 | 1.5 | 0/8 |
|  | total pool | 13/27 (48%) | 8/12 (67%) |  |  |  |  |  |  |
| A0301 | 126-134 RMFPNAPYL SEQ ID NO: 161 | 1 | 2/8 (25%) | 10 | 4.5 | 124-133 QARMFPNAPY SEQ ID NO: 190 | 14 | 0.001 | 0/8 |
|  | total pool | 1/8 (12%) | 2/8 (25%) |  |  |  |  |  |  |
| A2402 | 239-248 NQMNLGATL SEQ ID NO: 172 | 1 | 4/6 (60%) | 10 | 7.2 | 235-243 CMTWNQMNL SEQ ID NO: 189 | 10 | 4 | 1/6 (17%) |
|  | total pool | 2/6 (33%) | 6/6 (100%) |  |  |  |  |  |  |

TABLE 4-continued

Proportion of normal donors responding to identified WT1 peptides
loaded on AAPCs expressing a single HLA allele.

| HLA allele expressed by AAPC | Sequence previously identified to be presented by the HLA allele expressed by the AAPC | Identified in # of donors after total pool stimulation on CAMs | Proportion of normal donors responding to the peptide loaded on AAPCs (%) | Predicted Binding index | Predicted Dissociation time | WT1 sequence predicted to be immunogenic when presented by the HLA alleles expressed by the AAPC | Predicted Binding index | Predicted Dissociation time | Proportion of responses in normal donors to the peptide stimulation |
|---|---|---|---|---|---|---|---|---|---|
| B0702 | (−125)-(−117) RQRPHPGAL SEQ ID NO: 142 | 1 | 4/8 (50%) | 15 | 40 | (−125)-(−117) RQRPHPGAL SEQ ID NO: 142 | 15 | 40 | 4/8 (50%) |
|  | (−119)-(−111) GALRNPTAC SEQ ID NO: 143 | 1 | 5/8 (63%) | 2 | 0.3 | (−118)-(−109) ALRNPTACPL SEQ ID NO: 191 | 15 | 120 | 5/8 (63%) |
|  | 323-332 FMCAYPGCNK SEQ ID NO: 179 | 1 | 3/8 (38%) | 1 | 0.015 | 327-335 YPGCNKRYF SEQ ID NO: 192 | 17 | 0.4 | 4/8 (50%) |
|  | Total pool | 2/8 (25%) | 3/8 (38%) |  |  |  |  |  |  |
| DRB10402 | 38-48 LDFAPPGASAY SEQ ID NO: 156 | 1 | 0/2 (tested on CAMs not on AAPC) | NA | NA | 35-49 APVLDFAPPGAS AYG SEQ ID NO: 193 | 20 | NA | ND |

EXAMPLE 6

Comparison of Responses to Peptides Identified by Mapping Responses to Pooled WT1 15-Mers with Responses to Previously Reported WT1 Peptides Predicted by Binding Algorithms to be Immunogenic Primary responses by normal donor T-cells were compared to individual WT1 peptides identified by the mapping strategy to responses against other WT1 peptides containing flanking sequences predicted to have a higher binding index for the presenting HLA allele using binding algorithms previously described (44,45). As shown in Table 4 above, the predicted binding indices for 8/12 mapped epitopes were only somewhat lower than those for the most studied WT1 peptide, RMF, presented by HLA A0201. However, their dissociation times were markedly lower. Nevertheless, T-cell responses to each of these peptides were elicited in a high proportion of normal donors.

In five instances, the mapped peptide specificity (i.e. $_{(-99)-(-91)}$THS, $_{(-22)-(-19)}$KLG, $_{22-31}$GGC, $_{126-134}$RMF and $_{(-125)-(-117)}$RQR) was identical to the peptide with the highest affinity for the presenting HLA allele predicted by the binding algorithm within the stimulating 15-mer. In those instances in which the mapped sequences and the sequences predicted to have the highest binding index differed, the proportion of donors responding to individual mapped peptides were equal or greater than those generated in response to the neighboring epitopes predicted to have higher affinity. For example, IFNγ+ T-cell responses were generated to the $_{38-46}$LDF peptide in 8/12 (67%) of HLA A0201 donors tested, while none responded to the predicted and previously reported (46) epitope $_{37-45}$VLDFAPPGA Similarly, among HLA A2402+ donors, 4/6 donors (60%) responded to the $_{239-248}$NQMNLGATL peptide while only 1/6 responded to the $_{235-243}$CMTWNQMNL peptide previously reported to be presented by this allele (29).

To directly compare peptides presented by HLA A0201 that were identified by matrix mapping with flanking peptides with higher predicted binding indices, the peptides, mixed at equal concentration, were loaded on HLA A0201+ AAPCs and used to sensitize T-cells from 8 of the HLA A0201+ normal donors. After 35 days of sensitization, the T-cells were then washed and secondarily restimulated for 24 hours with aliquots of irradiated autologous PBMC loaded with each individual peptide. Responding IFNγ+ T-cells were then quantitated by FACS. The results, presented in FIG. 5, demonstrate that although the 22-31GGC peptide has the lowest binding index and the shortest predicted dissociation time, it induced strong IFNγ+ T-cell responses in 7/8 donors. Furthermore, although 3/8 donors responded to the $_{6-15}$RDL, $_{10-18}$ ALL and $_{7-15}$ DLN peptides, $_{6-15}$ RDL peptides identified by response mapping elicited higher numbers of IFNγ+ T-cells. In comparisons of the $_{(-75)-(-67)}$AILDFLLLQ with flanking $_{(-78)-(-70)}$ LLAAILDFL sequence, the AIL peptide elicited superior responses and in a higher proportion of donors (6/8 vs. 3/8 ). Similarly, in comparisons of the mapped $_{38-46}$LDFAP-PGAS peptide with the previously reported $_{37-45}$VLDFAP-PGA peptide (46) the LDF peptide induced strong responses in 5 of the 8 donors while the VLD peptide induced low responses in only 2 of these donors.

Figure 5:
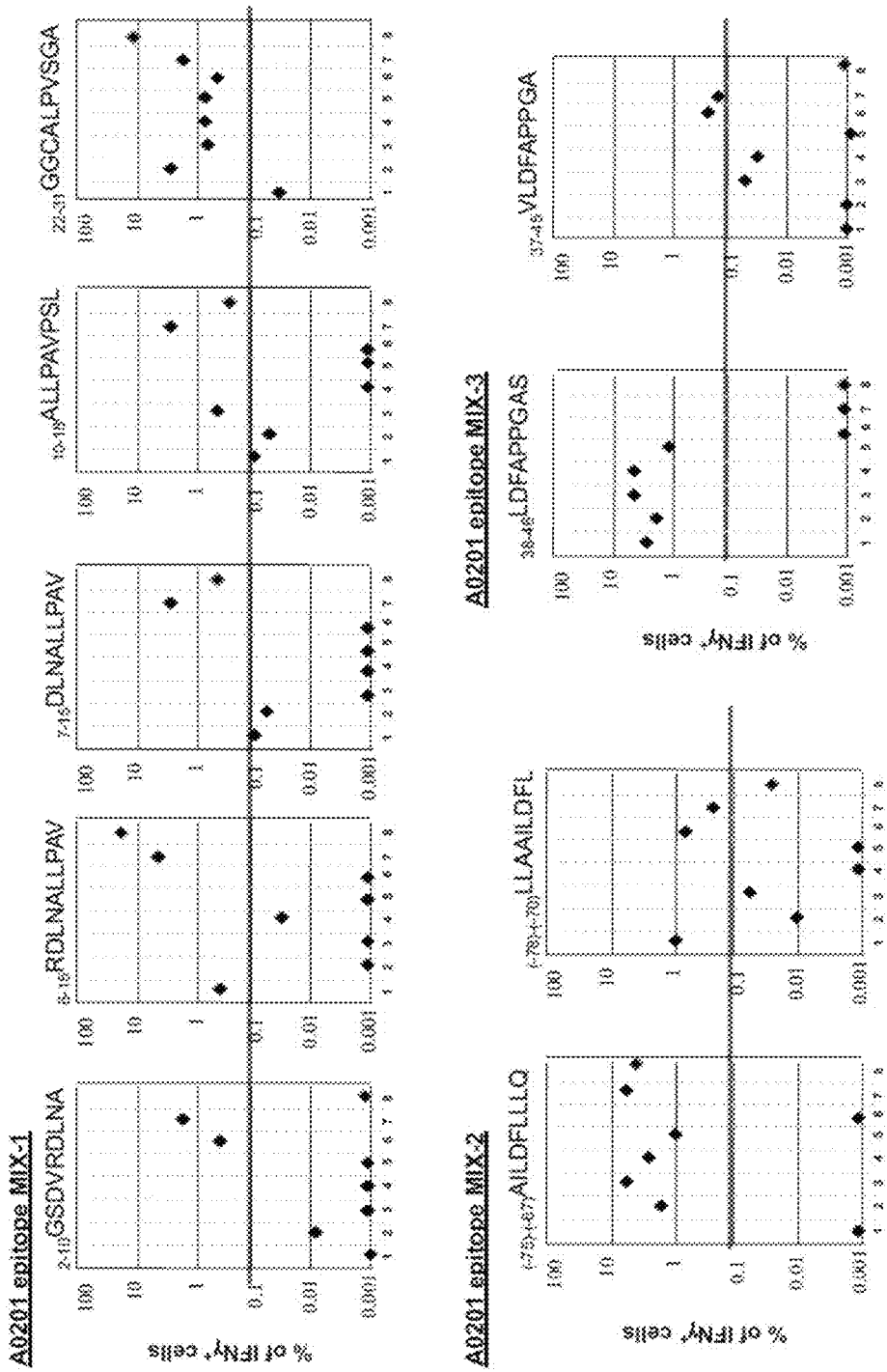
FIG. 5 depicts results using mixed A0201 epitopes loaded on A0201-AAPC in 8 normal A0201+ donors.

Detailed description of FIG. 5. IFNγ+ T-cell responses to equimolar mixtures of 9-mer peptides identified by epitope mapping of in vitro responses and peptides within the same 15-mer or adjacent overlapping 15-mer peptides predicted to have higher binding affinity and immunogenicity. A. Responses to a mixture of nonamers spanning amino acids +2 to +31 including the $_{6-15}$ RDL and $_{22-31}$GGC peptides to which HLA A0201+ donors responded in epitope mapping studies. B. Responses to the in vitro mapped $_{(-75)-(-67)}$ AILDFLLLQ epitope and a flanking peptide $_{(-78)-(-70)}$ LLAAILDFL with higher predicted binding affinity. C. Responses to the in vitro mapped $_{38-46}$LDFAPPGAS epitope and the overlapping $_{37-45}$VLDFAPPGA predicted to have higher binding affinity.

FIG. 5 presents maps of the WT1 protein. FIG. 5C defines the localization of all previously reported antigenic epitopes presented by HLA class I and II alleles; FIG. 5D depicts the location of immunogenic peptides identified in this report. As can be seen, the 11 epitopes previously reported to be presented by class I and 10 presented by class II HLA alleles are principally clustered in sequences encoded by exons 1, 7 and 10, while the epitopes recognized by normal T-cells sensitized with the WT1 peptide pool are principally clustered in sequences encoded by the first 5 exons. Thus, 26 of the new epitopes are included in each of the four major isoforms of WT1 resulting from splice variants that do or do not include the 17 amino acid sequence (aas 250-266) in exon 5 or the three amino acid sequence ($_{400-410}$KTS) between zinc fingers 3 and 4. While the epitopes are broadly distributed, clusters of epitopes were detected in the RNA recognition domain in exon 1 and the activation domain (aa 181-250) (FIG. 5F) proximal to the spliced 17aa segment in exon 5. The latter area also contained those epitopes most frequently recognized by multiple donors (FIG. 5E). Nine newly identified epitopes map to a 126 amino acid sequence at the N terminus encoded by a segment of the WT1 gene initially described by Gessler et al[37] that is centromeric to exon 1 of the (Exon 5$^+$, KTS$^+$) isoform of WT1 and includes the long isoform of WT1 initiated at a CUG codon upstream of the AUG initiator for exon 1.[50] Strikingly, each of the epitopes identified in this sequence elicits IFNγ+ T-cells that are cytolytic against leukemic blasts coexpressing WT1 and the T-cells' restricting HLA allele.

EXAMPLE 7

Inhibitory Effect of Peptides in Ovarian Carcinoma

The utility of peptides described herein in treating ovarian cancer was evaluated in two studies. In the first study, the inhibitory effect on ovarian tumor engraftment of T-cells specific for different WT1 peptides was evaluated by pre-incubating T cells at different doses with SKOV3-A2 ovarian carcinoma cells before injection into NOD/SCID mice. T cell cultures specific for the following immunodominant epitopes were prepared using methods described above: A0201 restricted WT1 peptide LKTHTRTHT (SEQ ID NO:182) specific T cells; A0301 restricted WT1 peptide RQRPHPGAL (SEQ ID NO:142) specific T cells, and A0201 restricted WT1 peptide HFPPSLPPT (SEQ ID NO:145) T cells. T cells to tumor cell ratios tested were 50:1, 10:1, 5:1 and control (no T cells). Following tumor injection, the tumor burden was monitored by bioluminescent imaging. For all three T cell lines at each dose, a significant reduction in tumor burden was observed over time vs. control. Furthermore, mouse survival was prolonged by pre-incubation of tumor cells with WT1 peptide specific T cells. In control groups, all mice were dead by 70 days post tumor injection. Increased survival was seen dose-responsively with the T cell: tumor cell dose, which for the 50:1 dose for all T cell lines still had some animals alive at 96 days, and also at 10:1 for the LKTHTRTHT (SEQ ID NO:182) specific line.

In a second experiment, WT1 peptide specific T cells were administered intravenously to NOD/SCID mice bearing pre-established ovarian carcinoma SKOV3-A2 xenografts. T cell lines evaluated were: A0201 restricted WT1 peptide LKTHTRTHT (SEQ ID NO:182) specific T cells and A0301 restricted WT1 peptide RQRPHPGAL (SEQ ID NO:142) specific T cells. Tumor burden was monitored by bioluminescence, tumor infiltration by human CD3+ cells evaluated and survival recorded. In both cases, the WT1 specific T cells afforded reduced tumor burden vs. control, increased tumor infiltration by human CD3+ cells and increased survival.

EXAMPLE 8

Recognition of Epitopes by Leukemia Patient T Cells

A phase I clinical trial was conducted using transplant donor-derived T-cells sensitized with the full pool of WT1 derived pentadecapeptides described above, in the adoptive therapy of patients who have relapsed following an allogeneic marrow transplant from a normal related or unrelated donor. The HLA restricting alleles and corresponding immunodominant WT1 epitopes are as follows: A0201, SEQ ID NO:147; A0203, SEQ ID NOs:176 and 183; B3503 and C0401, SEQ ID NOs:161 and 169; A6901, SEQ ID NO:177; A0201, SEQ ID NO:182; B4701 and DRB$_1$ 0102, SEQ ID NOs: 148 and 149; A3101, SEQ ID NO:145; B4402, SEQ ID NOs:158 and 166; B3503, SEQ ID NOs:146 and 162; DRB$_1$ 1104, SEQ ID NO:149. It is noted that several of the immunodominant epitopes eliciting the WT1 specific T-cells that were used were directed against epitopes in the N-terminal region of the gene, upstream from exon 1, i.e., SEQ ID NOs:145, 147, 148 and 149. Two of the donors responded to PGCLQQPEQQG, SEQ ID NO:149, and both treated patients had temporary clearance of WT1$^+$ leukemic cells following adoptive transfer.

EXAMPLE 9

Pentadecapeptides

The following pentadecapeptides were synthesized. H2N refers to the N-terminal end of the peptide, and —COOH the C-terminus.

TABLE 5

| Sequence of pentadecapeptides |
|---|
| SEQ ID NO: 1.H2N-SRQRP HPGAL RNPTA -COOH |
| SEQ ID NO: 2.H2N-PHPGA LRNPT ACPLP -COOH |
| SEQ ID NO: 3.H2N-ALRNP TACPL PHFPP -COOH |
| SEQ ID NO: 4.H2N-PTACP LPHFP PSLPP -COOH |
| SEQ ID NO: 5.H2N-PLPHF PPSLP PTHSP -COOH |
| SEQ ID NO: 6.H2N-FPPSL PPTHS PTHPP -COOH |
| SEQ ID NO: 7.H2N-LPPTH SPTHP PRAGT -COOH |
| SEQ ID NO: 8.H2N-HSPTH PPRAG TAAQA -COOH |
| SEQ ID NO: 9.H2N-HPPRA GTAAQ APGPR -COOH |
| SEQ ID NO: 10.H2N-AGTAA QAPGP RRLLA -COOH |
| SEQ ID NO: 11.H2N-AQAPG PRRLL AAILD -COOH |
| SEQ ID NO: 12.H2N-GPRRL LAAIL DFLLL -COOH |

TABLE 5-continued

Sequence of pentadecapeptides

SEQ ID NO: 13. H2N-LLAAI LDFLL LQDPA -COOH
SEQ ID NO: 14. H2N-ILDFL LLQDP ASTCV -COOH
SEQ ID NO: 15. H2N-LLLQD PASTC VPEPA -COOH
SEQ ID NO: 16. H2N-DPAST CVPEP ASQHT -COOH
SEQ ID NO: 17. H2N-TCVPE PASQH TLRSG -COOH
SEQ ID NO: 18. H2N-EPASQ HTLRS GPGCL -COOH
SEQ ID NO: 19. H2N-QHTLR SGPGC LQQPE -COOH
SEQ ID NO: 20. H2N-RSGPG CLQQP EQQGV -COOH
SEQ ID NO: 21. H2N-GCLQQ PEQQG VRDPG -COOH
SEQ ID NO: 22. H2N-QPEQQ GVRDP GGIWA -COOH
SEQ ID NO: 23. H2N-QGVRD PGGIW AKLGA -COOH
SEQ ID NO: 24. H2N-DPGGI WAKLG AAEAS -COOH
SEQ ID NO: 25. H2N-IWAKL GAAEA SAERL -COOH
SEQ ID NO: 26. H2N-LGAAE ASAER LQGRR -COOH
SEQ ID NO: 27. H2N-EASAE RLQGR RSRGA -COOH
SEQ ID NO: 28. H2N-ERLQG RRSRG ASGSE -COOH
SEQ ID NO: 29. H2N-GRRSR GASGS EPQQM -COOH
SEQ ID NO: 30. H2N-RGASG SEPQQ MGSDV -COOH
SEQ ID NO: 31. H2N-GSEPQ QMGSD VRDLN -COOH
SEQ ID NO: 32. H2N-QQMGS DVRDL NALLP -COOH
SEQ ID NO: 33. H2N-SDVRD LNALL PAVPS -COOH
SEQ ID NO: 34. H2N-DLNAL LPAVP SLGGG -COOH
SEQ ID NO: 35. H2N-LLPAV PSLGG GGGCA -COOH
SEQ ID NO: 36. H2N-VPSLG GGGGC ALPVS -COOH
SEQ ID NO: 37. H2N-GGGGG CALPV SGAAQ -COOH
SEQ ID NO: 38. H2N-GCALP VSGAA QWAPV -COOH
SEQ ID NO: 39. H2N-PVSGA AQWAP VLDFA -COOH
SEQ ID NO: 40. H2N-AAQWA PVLDF APPGA -COOH
SEQ ID NO: 41. H2N-APVLD FAPPG ASAYG -COOH
SEQ ID NO: 42. H2N-DFAPP GASAY GSLGG -COOH
SEQ ID NO: 43. H2N-PGASA YGSLG GPAPP -COOH
SEQ ID NO: 44. H2N-AYGSL GGPAP PPAPP -COOH
SEQ ID NO: 45. H2N-LGGPA PPPAP PPPPP -COOH
SEQ ID NO: 46. H2N-APPPA PPPPP PPPPH -COOH
SEQ ID NO: 47. H2N-APPPP PPPPP HSFIK -COOH
SEQ ID NO: 48. H2N-PPPPP PHSFI KQEPS -COOH
SEQ ID NO: 49. H2N-PPHSF IKQEP SWGGA -COOH
SEQ ID NO: 50. H2N-FIKQE PSWGG AEPHE -COOH
SEQ ID NO: 51. H2N-EPSWG GAEPH EEQCL -COOH
SEQ ID NO: 52. H2N-GGAEP HEEQC LSAFT -COOH
SEQ ID NO: 53. H2N-PHEEQ CLSAF TVHFS -COOH
SEQ ID NO: 54. H2N-QCLSA FTVHF SGQFT -COOH
SEQ ID NO: 55. H2N-AFTVH FSGQF TGTAG -COOH
SEQ ID NO: 56. H2N-HFSGQ FTGTA GACRY -COOH
SEQ ID NO: 57. H2N-QFTGT AGACR YGPFG -COOH
SEQ ID NO: 58. H2N-TAGAC RYGPF GPPPP -COOH
SEQ ID NO: 59. H2N-CRYGP FGPPP PSQAS -COOH
SEQ ID NO: 60. H2N-PFGPP PPSQA SSGQA -COOH
SEQ ID NO: 61. H2N-PPPSQ ASSGQ ARMFP -COOH
SEQ ID NO: 62. H2N-QASSG QARMF PNAPY -COOH
SEQ ID NO: 63. H2N-GQARM FPNAP YLPSC -COOH
SEQ ID NO: 64. H2N-MFPNA PYLPS CLESQ -COOH
SEQ ID NO: 65. H2N-APYLP SCLES QPAIR -COOH
SEQ ID NO: 66. H2N-PSCLE SQPAI RNQGY -COOH
SEQ ID NO: 67. H2N-ESQPA IRNQG YSTVT -COOH
SEQ ID NO: 68. H2N-AIRNQ GYSTV TFDGT -COOH
SEQ ID NO: 69. H2N-QGYST VTFDG TPSYG -COOH
SEQ ID NO: 70. H2N-TVTFD GTPSY GHTPS -COOH
SEQ ID NO: 71. H2N-DGTPS YGHTP SHHAA -COOH
SEQ ID NO: 72. H2N-SYGHT PSHHA AQFPN -COOH
SEQ ID NO: 73. H2N-TPSHH AAQFP NHSFK -COOH
SEQ ID NO: 74. H2N-HAAQF PNHSF KHEDP -COOH
SEQ ID NO: 75. H2N-FPNHS FKHED PMGQQ -COOH
SEQ ID NO: 76. H2N-SFKHE DPMGQ QGSLG -COOH
SEQ ID NO: 77. H2N-EDPMG QQGSL GEQQY -COOH
SEQ ID NO: 78. H2N-GQQGS LGEQQ YSVPP -COOH
SEQ ID NO: 79. H2N-SLGEQ QYSVP PPVYG -COOH
SEQ ID NO: 80. H2N-QQYSV PPPVY GCHTP -COOH
SEQ ID NO: 81. H2N-VPPPV YGCHT PTDSC -COOH
SEQ ID NO: 82. H2N-VYGCH TPTDS CTGSQ -COOH
SEQ ID NO: 83. H2N-HTPTD SCTGS QALLL -COOH
SEQ ID NO: 84. H2N-DSCTG SQALL LRTPY -COOH
SEQ ID NO: 85. H2N-GSQAL LLRTP YSSDN -COOH
SEQ ID NO: 86. H2N-LLLRT PYSSD NLYQM -COOH
SEQ ID NO: 87. H2N-TPYSS DNLYQ MTSQL -COOH
SEQ ID NO: 88. H2N-SDNLY QMTSQ LECMT -COOH
SEQ ID NO: 89. H2N-YQMTS QLECM TWNQM -COOH
SEQ ID NO: 90. H2N-SQLEC MTWNQ MNLGA -COOH

TABLE 5-continued

Sequence of pentadecapeptides

SEQ ID NO: 91.H2N-CMTWN QMNLG ATLKG -COOH

SEQ ID NO: 92.H2N-NQMNL GATLK GVAAG -COOH

SEQ ID NO: 93.H2N-LGATL KGVAA GSSSS -COOH

SEQ ID NO: 94.H2N-LKGVA AGSSS SVKWT -COOH

SEQ ID NO: 95.H2N-AAGSS SSVKW TEGQS -COOH

SEQ ID NO: 96.H2N-SSSVK WTEGQ SNHST -COOH

SEQ ID NO: 97.H2N-KWTEG QSNHS TGYES -COOH

SEQ ID NO: 98.H2N-GQSNH STGYE SDNHT -COOH

SEQ ID NO: 99.H2N-HSTGY ESDNH TTPIL -COOH

SEQ ID NO: 100.H2N-YESDN HTTPI LCGAQ -COOH

SEQ ID NO: 101.H2N-NHTTP ILCGA QYRIH -COOH

SEQ ID NO: 102.H2N-PILCG AQYRI HTHGV -COOH

SEQ ID NO: 103.H2N-GAQYR IHTHG VFRGI -COOH

SEQ ID NO: 104.H2N-RIHTH GVFRG IQDVR -COOH

SEQ ID NO: 105.H2N-HGVFR GIQDV RRVPG -COOH

SEQ ID NO: 106.H2N-RGIQD VRRVP GVAPT -COOH

SEQ ID NO: 107.H2N-DVRRV PGVAP TLVRS -COOH

SEQ ID NO: 108.H2N-VPGVA PTLVR SASET -COOH

SEQ ID NO: 109.H2N-APTLV RSASE TSEKR -COOH

SEQ ID NO: 110.H2N-VRSAS ETSEK RPFMC -COOH

SEQ ID NO: 111.H2N-SETSE KRPFM CAYPG -COOH

SEQ ID NO: 112.H2N-EKRPF MCAYP GCNKR -COOH

SEQ ID NO: 113.H2N-FMCAY PGCNK RYFKL -COOH

SEQ ID NO: 114.H2N-YPGCN KRYFK LSHLQ -COOH

SEQ ID NO: 115.H2N-NKRYF KLSHL QMHSR -COOH

SEQ ID NO: 116.H2N-FKLSH LQMHS RKHTG -COOH

SEQ ID NO: 117.H2N-HLQMH SRKHT GEKPY -COOH

SEQ ID NO: 118.H2N-HSRKH TGEKP YQCDF -COOH

SEQ ID NO: 119.H2N-HTGEK PYQCD FKDCE -COOH

SEQ ID NO: 120.H2N-KPYQC DFKDC ERRFS -COOH

SEQ ID NO: 121.H2N-CDFKD CERRF SRSDQ-COOH

SEQ ID NO: 122.H2N-DCERR FSRSD QLKRH-COOH

SEQ ID NO: 123 H2N-RFSRS DQLKR HQRRH-COOH

SEQ ID NO: 124.H2N-SDQLK RHQRR HTGVK-COOH

SEQ ID NO: 125.H2N-KRHQR RHTGV KPFQC-COOH

SEQ ID NO: 126.H2N-RRHTG VKPFQ CKTCQ-COOH

SEQ ID NO: 127.H2N-GVKPF QCKTC QRKFS-COOH

SEQ ID NO: 128.H2N-FQCKT CQRKF SRSDH-COOH

SEQ ID NO: 129.H2N-TCQRK FSRSD HLKTH-COOH

SEQ ID NO: 130.H2N-KFSRS DHLKT HTRTH-COOH

SEQ ID NO: 131.H2N-SDHLK THTRT HTGKT-COOH

SEQ ID NO: 132.H2N-KTHTR THTGK TSEKP-COOH

SEQ ID NO: 133.H2N-RTHTG KTSEK PFSCR-COOH

SEQ ID NO: 134.H2N-GKTSE KPFSC RWPSC-COOH

SEQ ID NO: 135.H2N-EKPFS CRWPS CQKKF-COOH

SEQ ID NO: 136.H2N-SCRWP SCQKK FARSD-COOH

SEQ ID NO: 137.H2N-PSCQK KFARS DELVR-COOH

SEQ ID NO: 138.H2N-KKFAR SDELV RHHNM-COOH

SEQ ID NO: 139.H2N-RSDEL VRHHN MHQRN-COOH

SEQ ID NO: 140.H2N-LVRHH NMHQR NMTKL-COOH

SEQ ID NO: 141.H2N-HNMHQ RNMTK LQLAL-COOH

REFERENCES

1. Kolb H J, Mittermuller J, Clemm C, et al. Donor leukocyte transfusions for treatment of recurrent chronic myelogenous leukemia in marrow transplant patients. Blood. 1990; 76(12):2462-2465. Prepublished on 1990 Dec. 15 as DOI.
2. Papadopoulos E B, Ladanyi M, Emanuel D, et al. Infusions of donor leukocytes to treat Epstein-Barr virus-associated lymphoproliferative disorders after allogeneic bone marrow transplantation. N Engl J Med. 1994; 330 (17):1185-1191. Prepublished on 1994 Apr. 28 as DOI 10.1056/NEJM199404283301703.
3. Dudley M E, Wunderlich J R, Robbins P F, et al. Cancer regression and autoimmunity in patients after clonal repopulation with antitumor lymphocytes. Science. 2002; 298(5594):850-854. Prepublished on 2002 Sep. 21 as DOI 10.1126/science.1076514.
4. Rosenberg S A, Yang J C, Sherry R M, et al. Durable complete responses in heavily pretreated patients with metastatic melanoma using T-cell transfer immunotherapy. Clin Cancer Res. 2011; 17(13):4550-4557. Prepublished on 2011 Apr. 19 as DOI 10.1158/1078-0432.CCR-11-0116.
5. Yee C, Thompson J A, Byrd D, et al. Adoptive T cell therapy using antigen-specific CD8+ T cell clones for the treatment of patients with metastatic melanoma: in vivo persistence, migration, and antitumor effect of transferred T cells. Proc Natl Acad Sci USA. 2002; 99(25):16168-16173. Prepublished on 2002 Nov. 13 as DOI 10.1073/pnas.242600099.
6. Mackensen A, Meidenbauer N, Vogl S, Laumer M, Berger J, Andreesen R. Phase I study of adoptive T-cell therapy using antigen-specific CD8+ T cells for the treatment of patients with metastatic melanoma. J Clin Oncol. 2006; 24(31):5060-5069. Prepublished on 2006 Nov. 1 as DOI 10.1200/JCO.2006.07.1100.
7. Robbins P F, Morgan R A, Feldman S A, et al. Tumor regression in patients with metastatic synovial cell sarcoma and melanoma using genetically engineered lymphocytes reactive with NY-ESO-1. J Clin Oncol. 2011; 29(7):917-924. Prepublished on 2011 Feb. 2 as DOI 10.1200/JCO.2010.32.2537.

8. Morgan R A, Dudley M E, Wunderlich J R, et al. Cancer regression in patients after transfer of genetically engineered lymphocytes. Science. 2006; 314(5796):126-129. Prepublished on 2006 Sep. 2 as DOI 10.1126/science.1129003.
9. Pule M A, Savoldo B, Myers G D, et al. Virus-specific T cells engineered to coexpress tumor-specific receptors: persistence and antitumor activity in individuals with neuroblastoma. Nat Med. 2008; 14(11):1264-1270. Prepublished on 2008 Nov. 4 as DOI 10.1038/nm.1882.
10. Porter D L, Levine B L, Kalos M, Bagg A, June C H. Chimeric antigen receptor-modified T cells in chronic lymphoid leukemia. N Engl J Med. 2011; 365(8):725-733. Prepublished on 2011 Aug. 13 as DOI 10.1056/NEJMoa1103849.
11. Brentjens R J, Riviere I, Park J H, et al. Safety and persistence of adoptively transferred autologous CD19-targeted T cells in patients with relapsed or chemotherapy refractory B-cell leukemias. Blood. 2011; 118(18):4817-4828. Prepublished on 2011 Aug. 19 as DOI 10.1182/blood-2011-04-348540.
12. Gao L, Xue S A, Hasserjian R, et al. Human cytotoxic T lymphocytes specific for Wilms' tumor antigen-1 inhibit engraftment of leukemia-initiating stem cells in non-obese diabetic-severe combined immunodeficient recipients. Transplantation. 2003; 75(9):1429-1436. Prepublished on 2003 Jun. 7 as DOI 10.1097/01.TP.0000061516.57346.E8.
13. Gerber J M, Qin L, Kowalski J, et al. Characterization of chronic myeloid leukemia stem cells. Am J Hematol. 2011; 86(1):31-37. Prepublished on 2010 Dec. 7 as DOI 10.1002/ajh.21915.
14. Greiner J, Bullinger L, Guinn B A, Dohner H, Schmitt M. Leukemia-associated antigens are critical for the proliferation of acute myeloid leukemia cells. Clin Cancer Res. 2008; 14(22):7161-7166. Prepublished on 2008 Nov. 18 as DOI 10.1158/1078-0432.CCR-08-1102.
15. Call K M, Glaser T, Ito C Y, et al. Isolation and characterization of a zinc finger polypeptide gene at the human chromosome 11 Wilms' tumor locus. Cell. 1990; 60(3):509-520. Prepublished on 1990 Feb. 9 as DOI.
16. Haber D A, Sohn R L, Buckler A J, Pelletier J, Call K M, Housman D E. Alternative splicing and genomic structure of the Wilms tumor gene WT1. Proc Natl Acad Sci USA. 1991; 88(21):9618-9622. Prepublished on 1991 Nov. 1 as DOI.
17. Kreidberg J A, Sariola H, Loring J M, et al. WT1 is required for early kidney development. Cell. 1993; 74(4): 679-691. Prepublished on 1993 Aug. 27 as DOI.
18. Scharnhorst V, van der Eb A J, Jochemsen A G. WT1 proteins: functions in growth and differentiation. Gene. 2001; 273(2):141-161. Prepublished on 2001 Oct. 12 as DOI.
19. Ellisen L W, Carlesso N, Cheng T, Scadden D T, Haber D A. The Wilms tumor suppressor WT1 directs stage-specific quiescence and differentiation of human hematopoietic progenitor cells. EMBO J. 2001; 20(8): 1897-1909. Prepublished on 2001 Apr. 11 as DOI 10.1093/emboj/20.8.1897.
20. Hosen N, Sonoda Y, Oji Y, et al. Very low frequencies of human normal CD34+ haematopoietic progenitor cells express the Wilms' tumour gene WT1 at levels similar to those in leukaemia cells. Br J Haematol. 2002; 116(2): 409-420. Prepublished on 2002 Feb. 14 as DOI.
21. Yang L, Han Y, Suarez Saiz F, Minden M D. A tumor suppressor and oncogene: the WT1 story. Leukemia. 2007; 21(5):868-876. Prepublished on 2007 Mar. 16 as DOI 10.1038/sj.leu.2404624.
22. Bergmann L, Miething C, Maurer U, et al. High levels of Wilms' tumor gene (WT1) mRNA in acute myeloid leukemias are associated with a worse long-term outcome. Blood. 1997; 90(3):1217-1225. Prepublished on 1997 Aug. 1 as DOI.
23. Lapillonne H, Renneville A, Auvrignon A, et al. High WT1 expression after induction therapy predicts high risk of relapse and death in pediatric acute myeloid leukemia. J Clin Oncol. 2006; 24(10):1507-1515. Prepublished on 2006 Apr. 1 as DOI 10.1200/JCO.2005.03.5303.
24. Chen Z X, Kaeda J, Saunders S, Goldman J M. Expression patterns of WT1 and Bcr-Abl measured by TaqMan quantitative real-time RT-PCR during follow-up of leukemia patients with the Ph chromosome. Chin Med J (Engl). 2004; 117(7):968-971. Prepublished on 2004 Jul. 22 as DOI.
25. Cilloni D, Gottardi E, Messa F, et al. Significant correlation between the degree of WT1 expression and the International Prognostic Scoring System Score in patients with myelodysplastic syndromes. J Clin Oncol. 2003; 21(10):1988-1995. Prepublished on 2003 May 14 as DOI 10.1200/JCO.2003.10.503.
26. Tamaki H, Ogawa H, Ohyashiki K, et al. The Wilms' tumor gene WT1 is a good marker for diagnosis of disease progression of myelodysplastic syndromes. Leukemia. 1999; 13(3):393-399. Prepublished on 1999 Mar. 23 as DOI.
27. Keilholz U, Letsch A, Busse A, et al. A clinical and immunologic phase 2 trial of Wilms tumor gene product 1 (WT1) peptide vaccination in patients with AML and MDS. Blood. 2009; 113(26):6541-6548. Prepublished on 2009 Apr. 25 as DOI 10.1182/blood-2009-02-202598.
28. Tatsumi N, Oji Y, Tsuji N, et al. Wilms' tumor gene WT1-shRNA as a potent apoptosis-inducing agent for solid tumors. Int J Oncol. 2008; 32(3):701-711. Prepublished on 2008 Feb. 23 as DOI.
29. Ohminami H, Yasukawa M, Fujita S. HLA class I-restricted lysis of leukemia cells by a CD8(+) cytotoxic T-lymphocyte clone specific for WT1 peptide. Blood. 2000; 95(1):286-293. Prepublished on 1999 Dec. 23 as DOI.
30. Oka Y, Elisseeva O A, Tsuboi A, et al. Human cytotoxic T-lymphocyte responses specific for peptides of the wild-type Wilms' tumor gene (WT1) product. Immunogenetics. 2000; 51(2):99-107. Prepublished on 2000 Feb. 9 as DOI.
31. Rezvani K, Brenchley J M, Price D A, et al. T-cell responses directed against multiple HLA-A*0201-restricted epitopes derived from Wilms' tumor 1 protein in patients with leukemia and healthy donors: identification, quantification, and characterization. Clin Cancer Res. 2005; 11(24 Pt 1):8799-8807. Prepublished on 2005 Dec. 20 as DOI 10.1158/1078-0432.CCR-05-1314.
32. Doubrovina E S, Doubrovin M M, Lee S, et al. In vitro stimulation with WT1 peptide-loaded Epstein-Barr virus-positive B cells elicits high frequencies of WT1 peptide-specific T cells with in vitro and in vivo tumoricidal activity. Clin Cancer Res. 2004; 10(21):7207-7219. Prepublished on 2004 Nov. 10 as DOI 10.1158/1078-0432.CCR-04-1040.
33. Xue S A, Gao L, Hart D, et al. Elimination of human leukemia cells in NOD/SCID mice by WT1-TCR gene-transduced human T cells. Blood. 2005; 106(9):3062-3067. Prepublished on 2005 Jul. 16 as DOI 10.1182/blood-2005-01-0146.

34. Oka Y, Tsuboi A, Taguchi T, et al. Induction of WT1 (Wilms' tumor gene)-specific cytotoxic T lymphocytes by WT1 peptide vaccine and the resultant cancer regression. Proc Natl Acad Sci USA. 2004; 101(38):13885-13890. Prepublished on 2004 Sep. 15 as DOI 10.1073/pnas.0405884101.
35. Pinilla-Ibarz J, May R J, Korontsvit T, et al. Improved human T-cell responses against synthetic HLA-0201 analog peptides derived from the WT1 oncoprotein. Leukemia. 2006; 20(11):2025-2033. Prepublished on 2006 Sep. 23 as DOI 10.1038/sj.leu.2404380.
36. Rezvani K, Yong A S, Mielke S, et al. Leukemia-associated antigen-specific T-cell responses following combined PR1 and WT1 peptide vaccination in patients with myeloid malignancies. Blood. 2008; 111(1):236-242. Prepublished on 2007 Sep. 19 as DOI 10.1182/blood-2007-08-108241.
37. Gessler M, Poustka A, Cavenee W, Neve R L, Orkin S H, Bruns G A. Homozygous deletion in Wilms tumours of a zinc-finger gene identified by chromosome jumping. Nature. 1990; 343(6260):774-778. Prepublished on 1990 Feb. 22 as DOI 10.1038/343774a0.
38. Koehne G, Smith K M, Ferguson T L, et al. Quantitation, selection, and functional characterization of Epstein-Barr virus-specific and alloreactive T cells detected by intracellular interferon-gamma production and growth of cytotoxic precursors. Blood. 2002; 99(5):1730-1740. Prepublished on 2002 Feb. 28 as DOI.
39. Roskrow M A, Suzuki N, Gan Y, et al. Epstein-Barr virus (EBV)-specific cytotoxic T lymphocytes for the treatment of patients with EBV-positive relapsed Hodgkin's disease. Blood. 1998; 91(8):2925-2934. Prepublished on 1998 May 16 as DOI.
40. Waldrop S L, Pitcher C J, Peterson D M, Maino V C, Picker L J. Determination of antigen-specific memory/effector CD4+ T cell frequencies by flow cytometry: evidence for a novel, antigen-specific homeostatic mechanism in HIV-associated immunodeficiency. J Clin Invest. 1997; 99(7):1739-1750. Prepublished on 1997 Apr. 1 as DOI 10.1172/JCI119338.
41. Trivedi D, Williams R Y, O'Reilly R J, Koehne G. Generation of CMV-specific T lymphocytes using protein-spanning pools of pp65-derived overlapping pentadecapeptides for adoptive immunotherapy. Blood. 2005; 105(7):2793-2801. Prepublished on 2004 Oct. 30 as DOI 10.1182/blood-2003-05-1433.
42. Hasan A N, Kollen W J, Trivedi D, et al. A panel of artificial APCs expressing prevalent HLA alleles permits generation of cytotoxic T cells specific for both dominant and subdominant viral epitopes for adoptive therapy. J Immunol. 2009; 183(4):2837-2850. Prepublished on 2009 Jul. 29 as DOI 10.4049/jimmunol.0804178.
43. Gao L, Bellantuono I, Elsasser A, et al. Selective elimination of leukemic CD34(+) progenitor cells by cytotoxic T lymphocytes specific for WT1. Blood. 2000; 95(7):2198-2203. Prepublished on 2000 Mar. 25 as DOI.
44. Rammensee H, Bachmann J, Emmerich N P, Bachor O A, Stevanovic S. SYFPEITHI: database for MHC ligands and peptide motifs. Immunogenetics. 1999; 50(3-4):213-219. Prepublished on 1999 Dec. 22 as DOI.
45. Parker K C, Bednarek M A, Coligan J E. Scheme for ranking potential HLA-A2 binding peptides based on independent binding of individual peptide side-chains. J Immunol. 1994; 152(1):163-175. Prepublished on 1994 Jan. 1 as DOI.
46. Smithgall M, Misher L, Spies G, Cheever M A, Gaiger A. Identification of a novel WT1 HLA A*0201-restricted CTL epitope using whole gene in vitro priming. ASH. Orlando, Fla.: Blood; 2001:121a.
47. Cheever M A, Allison J P, Ferris A S, et al. The prioritization of cancer antigens: a national cancer institute pilot project for the acceleration of translational research. Clin Cancer Res. 2009; 15(17):5323-5337. Prepublished on 2009 Sep. 3 as DOI 10.1158/1078-0432.CCR-09-0737.
48. Kiecker F, Streitz M, Ay B, et al. Analysis of antigen-specific T-cell responses with synthetic peptides—what kind of peptide for which purpose? Hum Immunol. 2004; 65(5):523-536. Prepublished on 2004 Jun. 3 as DOI 10.1016/j.humimm.2004.02.017.
49. Pelte C, Cherepnev G, Wang Y, Schoenemann C, Volk H D, Kern F. Random screening of proteins for HLA-A*0201-binding nine-amino acid peptides is not sufficient for identifying CD8 T cell epitopes recognized in the context of HLA-A*0201. J Immunol. 2004; 172(11):6783-6789. Prepublished on 2004 May 22 as DOI.
50. Bruening W, Pelletier J. A non-AUG translational initiation event generates novel WT1 isoforms. J Biol Chem. 1996; 271(15):8646-8654. Prepublished on 1996 Apr. 12 as DOI.
51. Pittet M J, Valmori D, Dunbar P R, et al. High frequencies of naive Melan-A/MART-1-specific CD8(+) T cells in a large proportion of human histocompatibility leukocyte antigen (HLA)-A2 individuals. J Exp Med. 1999; 190(5):705-715. Prepublished on 1999 Sep. 8 as DOI.
52. Chen Q, Jackson H, Gibbs P, Davis I D, Trapani J, Cebon J. Spontaneous T cell responses to melanoma differentiation antigens from melanoma patients and healthy subjects. Cancer Immunol Immunother. 1998; 47(4):191-197. Prepublished on 1999 Jan. 6 as DOI.
53. Pittet M J, Zippelius A, Valmori D, Speiser D E, Cerottini J C, Romero P. Melan-A/MART-1-specific CD8 T cells: from thymus to tumor. Trends Immunol. 2002; 23(7):325-328. Prepublished on 2002 Jul. 10 as DOI.
54. Weber G, Karbach J, Kuci S, et al. WT1 peptide-specific T cells generated from peripheral blood of healthy donors: possible implications for adoptive immunotherapy after allogeneic stem cell transplantation. Leukemia. 2009; 23(9):1634-1642. Prepublished on 2009 Apr. 10 as DOI 10.1038/leu.2009.70.
55. Nagorsen D, Scheibenbogen C, Marincola F M, Letsch A, Keilholz U. Natural T cell immunity against cancer. Clin Cancer Res. 2003; 9(12):4296-4303. Prepublished on 2003 Oct. 14 as DOI.
56. Scheibenbogen C, Letsch A, Thiel E, et al. CD8 T-cell responses to Wilms tumor gene product WT1 and proteinase 3 in patients with acute myeloid leukemia. Blood. 2002; 100(6):2132-2137. Prepublished on 2002 Aug. 30 as DOI 10.1182/blood-2002-01-0163.
57. Elisseeva O A, Oka Y, Tsuboi A, et al. Humoral immune responses against Wilms tumor gene WT1 product in patients with hematopoietic malignancies. Blood. 2002; 99(9):3272-3279. Prepublished on 2002 Apr. 20 as DOI.
58. Tyler E, Jungbluth A A, O'Reilly R J, Koehne G. WT1-Specific Immune Responses in Patients with High-Risk Multiple Myeloma Undergoing Allogeneic T Cell-Depleted Hematopoietic Stem Cell Transplantation Followed by Donor Lymphocyte Infusions. ASH Annual Meeting Abstracts. 2011; 118(21):1993-.
59. King J W, Thomas S, Corsi F, et al. IL15 can reverse the unresponsiveness of Wilms' tumor antigen-specific CTL in patients with prostate cancer. Clin Cancer Res. 2009; 15(4):1145-1154. Prepublished on 2009 Feb. 21 as DOI 10.1158/1078-0432.CCR-08-1821.

60. Gillmore R, Xue S A, Holler A, et al. Detection of Wilms' tumor antigen—specific CTL in tumor-draining lymph nodes of patients with early breast cancer. Clin Cancer Res. 2006; 12(1):34-42. Prepublished on 2006 Jan. 7 as DOI 10.1158/1078-0432.CCR-05-1483.
61. Murao A, Oka Y, Tsuboi A, et al. High frequencies of less differentiated and more proliferative WT1-specific CD8+ T cells in bone marrow in tumor-bearing patients: an important role of bone marrow as a secondary lymphoid organ. Cancer Sci. 2010; 101(4):848-854. Prepublished on 2010 Feb. 9 as DOI 10.1111/j.1349-7006.2009.01468.x.
62. van der Bruggen P, Stroobant V, Vigneron N, van den Eynde B. Database of T-cell defined tumor antigens. http://cancerimmunity.org/peptidedatabase/Tcellepitopes.htm. Cancer Immunity. 2012.
63. Pospori C, Xue S A, Holler A, et al. Specificity for the tumor-associated self-antigen WT1 drives the development of fully functional memory T cells in the absence of vaccination. Blood. 2011; 117(25):6813-6824. Prepublished on 2011 Mar. 31 as DOI 10.1182/blood-2010-08-304568.
64. Rezvani K, Yong A S, Mielke S, et al. Repeated PR1 and WT1 peptide vaccination in Montanide-adjuvant fails to induce sustained high-avidity, epitope-specific CD8+ T cells in myeloid malignancies. Haematologica. 2011; 96(3):432-440. Prepublished on 2010 Dec. 8 as DOI 10.3324/haematol.2010.031674.
65. Lehe C, Ghebeh H, Al-Sulaiman A, et al. The Wilms' tumor antigen is a novel target for human CD4+ regulatory T cells: implications for immunotherapy. Cancer Res. 2008; 68(15):6350-6359. Prepublished on 2008 Aug. 5 as DOI 10.1158/0008-5472.CAN-08-0050.

What is claimed is:

1. An isolated WT-1 peptide consisting of an amino acid sequence selected from among AILDFLLLQ (SEQ ID NO:147), RQRPHPGAL (SEQ ID NO:142), GALRNPTAC (SEQ ID NO:143), THSPTHPPR (SEQ ID NO:146), WNQMNLGATLK (SEQ ID NO:173), PGCLQQPEQQG (SEQ ID NO:149), LDFAPPGASAY (SEQ ID NO:156), PLPHFPPSL (SEQ ID NO:144), HFPPSLPPT (SEQ ID NO:145), LLAAILDFL (SEQ ID NO:184), ALRNPTACPL (SEQ ID NO:191), GGCALPVSGA (SEQ ID NO:153), LGATLKGVAA (SEQ ID NO:176), TLGVAAGS (SEQ ID NO:177), KRPFMCAYPGC (SEQ ID NO:180) LKTHTRTHT (SEQ ID NO:182) and SEQ ID NOS:1-15.

2. An isolated WT-1 peptide consisting of 8-30 amino acids comprising an amino acid sequence selected from SEQ ID NO: 142, 143, 144, 145, 146, 147, 149 and 184.

3. The isolated WT-1 peptide of claim 1 or 2, wherein said isolated WT-1 peptide can bind to an HLA class I molecule, an HLA class II molecule, or the combination thereof.

4. A pharmaceutical composition comprising one or more peptides of claim 1 or 2 and a pharmaceutically acceptable carrier, vehicle or excipient.

5. A vaccine comprising (a) one or more isolated WT-1 peptides of claim 1 or 2 and (b) an adjuvant or a carrier.

6. The vaccine of claim 5, wherein said adjuvant is QS21, Freund's incomplete adjuvant, aluminum phosphate, aluminum hydroxide, BCG, alum, a growth factor, a cytokine, a chemokine, an interleukin, Montanide or GM-CSF.

7. The vaccine of claim 5 further comprising a cell population.

8. The vaccine of claim 7 wherein the cell population is selected from lymphocytes, monocytes, macrophages, dendritic cells, endothelial cells, stem cells or any combination thereof.

9. The vaccine of claim 7 wherein the cell population is autologous, syngeneic or allogeneic.

10. The vaccine of claim 7 wherein the population is obtained from peripheral blood, leukopheresis blood product, apheresis blood product, peripheral lymph nodes, gut associated lymphoid tissue, spleen, thymus, cord blood, mesenteric lymph nodes, liver, a site of immunologic lesions, pancreas, cerebrospinal fluid, a tumor sample, or granulomatous tissue.

11. A composition comprising (a) an antigen-presenting cell and (b) one or more peptides of claim 1 or 2.

12. The composition of claim 11 wherein the antigen-presenting cell is a dendritic cell, monocyte, macrophage, cytokine-activated monocyte or an EBV-transformed B-lymphoblastoid cell.

13. The composition of claim 11 wherein the antigen-presenting cell is from a cell line.

14. An isolated WT-1 peptide consisting of 16-30 amino acids comprising an amino acid sequence selected from SEQ ID NO:1-15.

15. A method of treating a subject with a WT-1-expressing cancer or reducing an incidence of a WT-1-expressing cancer, or its relapse, the method comprising administering to said subject one or more peptides of any one of claim 1, 2 or 14, a composition thereof, a composition thereof further comprising an antigen presenting cell, or a vaccine thereof or any combination thereof, thereby treating a subject with a WT-1-expressing cancer, reducing an incidence of a WT-1-expressing cancer or its relapse therein.

16. The method of claim 15, wherein said WT-1-expressing cancer is a leukemia, a desmoplastic small round cell tumor, a gastric cancer, a colon cancer, a lung cancer, a breast cancer, a germ cell tumor, an ovarian cancer, a uterine cancer, a thyroid cancer, a liver cancer, a renal cancer, a Kaposi's sarcoma, a sarcoma, a hepatocellular carcinoma, a Wilms' tumor, an acute myelogenous leukemia (AML), a myelodysplastic syndrome (MDS), mesothelioma or a non-small cell lung cancer (NSCLC).

17. A method of inducing the formation and proliferation of CTL specific for cells of a WT-1-expressing cancer, the method comprising administering to said subject one or more peptides of any one of claim 1, 2 or 14, a composition thereof or a vaccine thereof or any combination thereof, thereby inducing the formation and proliferation of CTL specific for cells of a WT-1-expressing cancer.

18. The method of claim 17, wherein said WT-1-expressing cancer is a leukemia, a desmoplastic small round cell tumor, a gastric cancer, a colon cancer, a lung cancer, a breast cancer, a germ cell tumor, an ovarian cancer, a uterine cancer, a thyroid cancer, a liver cancer, a renal cancer, a Kaposi's sarcoma, a sarcoma, a hepatocellular carcinoma, a Wilms' tumor, an acute myelogenous leukemia (AML), a myelodysplastic syndrome (MDS), mesothelioma or a non-small cell lung cancer (NSCLC).

19. A method of inducing formation and proliferation of (a) a WT1 protein-specific CD8+ lymphocyte; or (b) a CD4+ lymphocyte specific for the WT1 protein, or the combination thereof, the method comprising administering to a subject one or more peptides of any one of claim 1, 2 or 14, a composition thereof, a composition thereof further comprising an antigen presenting cell, or a vaccine thereof, or any combination thereof, thereby inducing formation and proliferation of (a) a WT1 protein-specific CD8+ lymphocyte; or (b) a CD4+ lymphocyte specific for the WT1 protein; or a combination thereof.

20. The method of claim 19, wherein said WT1-expressing cancer is a leukemia, a desmoplastic small round cell tumor, a gastric cancer, a colon cancer, a lung cancer, a breast cancer, a germ cell tumor, an ovarian cancer, a uterine cancer, a thyroid cancer, a liver cancer, a renal cancer, a Kaposi's sarcoma, a sarcoma, a hepatocellular carcinoma, a Wilms' tumor, an acute myelogenous leukemia (AML), a myelodysplastic syndrome (MDS), mesothelioma or a non-small cell lung cancer (NSCLC).

21. A method of inducing formation and proliferation of WT1 protein-specific cytotoxic T lymphocytes comprising contacting a lymphocyte population in vitro or ex vivo with one or more peptides selected from AILDFLLLQ (SEQ ID NO:147), RQRPHPGAL (SEQ ID NO:142), GALRNPTAC (SEQ ID NO:143), THSPTHPPR (SEQ ID NO:146), PGCLQQPEQQG (SEQ ID NO:149), LDFAPPGASAY (SEQ ID NO:156), PLPHFPPSL (SEQ ID NO:144), HFPPSLPPT (SEQ ID NO:145), LLAAILDFL (SEQ ID NO:184), ALRNPTACPL (SEQ ID NO:191), GGCALPVSGA (SEQ ID NO:153), WNQMNLGATLK (SEQ ID NO:173), LGATLKGVAA (SEQ ID NO:176), TLGVAAGS (SEQ ID NO:177), KRPFMCAYPGC (SEQ ID NO:180), LKTHTRTHT (SEQ ID NO:182), and SEQ ID NOS:1-15; or an isolated WT1 peptide consisting of 8-30 amino acids comprising an amino acid sequence selected from SEQ ID NO: 142, 143, 144, 145, 146, 147, 149, and 184; or an isolated WT1 peptide consisting of 16-30 amino acids comprising an amino acid sequence selected from SEQ ID NOS:1-15, a composition thereof, a composition thereof further comprising an antigen presenting cell, or a vaccine thereof, or any combination thereof, thereby inducing formation and proliferation of WT1 protein-specific cytotoxic T lymphocytes.

22. The method of claim 21 wherein the peptide is a pool of peptides having SEQ ID NOS:1-141.

23. A method of treating a subject with a WT1-expressing cancer or reducing an incidence of a WT1-expressing cancer, or its relapse, the method comprising administering to said subject WT1 protein-specific cytotoxic T lymphocytes obtained by the method of claim 21, thereby treating a subject with a WT1-expressing cancer, reducing an incidence of a WT1-expressing cancer or its relapse therein.

24. The method of claim 23 wherein the peptide is a pool of peptides having SEQ ID NOS:1-141.

25. A method of inducing formation and proliferation of (a) a WT1 protein-specific CD8+ lymphocyte; or (b) a CD4+ lymphocyte specific for the WT1 protein, or the combination thereof, the method comprising contacting a lymphocyte population in vitro or ex vivo with one or more peptides selected from AILDFLLLQ (SEQ ID NO:147), RQRPHPGAL (SEQ ID NO:142), GALRNPTAC (SEQ ID NO:143), THSPTHPPR (SEQ ID NO:146), PGCLQQPEQQG (SEQ ID NO:149), LDFAPPGASAY (SEQ ID NO:156), PLPHFPPSL (SEQ ID NO:144), HFPPSLPPT (SEQ ID NO:145), LLAAILDFL (SEQ ID NO:184), ALRNPTACPL (SEQ ID NO:191), GGCALPVSGA (SEQ ID NO:153), WNQMNLGATLK (SEQ ID NO:173), LGATLKGVAA (SEQ ID NO:176), TLGVAAGS (SEQ ID NO:177), KRPFMCAYPGC (SEQ ID NO:180), LKTHTRTHT (SEQ ID NO:182) and SEQ ID NOS:1-15; or an isolated WT1 peptide consisting of 8-30 amino acids comprising an amino acid sequence selected from SEQ ID NO: 142, 143, 144, 145, 146, 147, 149, and 184; or an isolated WT1 peptide consisting of 16-30 amino acids comprising an amino acid sequence selected from SEQ ID NOS:1-15, a composition thereof, a composition thereof further comprising an antigen presenting cell, or a vaccine thereof, or any combination thereof, thereby inducing formation and proliferation of (a) a WT1 protein-specific CD8+ lymphocyte; or (b) a CD4+ lymphocyte specific for the WT1 protein; or a combination thereof.

26. The method of claim 25 wherein the peptides are a pool of peptides having SEQ ID NOS:1-141.

27. A method of treating a subject with a WT1-expressing cancer, the method comprising administering to said subject WT1 protein-specific cytotoxic T lymphocytes obtained by the method of claim 25, thereby treating a subject with a WT1-expressing cancer.

28. The method of any one of claim 21, 23 or 25 wherein the lymphocyte population is obtained from a donor.

29. The method of any one of claim 21, 23 or 25 wherein the lymphocyte population is obtained from a human source.

30. The method of claim 21, 23 or 25, wherein said WT1-expressing cancer is a leukemia, a desmoplastic small round cell tumor, a gastric cancer, a colon cancer, a lung cancer, a breast cancer, a germ cell tumor, an ovarian cancer, a uterine cancer, a thyroid cancer, a liver cancer, a renal cancer, a Kaposi's sarcoma, a sarcoma, a hepatocellular carcinoma, a Wilms' tumor, an acute myelogenous leukemia (AML), a myelodysplastic syndrome (MDS), mesothelioma or a non-small cell lung cancer (NSCLC).

\* \* \* \* \*

UNITED STATES PATENT AND TRADEMARK OFFICE
CERTIFICATE OF CORRECTION

PATENT NO. : 10,100,087 B2
APPLICATION NO. : 15/608964
DATED : October 16, 2018
INVENTOR(S) : Richard J. O'Reilly et al.

Page 1 of 1

It is certified that error appears in the above-identified patent and that said Letters Patent is hereby corrected as shown below:

In the Specification

In the section marked "GOVERNMENT SUPPORT" at the top of Column 1, Lines 11-13, please replace the entire text with the following rewritten paragraph:
-- This invention was made with government support under CA008748, CA023766 and CA059350 awarded by the National Institutes of Health. The government has certain rights in the invention. --

Signed and Sealed this
Fifteenth Day of January, 2019

Andrei Iancu
*Director of the United States Patent and Trademark Office*

SEQUENCE LISTING

```
<160> NUMBER OF SEQ ID NOS: 197

<210> SEQ ID NO 1
<211> LENGTH: 15
<212> TYPE: PRT
<213> ORGANISM: Homo sapiens

<400> SEQUENCE: 1

Ser Arg Gln Arg Pro His Pro Gly Ala Leu Arg Asn Pro Thr Ala
1               5                   10                  15

<210> SEQ ID NO 2
<211> LENGTH: 15
<212> TYPE: PRT
<213> ORGANISM: Homo sapiens

<400> SEQUENCE: 2

Pro His Pro Gly Ala Leu Arg Asn Pro Thr Ala Cys Pro Leu Pro
1               5                   10                  15

<210> SEQ ID NO 3
<211> LENGTH: 15
<212> TYPE: PRT
<213> ORGANISM: Homo sapiens

<400> SEQUENCE: 3

Ala Leu Arg Asn Pro Thr Ala Cys Pro Leu Pro His Phe Pro Pro
1               5                   10                  15

<210> SEQ ID NO 4
<211> LENGTH: 15
<212> TYPE: PRT
<213> ORGANISM: Homo sapiens

<400> SEQUENCE: 4

Pro Thr Ala Cys Pro Leu Pro His Phe Pro Pro Ser Leu Pro Pro
1               5                   10                  15

<210> SEQ ID NO 5
<211> LENGTH: 15
<212> TYPE: PRT
<213> ORGANISM: Homo sapiens

<400> SEQUENCE: 5

Pro Leu Pro His Phe Pro Pro Ser Leu Pro Pro Thr His Ser Pro
1               5                   10                  15
```

<210> SEQ ID NO 6
<211> LENGTH: 15
<212> TYPE: PRT
<213> ORGANISM: Homo sapiens

<400> SEQUENCE: 6

Phe Pro Pro Ser Leu Pro Pro Thr His Ser Pro Thr His Pro Pro
1               5                   10                  15

<210> SEQ ID NO 7
<211> LENGTH: 15
<212> TYPE: PRT
<213> ORGANISM: Homo sapiens

<400> SEQUENCE: 7

Leu Pro Pro Thr His Ser Pro Thr His Pro Pro Arg Ala Gly Thr
1               5                   10                  15

<210> SEQ ID NO 8
<211> LENGTH: 15
<212> TYPE: PRT
<213> ORGANISM: Homo sapiens

<400> SEQUENCE: 8

His Ser Pro Thr His Pro Pro Arg Ala Gly Thr Ala Ala Gln Ala
1               5                   10                  15

<210> SEQ ID NO 9
<211> LENGTH: 15
<212> TYPE: PRT
<213> ORGANISM: Homo sapiens

<400> SEQUENCE: 9

His Pro Pro Arg Ala Gly Thr Ala Ala Gln Ala Pro Gly Pro Arg
1               5                   10                  15

<210> SEQ ID NO 10
<211> LENGTH: 15
<212> TYPE: PRT
<213> ORGANISM: Homo sapiens

<400> SEQUENCE: 10

Ala Gly Thr Ala Ala Gln Ala Pro Gly Pro Arg Arg Leu Leu Ala
1               5                   10                  15

<210> SEQ ID NO 11
<211> LENGTH: 15
<212> TYPE: PRT
<213> ORGANISM: Homo sapiens

<400> SEQUENCE: 11

Ala Gln Ala Pro Gly Pro Arg Arg Leu Leu Ala Ala Ile Leu Asp
1               5                   10                  15

<210> SEQ ID NO 12
<211> LENGTH: 15
<212> TYPE: PRT
<213> ORGANISM: Homo sapiens

<400> SEQUENCE: 12

Gly Pro Arg Arg Leu Leu Ala Ala Ile Leu Asp Phe Leu Leu Leu
1               5                   10                  15

<210> SEQ ID NO 13

```
<211> LENGTH: 15
<212> TYPE: PRT
<213> ORGANISM: Homo sapiens

<400> SEQUENCE: 13

Leu Leu Ala Ala Ile Leu Asp Phe Leu Leu Gln Asp Pro Ala
1               5                   10                  15

<210> SEQ ID NO 14
<211> LENGTH: 15
<212> TYPE: PRT
<213> ORGANISM: Homo sapiens

<400> SEQUENCE: 14

Ile Leu Asp Phe Leu Leu Leu Gln Asp Pro Ala Ser Thr Cys Val
1               5                   10                  15

<210> SEQ ID NO 15
<211> LENGTH: 15
<212> TYPE: PRT
<213> ORGANISM: Homo sapiens

<400> SEQUENCE: 15

Leu Leu Leu Gln Asp Pro Ala Ser Thr Cys Val Pro Glu Pro Ala
1               5                   10                  15

<210> SEQ ID NO 16
<211> LENGTH: 15
<212> TYPE: PRT
<213> ORGANISM: Homo sapiens

<400> SEQUENCE: 16

Asp Pro Ala Ser Thr Cys Val Pro Glu Pro Ala Ser Gln His Thr
1               5                   10                  15

<210> SEQ ID NO 17
<211> LENGTH: 15
<212> TYPE: PRT
<213> ORGANISM: Homo sapiens

<400> SEQUENCE: 17

Thr Cys Val Pro Glu Pro Ala Ser Gln His Thr Leu Arg Ser Gly
1               5                   10                  15

<210> SEQ ID NO 18
<211> LENGTH: 15
<212> TYPE: PRT
<213> ORGANISM: Homo sapiens

<400> SEQUENCE: 18

Glu Pro Ala Ser Gln His Thr Leu Arg Ser Gly Pro Gly Cys Leu
1               5                   10                  15

<210> SEQ ID NO 19
<211> LENGTH: 15
<212> TYPE: PRT
<213> ORGANISM: Homo sapiens

<400> SEQUENCE: 19

Gln His Thr Leu Arg Ser Gly Pro Gly Cys Leu Gln Gln Pro Glu
1               5                   10                  15

<210> SEQ ID NO 20
<211> LENGTH: 15
<212> TYPE: PRT
```

```
<213> ORGANISM: Homo sapiens

<400> SEQUENCE: 20

Arg Ser Gly Pro Gly Cys Leu Gln Gln Pro Glu Gln Gln Gly Val
1               5                   10                  15

<210> SEQ ID NO 21
<211> LENGTH: 15
<212> TYPE: PRT
<213> ORGANISM: Homo sapiens

<400> SEQUENCE: 21

Gly Cys Leu Gln Gln Pro Glu Gln Gln Gly Val Arg Asp Pro Gly
1               5                   10                  15

<210> SEQ ID NO 22
<211> LENGTH: 15
<212> TYPE: PRT
<213> ORGANISM: Homo sapiens

<400> SEQUENCE: 22

Gln Pro Glu Gln Gln Gly Val Arg Asp Pro Gly Gly Ile Trp Ala
1               5                   10                  15

<210> SEQ ID NO 23
<211> LENGTH: 15
<212> TYPE: PRT
<213> ORGANISM: Homo sapiens

<400> SEQUENCE: 23

Gln Gly Val Arg Asp Pro Gly Gly Ile Trp Ala Lys Leu Gly Ala
1               5                   10                  15

<210> SEQ ID NO 24
<211> LENGTH: 15
<212> TYPE: PRT
<213> ORGANISM: Homo sapiens

<400> SEQUENCE: 24

Asp Pro Gly Gly Ile Trp Ala Lys Leu Gly Ala Ala Glu Ala Ser
1               5                   10                  15

<210> SEQ ID NO 25
<211> LENGTH: 15
<212> TYPE: PRT
<213> ORGANISM: Homo sapiens

<400> SEQUENCE: 25

Ile Trp Ala Lys Leu Gly Ala Ala Glu Ala Ser Ala Glu Arg Leu
1               5                   10                  15

<210> SEQ ID NO 26
<211> LENGTH: 15
<212> TYPE: PRT
<213> ORGANISM: Homo sapiens

<400> SEQUENCE: 26

Leu Gly Ala Ala Glu Ala Ser Ala Glu Arg Leu Gln Gly Arg Arg
1               5                   10                  15

<210> SEQ ID NO 27
<211> LENGTH: 15
<212> TYPE: PRT
<213> ORGANISM: Homo sapiens
```

-continued

```
<400> SEQUENCE: 27

Glu Ala Ser Ala Glu Arg Leu Gln Gly Arg Arg Ser Arg Gly Ala
1               5                   10                  15

<210> SEQ ID NO 28
<211> LENGTH: 15
<212> TYPE: PRT
<213> ORGANISM: Homo sapiens

<400> SEQUENCE: 28

Glu Arg Leu Gln Gly Arg Arg Ser Arg Gly Ala Ser Gly Ser Glu
1               5                   10                  15

<210> SEQ ID NO 29
<211> LENGTH: 15
<212> TYPE: PRT
<213> ORGANISM: Homo sapiens

<400> SEQUENCE: 29

Gly Arg Arg Ser Arg Gly Ala Ser Gly Ser Glu Pro Gln Gln Met
1               5                   10                  15

<210> SEQ ID NO 30
<211> LENGTH: 15
<212> TYPE: PRT
<213> ORGANISM: Homo sapiens

<400> SEQUENCE: 30

Arg Gly Ala Ser Gly Ser Glu Pro Gln Gln Met Gly Ser Asp Val
1               5                   10                  15

<210> SEQ ID NO 31
<211> LENGTH: 15
<212> TYPE: PRT
<213> ORGANISM: Homo sapiens

<400> SEQUENCE: 31

Gly Ser Glu Pro Gln Gln Met Gly Ser Asp Val Arg Asp Leu Asn
1               5                   10                  15

<210> SEQ ID NO 32
<211> LENGTH: 15
<212> TYPE: PRT
<213> ORGANISM: Homo sapiens

<400> SEQUENCE: 32

Gln Gln Met Gly Ser Asp Val Arg Asp Leu Asn Ala Leu Leu Pro
1               5                   10                  15

<210> SEQ ID NO 33
<211> LENGTH: 15
<212> TYPE: PRT
<213> ORGANISM: Homo sapiens

<400> SEQUENCE: 33

Ser Asp Val Arg Asp Leu Asn Ala Leu Leu Pro Ala Val Pro Ser
1               5                   10                  15

<210> SEQ ID NO 34
<211> LENGTH: 15
<212> TYPE: PRT
<213> ORGANISM: Homo sapiens

<400> SEQUENCE: 34
```

Asp Leu Asn Ala Leu Leu Pro Ala Val Pro Ser Leu Gly Gly Gly
1               5                   10                  15

<210> SEQ ID NO 35
<211> LENGTH: 15
<212> TYPE: PRT
<213> ORGANISM: Homo sapiens

<400> SEQUENCE: 35

Leu Leu Pro Ala Val Pro Ser Leu Gly Gly Gly Gly Cys Ala
1               5                   10                  15

<210> SEQ ID NO 36
<211> LENGTH: 15
<212> TYPE: PRT
<213> ORGANISM: Homo sapiens

<400> SEQUENCE: 36

Val Pro Ser Leu Gly Gly Gly Gly Cys Ala Leu Pro Val Ser
1               5                   10                  15

<210> SEQ ID NO 37
<211> LENGTH: 15
<212> TYPE: PRT
<213> ORGANISM: Homo sapiens

<400> SEQUENCE: 37

Gly Gly Gly Gly Gly Cys Ala Leu Pro Val Ser Gly Ala Ala Gln
1               5                   10                  15

<210> SEQ ID NO 38
<211> LENGTH: 15
<212> TYPE: PRT
<213> ORGANISM: Homo sapiens

<400> SEQUENCE: 38

Gly Cys Ala Leu Pro Val Ser Gly Ala Ala Gln Trp Ala Pro Val
1               5                   10                  15

<210> SEQ ID NO 39
<211> LENGTH: 15
<212> TYPE: PRT
<213> ORGANISM: Homo sapiens

<400> SEQUENCE: 39

Pro Val Ser Gly Ala Ala Gln Trp Ala Pro Val Leu Asp Phe Ala
1               5                   10                  15

<210> SEQ ID NO 40
<211> LENGTH: 15
<212> TYPE: PRT
<213> ORGANISM: Homo sapiens

<400> SEQUENCE: 40

Ala Ala Gln Trp Ala Pro Val Leu Asp Phe Ala Pro Pro Gly Ala
1               5                   10                  15

<210> SEQ ID NO 41
<211> LENGTH: 15
<212> TYPE: PRT
<213> ORGANISM: Homo sapiens

<400> SEQUENCE: 41

Ala Pro Val Leu Asp Phe Ala Pro Pro Gly Ala Ser Ala Tyr Gly
1               5                   10                  15

```
<210> SEQ ID NO 42
<211> LENGTH: 15
<212> TYPE: PRT
<213> ORGANISM: Homo sapiens

<400> SEQUENCE: 42

Asp Phe Ala Pro Pro Gly Ala Ser Ala Tyr Gly Ser Leu Gly Gly
1               5                   10                  15

<210> SEQ ID NO 43
<211> LENGTH: 15
<212> TYPE: PRT
<213> ORGANISM: Homo sapiens

<400> SEQUENCE: 43

Pro Gly Ala Ser Ala Tyr Gly Ser Leu Gly Gly Pro Ala Pro Pro
1               5                   10                  15

<210> SEQ ID NO 44
<211> LENGTH: 15
<212> TYPE: PRT
<213> ORGANISM: Homo sapiens

<400> SEQUENCE: 44

Ala Tyr Gly Ser Leu Gly Gly Pro Ala Pro Pro Pro Ala Pro Pro
1               5                   10                  15

<210> SEQ ID NO 45
<211> LENGTH: 15
<212> TYPE: PRT
<213> ORGANISM: Homo sapiens

<400> SEQUENCE: 45

Leu Gly Gly Pro Ala Pro Pro Ala Pro Pro Pro Ala Pro Pro Pro
1               5                   10                  15

<210> SEQ ID NO 46
<211> LENGTH: 15
<212> TYPE: PRT
<213> ORGANISM: Homo sapiens

<400> SEQUENCE: 46

Ala Pro Pro Pro Ala Pro Pro Pro Pro Pro Pro Pro Pro Pro His
1               5                   10                  15

<210> SEQ ID NO 47
<211> LENGTH: 15
<212> TYPE: PRT
<213> ORGANISM: Homo sapiens

<400> SEQUENCE: 47

Ala Pro Pro Pro Pro Pro Pro Pro Pro His Ser Phe Ile Lys
1               5                   10                  15

<210> SEQ ID NO 48
<211> LENGTH: 15
<212> TYPE: PRT
<213> ORGANISM: Homo sapiens

<400> SEQUENCE: 48

Pro Pro Pro Pro Pro His Ser Phe Ile Lys Gln Glu Pro Ser
1               5                   10                  15
```

<210> SEQ ID NO 49
<211> LENGTH: 15
<212> TYPE: PRT
<213> ORGANISM: Homo sapiens

<400> SEQUENCE: 49

Pro Pro His Ser Phe Ile Lys Gln Glu Pro Ser Trp Gly Gly Ala
1               5                   10                  15

<210> SEQ ID NO 50
<211> LENGTH: 15
<212> TYPE: PRT
<213> ORGANISM: Homo sapiens

<400> SEQUENCE: 50

Phe Ile Lys Gln Glu Pro Ser Trp Gly Gly Ala Glu Pro His Glu
1               5                   10                  15

<210> SEQ ID NO 51
<211> LENGTH: 15
<212> TYPE: PRT
<213> ORGANISM: Homo sapiens

<400> SEQUENCE: 51

Glu Pro Ser Trp Gly Gly Ala Glu Pro His Glu Gln Cys Leu
1               5                   10                  15

<210> SEQ ID NO 52
<211> LENGTH: 15
<212> TYPE: PRT
<213> ORGANISM: Homo sapiens

<400> SEQUENCE: 52

Gly Gly Ala Glu Pro His Glu Gln Cys Leu Ser Ala Phe Thr
1               5                   10                  15

<210> SEQ ID NO 53
<211> LENGTH: 15
<212> TYPE: PRT
<213> ORGANISM: Homo sapiens

<400> SEQUENCE: 53

Pro His Glu Glu Gln Cys Leu Ser Ala Phe Thr Val His Phe Ser
1               5                   10                  15

<210> SEQ ID NO 54
<211> LENGTH: 15
<212> TYPE: PRT
<213> ORGANISM: Homo sapiens

<400> SEQUENCE: 54

Gln Cys Leu Ser Ala Phe Thr Val His Phe Ser Gly Gln Phe Thr
1               5                   10                  15

<210> SEQ ID NO 55
<211> LENGTH: 15
<212> TYPE: PRT
<213> ORGANISM: Homo sapiens

<400> SEQUENCE: 55

Ala Phe Thr Val His Phe Ser Gly Gln Phe Thr Gly Thr Ala Gly
1               5                   10                  15

<210> SEQ ID NO 56
<211> LENGTH: 15

```
<212> TYPE: PRT
<213> ORGANISM: Homo sapiens

<400> SEQUENCE: 56

His Phe Ser Gly Gln Phe Thr Gly Thr Ala Gly Ala Cys Arg Tyr
1               5                   10                  15

<210> SEQ ID NO 57
<211> LENGTH: 15
<212> TYPE: PRT
<213> ORGANISM: Homo sapiens

<400> SEQUENCE: 57

Gln Phe Thr Gly Thr Ala Gly Ala Cys Arg Tyr Gly Pro Phe Gly
1               5                   10                  15

<210> SEQ ID NO 58
<211> LENGTH: 15
<212> TYPE: PRT
<213> ORGANISM: Homo sapiens

<400> SEQUENCE: 58

Thr Ala Gly Ala Cys Arg Tyr Gly Pro Phe Gly Pro Pro Pro Pro
1               5                   10                  15

<210> SEQ ID NO 59
<211> LENGTH: 15
<212> TYPE: PRT
<213> ORGANISM: Homo sapiens

<400> SEQUENCE: 59

Cys Arg Tyr Gly Pro Phe Gly Pro Pro Pro Pro Ser Gln Ala Ser
1               5                   10                  15

<210> SEQ ID NO 60
<211> LENGTH: 15
<212> TYPE: PRT
<213> ORGANISM: Homo sapiens

<400> SEQUENCE: 60

Pro Phe Gly Pro Pro Pro Pro Ser Gln Ala Ser Ser Gly Gln Ala
1               5                   10                  15

<210> SEQ ID NO 61
<211> LENGTH: 15
<212> TYPE: PRT
<213> ORGANISM: Homo sapiens

<400> SEQUENCE: 61

Pro Pro Pro Ser Gln Ala Ser Ser Gly Gln Ala Arg Met Phe Pro
1               5                   10                  15

<210> SEQ ID NO 62
<211> LENGTH: 15
<212> TYPE: PRT
<213> ORGANISM: Homo sapiens

<400> SEQUENCE: 62

Gln Ala Ser Ser Gly Gln Ala Arg Met Phe Pro Asn Ala Pro Tyr
1               5                   10                  15

<210> SEQ ID NO 63
<211> LENGTH: 15
<212> TYPE: PRT
<213> ORGANISM: Homo sapiens
```

<400> SEQUENCE: 63

Gly Gln Ala Arg Met Phe Pro Asn Ala Pro Tyr Leu Pro Ser Cys
1               5                   10                  15

<210> SEQ ID NO 64
<211> LENGTH: 15
<212> TYPE: PRT
<213> ORGANISM: Homo sapiens

<400> SEQUENCE: 64

Met Phe Pro Asn Ala Pro Tyr Leu Pro Ser Cys Leu Glu Ser Gln
1               5                   10                  15

<210> SEQ ID NO 65
<211> LENGTH: 15
<212> TYPE: PRT
<213> ORGANISM: Homo sapiens

<400> SEQUENCE: 65

Ala Pro Tyr Leu Pro Ser Cys Leu Glu Ser Gln Pro Ala Ile Arg
1               5                   10                  15

<210> SEQ ID NO 66
<211> LENGTH: 15
<212> TYPE: PRT
<213> ORGANISM: Homo sapiens

<400> SEQUENCE: 66

Pro Ser Cys Leu Glu Ser Gln Pro Ala Ile Arg Asn Gln Gly Tyr
1               5                   10                  15

<210> SEQ ID NO 67
<211> LENGTH: 15
<212> TYPE: PRT
<213> ORGANISM: Homo sapiens

<400> SEQUENCE: 67

Glu Ser Gln Pro Ala Ile Arg Asn Gln Gly Tyr Ser Thr Val Thr
1               5                   10                  15

<210> SEQ ID NO 68
<211> LENGTH: 15
<212> TYPE: PRT
<213> ORGANISM: Homo sapiens

<400> SEQUENCE: 68

Ala Ile Arg Asn Gln Gly Tyr Ser Thr Val Thr Phe Asp Gly Thr
1               5                   10                  15

<210> SEQ ID NO 69
<211> LENGTH: 15
<212> TYPE: PRT
<213> ORGANISM: Homo sapiens

<400> SEQUENCE: 69

Gln Gly Tyr Ser Thr Val Thr Phe Asp Gly Thr Pro Ser Tyr Gly
1               5                   10                  15

<210> SEQ ID NO 70
<211> LENGTH: 15
<212> TYPE: PRT
<213> ORGANISM: Homo sapiens

<400> SEQUENCE: 70

```
Thr Val Thr Phe Asp Gly Thr Pro Ser Tyr Gly His Thr Pro Ser
1               5                   10                  15

<210> SEQ ID NO 71
<211> LENGTH: 15
<212> TYPE: PRT
<213> ORGANISM: Homo sapiens

<400> SEQUENCE: 71

Asp Gly Thr Pro Ser Tyr Gly His Thr Pro Ser His His Ala Ala
1               5                   10                  15

<210> SEQ ID NO 72
<211> LENGTH: 15
<212> TYPE: PRT
<213> ORGANISM: Homo sapiens

<400> SEQUENCE: 72

Ser Tyr Gly His Thr Pro Ser His His Ala Ala Gln Phe Pro Asn
1               5                   10                  15

<210> SEQ ID NO 73
<211> LENGTH: 15
<212> TYPE: PRT
<213> ORGANISM: Homo sapiens

<400> SEQUENCE: 73

Thr Pro Ser His His Ala Ala Gln Phe Pro Asn His Ser Phe Lys
1               5                   10                  15

<210> SEQ ID NO 74
<211> LENGTH: 15
<212> TYPE: PRT
<213> ORGANISM: Homo sapiens

<400> SEQUENCE: 74

His Ala Ala Gln Phe Pro Asn His Ser Phe Lys His Glu Asp Pro
1               5                   10                  15

<210> SEQ ID NO 75
<211> LENGTH: 15
<212> TYPE: PRT
<213> ORGANISM: Homo sapiens

<400> SEQUENCE: 75

Phe Pro Asn His Ser Phe Lys His Glu Asp Pro Met Gly Gln Gln
1               5                   10                  15

<210> SEQ ID NO 76
<211> LENGTH: 15
<212> TYPE: PRT
<213> ORGANISM: Homo sapiens

<400> SEQUENCE: 76

Ser Phe Lys His Glu Asp Pro Met Gly Gln Gln Gly Ser Leu Gly
1               5                   10                  15

<210> SEQ ID NO 77
<211> LENGTH: 15
<212> TYPE: PRT
<213> ORGANISM: Homo sapiens

<400> SEQUENCE: 77

Glu Asp Pro Met Gly Gln Gln Gly Ser Leu Gly Glu Gln Gln Tyr
```

<210> SEQ ID NO 78
<211> LENGTH: 15
<212> TYPE: PRT
<213> ORGANISM: Homo sapiens

<400> SEQUENCE: 78

Gly Gln Gln Gly Ser Leu Gly Glu Gln Gln Tyr Ser Val Pro Pro
1               5                   10                  15

<210> SEQ ID NO 79
<211> LENGTH: 15
<212> TYPE: PRT
<213> ORGANISM: Homo sapiens

<400> SEQUENCE: 79

Ser Leu Gly Glu Gln Gln Tyr Ser Val Pro Pro Val Tyr Gly
1               5                   10                  15

<210> SEQ ID NO 80
<211> LENGTH: 15
<212> TYPE: PRT
<213> ORGANISM: Homo sapiens

<400> SEQUENCE: 80

Gln Gln Tyr Ser Val Pro Pro Val Tyr Gly Cys His Thr Pro
1               5                   10                  15

<210> SEQ ID NO 81
<211> LENGTH: 15
<212> TYPE: PRT
<213> ORGANISM: Homo sapiens

<400> SEQUENCE: 81

Val Pro Pro Pro Val Tyr Gly Cys His Thr Pro Thr Asp Ser Cys
1               5                   10                  15

<210> SEQ ID NO 82
<211> LENGTH: 15
<212> TYPE: PRT
<213> ORGANISM: Homo sapiens

<400> SEQUENCE: 82

Val Tyr Gly Cys His Thr Pro Thr Asp Ser Cys Thr Gly Ser Gln
1               5                   10                  15

<210> SEQ ID NO 83
<211> LENGTH: 15
<212> TYPE: PRT
<213> ORGANISM: Homo sapiens

<400> SEQUENCE: 83

His Thr Pro Thr Asp Ser Cys Thr Gly Ser Gln Ala Leu Leu Leu
1               5                   10                  15

<210> SEQ ID NO 84
<211> LENGTH: 15
<212> TYPE: PRT
<213> ORGANISM: Homo sapiens

<400> SEQUENCE: 84

Asp Ser Cys Thr Gly Ser Gln Ala Leu Leu Leu Arg Thr Pro Tyr
1               5                   10                  15

<210> SEQ ID NO 85
<211> LENGTH: 15
<212> TYPE: PRT
<213> ORGANISM: Homo sapiens

<400> SEQUENCE: 85

Gly Ser Gln Ala Leu Leu Leu Arg Thr Pro Tyr Ser Ser Asp Asn
1               5                   10                  15

<210> SEQ ID NO 86
<211> LENGTH: 15
<212> TYPE: PRT
<213> ORGANISM: Homo sapiens

<400> SEQUENCE: 86

Leu Leu Leu Arg Thr Pro Tyr Ser Ser Asp Asn Leu Tyr Gln Met
1               5                   10                  15

<210> SEQ ID NO 87
<211> LENGTH: 15
<212> TYPE: PRT
<213> ORGANISM: Homo sapiens

<400> SEQUENCE: 87

Thr Pro Tyr Ser Ser Asp Asn Leu Tyr Gln Met Thr Ser Gln Leu
1               5                   10                  15

<210> SEQ ID NO 88
<211> LENGTH: 15
<212> TYPE: PRT
<213> ORGANISM: Homo sapiens

<400> SEQUENCE: 88

Ser Asp Asn Leu Tyr Gln Met Thr Ser Gln Leu Glu Cys Met Thr
1               5                   10                  15

<210> SEQ ID NO 89
<211> LENGTH: 15
<212> TYPE: PRT
<213> ORGANISM: Homo sapiens

<400> SEQUENCE: 89

Tyr Gln Met Thr Ser Gln Leu Glu Cys Met Thr Trp Asn Gln Met
1               5                   10                  15

<210> SEQ ID NO 90
<211> LENGTH: 15
<212> TYPE: PRT
<213> ORGANISM: Homo sapiens

<400> SEQUENCE: 90

Ser Gln Leu Glu Cys Met Thr Trp Asn Gln Met Asn Leu Gly Ala
1               5                   10                  15

<210> SEQ ID NO 91
<211> LENGTH: 15
<212> TYPE: PRT
<213> ORGANISM: Homo sapiens

<400> SEQUENCE: 91

Cys Met Thr Trp Asn Gln Met Asn Leu Gly Ala Thr Leu Lys Gly
1               5                   10                  15

<210> SEQ ID NO 92

```
<211> LENGTH: 15
<212> TYPE: PRT
<213> ORGANISM: Homo sapiens

<400> SEQUENCE: 92

Asn Gln Met Asn Leu Gly Ala Thr Leu Lys Gly Val Ala Ala Gly
1               5                   10                  15

<210> SEQ ID NO 93
<211> LENGTH: 15
<212> TYPE: PRT
<213> ORGANISM: Homo sapiens

<400> SEQUENCE: 93

Leu Gly Ala Thr Leu Lys Gly Val Ala Ala Gly Ser Ser Ser
1               5                   10                  15

<210> SEQ ID NO 94
<211> LENGTH: 15
<212> TYPE: PRT
<213> ORGANISM: Homo sapiens

<400> SEQUENCE: 94

Leu Lys Gly Val Ala Ala Gly Ser Ser Ser Val Lys Trp Thr
1               5                   10                  15

<210> SEQ ID NO 95
<211> LENGTH: 15
<212> TYPE: PRT
<213> ORGANISM: Homo sapiens

<400> SEQUENCE: 95

Ala Ala Gly Ser Ser Ser Ser Val Lys Trp Thr Glu Gly Gln Ser
1               5                   10                  15

<210> SEQ ID NO 96
<211> LENGTH: 15
<212> TYPE: PRT
<213> ORGANISM: Homo sapiens

<400> SEQUENCE: 96

Ser Ser Ser Val Lys Trp Thr Glu Gly Gln Ser Asn His Ser Thr
1               5                   10                  15

<210> SEQ ID NO 97
<211> LENGTH: 15
<212> TYPE: PRT
<213> ORGANISM: Homo sapiens

<400> SEQUENCE: 97

Lys Trp Thr Glu Gly Gln Ser Asn His Ser Thr Gly Tyr Glu Ser
1               5                   10                  15

<210> SEQ ID NO 98
<211> LENGTH: 15
<212> TYPE: PRT
<213> ORGANISM: Homo sapiens

<400> SEQUENCE: 98

Gly Gln Ser Asn His Ser Thr Gly Tyr Glu Ser Asp Asn His Thr
1               5                   10                  15

<210> SEQ ID NO 99
<211> LENGTH: 15
<212> TYPE: PRT
```

<213> ORGANISM: Homo sapiens

<400> SEQUENCE: 99

His Ser Thr Gly Tyr Glu Ser Asp Asn His Thr Thr Pro Ile Leu
1               5                   10                  15

<210> SEQ ID NO 100
<211> LENGTH: 15
<212> TYPE: PRT
<213> ORGANISM: Homo sapiens

<400> SEQUENCE: 100

Tyr Glu Ser Asp Asn His Thr Thr Pro Ile Leu Cys Gly Ala Gln
1               5                   10                  15

<210> SEQ ID NO 101
<211> LENGTH: 15
<212> TYPE: PRT
<213> ORGANISM: Homo sapiens

<400> SEQUENCE: 101

Asn His Thr Thr Pro Ile Leu Cys Gly Ala Gln Tyr Arg Ile His
1               5                   10                  15

<210> SEQ ID NO 102
<211> LENGTH: 15
<212> TYPE: PRT
<213> ORGANISM: Homo sapiens

<400> SEQUENCE: 102

Pro Ile Leu Cys Gly Ala Gln Tyr Arg Ile His Thr His Gly Val
1               5                   10                  15

<210> SEQ ID NO 103
<211> LENGTH: 15
<212> TYPE: PRT
<213> ORGANISM: Homo sapiens

<400> SEQUENCE: 103

Gly Ala Gln Tyr Arg Ile His Thr His Gly Val Phe Arg Gly Ile
1               5                   10                  15

<210> SEQ ID NO 104
<211> LENGTH: 15
<212> TYPE: PRT
<213> ORGANISM: Homo sapiens

<400> SEQUENCE: 104

Arg Ile His Thr His Gly Val Phe Arg Gly Ile Gln Asp Val Arg
1               5                   10                  15

<210> SEQ ID NO 105
<211> LENGTH: 15
<212> TYPE: PRT
<213> ORGANISM: Homo sapiens

<400> SEQUENCE: 105

His Gly Val Phe Arg Gly Ile Gln Asp Val Arg Arg Val Pro Gly
1               5                   10                  15

<210> SEQ ID NO 106
<211> LENGTH: 15
<212> TYPE: PRT
<213> ORGANISM: Homo sapiens -continued

```
<400> SEQUENCE: 106

Arg Gly Ile Gln Asp Val Arg Arg Val Pro Gly Val Ala Pro Thr
1               5                   10                  15

<210> SEQ ID NO 107
<211> LENGTH: 15
<212> TYPE: PRT
<213> ORGANISM: Homo sapiens

<400> SEQUENCE: 107

Asp Val Arg Arg Val Pro Gly Val Ala Pro Thr Leu Val Arg Ser
1               5                   10                  15

<210> SEQ ID NO 108
<211> LENGTH: 15
<212> TYPE: PRT
<213> ORGANISM: Homo sapiens

<400> SEQUENCE: 108

Val Pro Gly Val Ala Pro Thr Leu Val Arg Ser Ala Ser Glu Thr
1               5                   10                  15

<210> SEQ ID NO 109
<211> LENGTH: 15
<212> TYPE: PRT
<213> ORGANISM: Homo sapiens

<400> SEQUENCE: 109

Ala Pro Thr Leu Val Arg Ser Ala Ser Glu Thr Ser Glu Lys Arg
1               5                   10                  15

<210> SEQ ID NO 110
<211> LENGTH: 15
<212> TYPE: PRT
<213> ORGANISM: Homo sapiens

<400> SEQUENCE: 110

Val Arg Ser Ala Ser Glu Thr Ser Glu Lys Arg Pro Phe Met Cys
1               5                   10                  15

<210> SEQ ID NO 111
<211> LENGTH: 15
<212> TYPE: PRT
<213> ORGANISM: Homo sapiens

<400> SEQUENCE: 111

Ser Glu Thr Ser Glu Lys Arg Pro Phe Met Cys Ala Tyr Pro Gly
1               5                   10                  15

<210> SEQ ID NO 112
<211> LENGTH: 15
<212> TYPE: PRT
<213> ORGANISM: Homo sapiens

<400> SEQUENCE: 112

Glu Lys Arg Pro Phe Met Cys Ala Tyr Pro Gly Cys Asn Lys Arg
1               5                   10                  15

<210> SEQ ID NO 113
<211> LENGTH: 15
<212> TYPE: PRT
<213> ORGANISM: Homo sapiens

<400> SEQUENCE: 113
```

```
Phe Met Cys Ala Tyr Pro Gly Cys Asn Lys Arg Tyr Phe Lys Leu
1               5                   10                  15
```

<210> SEQ ID NO 114
<211> LENGTH: 15
<212> TYPE: PRT
<213> ORGANISM: Homo sapiens

<400> SEQUENCE: 114

```
Tyr Pro Gly Cys Asn Lys Arg Tyr Phe Lys Leu Ser His Leu Gln
1               5                   10                  15
```

<210> SEQ ID NO 115
<211> LENGTH: 15
<212> TYPE: PRT
<213> ORGANISM: Homo sapiens

<400> SEQUENCE: 115

```
Asn Lys Arg Tyr Phe Lys Leu Ser His Leu Gln Met His Ser Arg
1               5                   10                  15
```

<210> SEQ ID NO 116
<211> LENGTH: 15
<212> TYPE: PRT
<213> ORGANISM: Homo sapiens

<400> SEQUENCE: 116

```
Phe Lys Leu Ser His Leu Gln Met His Ser Arg Lys His Thr Gly
1               5                   10                  15
```

<210> SEQ ID NO 117
<211> LENGTH: 15
<212> TYPE: PRT
<213> ORGANISM: Homo sapiens

<400> SEQUENCE: 117

```
His Leu Gln Met His Ser Arg Lys His Thr Gly Glu Lys Pro Tyr
1               5                   10                  15
```

<210> SEQ ID NO 118
<211> LENGTH: 15
<212> TYPE: PRT
<213> ORGANISM: Homo sapiens

<400> SEQUENCE: 118

```
His Ser Arg Lys His Thr Gly Glu Lys Pro Tyr Gln Cys Asp Phe
1               5                   10                  15
```

<210> SEQ ID NO 119
<211> LENGTH: 15
<212> TYPE: PRT
<213> ORGANISM: Homo sapiens

<400> SEQUENCE: 119

```
His Thr Gly Glu Lys Pro Tyr Gln Cys Asp Phe Lys Asp Cys Glu
1               5                   10                  15
```

<210> SEQ ID NO 120
<211> LENGTH: 15
<212> TYPE: PRT
<213> ORGANISM: Homo sapiens

<400> SEQUENCE: 120

```
Lys Pro Tyr Gln Cys Asp Phe Lys Asp Cys Glu Arg Arg Phe Ser
1               5                   10                  15
```

<210> SEQ ID NO 121
<211> LENGTH: 15
<212> TYPE: PRT
<213> ORGANISM: Homo sapiens

<400> SEQUENCE: 121

Cys Asp Phe Lys Asp Cys Glu Arg Arg Phe Ser Arg Ser Asp Gln
1               5                   10                  15

<210> SEQ ID NO 122
<211> LENGTH: 15
<212> TYPE: PRT
<213> ORGANISM: Homo sapiens

<400> SEQUENCE: 122

Asp Cys Glu Arg Arg Phe Ser Arg Ser Asp Gln Leu Lys Arg His
1               5                   10                  15

<210> SEQ ID NO 123
<211> LENGTH: 15
<212> TYPE: PRT
<213> ORGANISM: Homo sapiens

<400> SEQUENCE: 123

Arg Phe Ser Arg Ser Asp Gln Leu Lys Arg His Gln Arg Arg His
1               5                   10                  15

<210> SEQ ID NO 124
<211> LENGTH: 15
<212> TYPE: PRT
<213> ORGANISM: Homo sapiens

<400> SEQUENCE: 124

Ser Asp Gln Leu Lys Arg His Gln Arg Arg His Thr Gly Val Lys
1               5                   10                  15

<210> SEQ ID NO 125
<211> LENGTH: 15
<212> TYPE: PRT
<213> ORGANISM: Homo sapiens

<400> SEQUENCE: 125

Lys Arg His Gln Arg Arg His Thr Gly Val Lys Pro Phe Gln Cys
1               5                   10                  15

<210> SEQ ID NO 126
<211> LENGTH: 15
<212> TYPE: PRT
<213> ORGANISM: Homo sapiens

<400> SEQUENCE: 126

Arg Arg His Thr Gly Val Lys Pro Phe Gln Cys Lys Thr Cys Gln
1               5                   10                  15

<210> SEQ ID NO 127
<211> LENGTH: 15
<212> TYPE: PRT
<213> ORGANISM: Homo sapiens

<400> SEQUENCE: 127

Gly Val Lys Pro Phe Gln Cys Lys Thr Cys Gln Arg Lys Phe Ser
1               5                   10                  15

```
<210> SEQ ID NO 128
<211> LENGTH: 15
<212> TYPE: PRT
<213> ORGANISM: Homo sapiens

<400> SEQUENCE: 128

Phe Gln Cys Lys Thr Cys Gln Arg Lys Phe Ser Arg Ser Asp His
1               5                   10                  15

<210> SEQ ID NO 129
<211> LENGTH: 15
<212> TYPE: PRT
<213> ORGANISM: Homo sapiens

<400> SEQUENCE: 129

Thr Cys Gln Arg Lys Phe Ser Arg Ser Asp His Leu Lys Thr His
1               5                   10                  15

<210> SEQ ID NO 130
<211> LENGTH: 15
<212> TYPE: PRT
<213> ORGANISM: Homo sapiens

<400> SEQUENCE: 130

Lys Phe Ser Arg Ser Asp His Leu Lys Thr His Thr Arg Thr His
1               5                   10                  15

<210> SEQ ID NO 131
<211> LENGTH: 15
<212> TYPE: PRT
<213> ORGANISM: Homo sapiens

<400> SEQUENCE: 131

Ser Asp His Leu Lys Thr His Thr Arg Thr His Thr Gly Lys Thr
1               5                   10                  15

<210> SEQ ID NO 132
<211> LENGTH: 15
<212> TYPE: PRT
<213> ORGANISM: Homo sapiens

<400> SEQUENCE: 132

Lys Thr His Thr Arg Thr His Thr Gly Lys Thr Ser Glu Lys Pro
1               5                   10                  15

<210> SEQ ID NO 133
<211> LENGTH: 15
<212> TYPE: PRT
<213> ORGANISM: Homo sapiens

<400> SEQUENCE: 133

Arg Thr His Thr Gly Lys Thr Ser Glu Lys Pro Phe Ser Cys Arg
1               5                   10                  15

<210> SEQ ID NO 134
<211> LENGTH: 15
<212> TYPE: PRT
<213> ORGANISM: Homo sapiens

<400> SEQUENCE: 134

Gly Lys Thr Ser Glu Lys Pro Phe Ser Cys Arg Trp Pro Ser Cys
1               5                   10                  15

<210> SEQ ID NO 135
<211> LENGTH: 15
```

```
<212> TYPE: PRT
<213> ORGANISM: Homo sapiens

<400> SEQUENCE: 135

Glu Lys Pro Phe Ser Cys Arg Trp Pro Ser Cys Gln Lys Lys Phe
1               5                   10                  15

<210> SEQ ID NO 136
<211> LENGTH: 15
<212> TYPE: PRT
<213> ORGANISM: Homo sapiens

<400> SEQUENCE: 136

Ser Cys Arg Trp Pro Ser Cys Gln Lys Lys Phe Ala Arg Ser Asp
1               5                   10                  15

<210> SEQ ID NO 137
<211> LENGTH: 15
<212> TYPE: PRT
<213> ORGANISM: Homo sapiens

<400> SEQUENCE: 137

Pro Ser Cys Gln Lys Lys Phe Ala Arg Ser Asp Glu Leu Val Arg
1               5                   10                  15

<210> SEQ ID NO 138
<211> LENGTH: 15
<212> TYPE: PRT
<213> ORGANISM: Homo sapiens

<400> SEQUENCE: 138

Lys Lys Phe Ala Arg Ser Asp Glu Leu Val Arg His His Asn Met
1               5                   10                  15

<210> SEQ ID NO 139
<211> LENGTH: 15
<212> TYPE: PRT
<213> ORGANISM: Homo sapiens

<400> SEQUENCE: 139

Arg Ser Asp Glu Leu Val Arg His His Asn Met His Gln Arg Asn
1               5                   10                  15

<210> SEQ ID NO 140
<211> LENGTH: 15
<212> TYPE: PRT
<213> ORGANISM: Homo sapiens

<400> SEQUENCE: 140

Leu Val Arg His His Asn Met His Gln Arg Asn Met Thr Lys Leu
1               5                   10                  15

<210> SEQ ID NO 141
<211> LENGTH: 15
<212> TYPE: PRT
<213> ORGANISM: Homo sapiens

<400> SEQUENCE: 141

His Asn Met His Gln Arg Asn Met Thr Lys Leu Gln Leu Ala Leu
1               5                   10                  15

<210> SEQ ID NO 142
<211> LENGTH: 9
<212> TYPE: PRT
<213> ORGANISM: Homo sapiens
```

```
<400> SEQUENCE: 142

Arg Gln Arg Pro His Pro Gly Ala Leu
1               5

<210> SEQ ID NO 143
<211> LENGTH: 9
<212> TYPE: PRT
<213> ORGANISM: Homo sapiens

<400> SEQUENCE: 143

Gly Ala Leu Arg Asn Pro Thr Ala Cys
1               5

<210> SEQ ID NO 144
<211> LENGTH: 9
<212> TYPE: PRT
<213> ORGANISM: Homo sapiens

<400> SEQUENCE: 144

Pro Leu Pro His Phe Pro Pro Ser Leu
1               5

<210> SEQ ID NO 145
<211> LENGTH: 9
<212> TYPE: PRT
<213> ORGANISM: Homo sapiens

<400> SEQUENCE: 145

His Phe Pro Pro Ser Leu Pro Pro Thr
1               5

<210> SEQ ID NO 146
<211> LENGTH: 9
<212> TYPE: PRT
<213> ORGANISM: Homo sapiens

<400> SEQUENCE: 146

Thr His Ser Pro Thr His Pro Pro Arg
1               5

<210> SEQ ID NO 147
<211> LENGTH: 9
<212> TYPE: PRT
<213> ORGANISM: Homo sapiens

<400> SEQUENCE: 147

Ala Ile Leu Asp Phe Leu Leu Leu Gln
1               5

<210> SEQ ID NO 148
<211> LENGTH: 9
<212> TYPE: PRT
<213> ORGANISM: Homo sapiens

<400> SEQUENCE: 148

Pro Gly Cys Leu Gln Gln Pro Glu Gln
1               5

<210> SEQ ID NO 149
<211> LENGTH: 11
<212> TYPE: PRT
<213> ORGANISM: Homo sapiens

<400> SEQUENCE: 149
```

Pro Gly Cys Leu Gln Gln Pro Glu Gln Gln Gly
1               5                   10

<210> SEQ ID NO 150
<211> LENGTH: 9
<212> TYPE: PRT
<213> ORGANISM: Homo sapiens

<400> SEQUENCE: 150

Lys Leu Gly Ala Ala Glu Ala Ser Ala
1               5

<210> SEQ ID NO 151
<211> LENGTH: 9
<212> TYPE: PRT
<213> ORGANISM: Homo sapiens

<400> SEQUENCE: 151

Ala Ser Gly Ser Glu Pro Gln Gln Met
1               5

<210> SEQ ID NO 152
<211> LENGTH: 10
<212> TYPE: PRT
<213> ORGANISM: Homo sapiens

<400> SEQUENCE: 152

Arg Asp Leu Asn Ala Leu Leu Pro Ala Val
1               5                   10

<210> SEQ ID NO 153
<211> LENGTH: 10
<212> TYPE: PRT
<213> ORGANISM: Homo sapiens

<400> SEQUENCE: 153

Gly Gly Cys Ala Leu Pro Val Ser Gly Ala
1               5                   10

<210> SEQ ID NO 154
<211> LENGTH: 9
<212> TYPE: PRT
<213> ORGANISM: Homo sapiens

<400> SEQUENCE: 154

Gly Ala Ala Gln Trp Ala Pro Val Leu
1               5

<210> SEQ ID NO 155
<211> LENGTH: 9
<212> TYPE: PRT
<213> ORGANISM: Homo sapiens

<400> SEQUENCE: 155

Leu Asp Phe Ala Pro Pro Gly Ala Ser
1               5

<210> SEQ ID NO 156
<211> LENGTH: 11
<212> TYPE: PRT
<213> ORGANISM: Homo sapiens

<400> SEQUENCE: 156

Leu Asp Phe Ala Pro Pro Gly Ala Ser Ala Tyr

```
                1               5                   10
```

<210> SEQ ID NO 157
<211> LENGTH: 9
<212> TYPE: PRT
<213> ORGANISM: Homo sapiens

<400> SEQUENCE: 157

Ser Ala Tyr Gly Ser Leu Gly Gly Pro
1               5

<210> SEQ ID NO 158
<211> LENGTH: 9
<212> TYPE: PRT
<213> ORGANISM: Homo sapiens

<400> SEQUENCE: 158

Pro Ala Pro Pro Pro Pro Pro Pro
1               5

<210> SEQ ID NO 159
<211> LENGTH: 9
<212> TYPE: PRT
<213> ORGANISM: Homo sapiens

<400> SEQUENCE: 159

Ala Cys Arg Tyr Gly Pro Phe Gly Pro
1               5

<210> SEQ ID NO 160
<211> LENGTH: 9
<212> TYPE: PRT
<213> ORGANISM: Homo sapiens

<400> SEQUENCE: 160

Ser Gly Gln Ala Arg Met Phe Pro Asn
1               5

<210> SEQ ID NO 161
<211> LENGTH: 9
<212> TYPE: PRT
<213> ORGANISM: Homo sapiens

<400> SEQUENCE: 161

Arg Met Phe Pro Asn Ala Pro Tyr Leu
1               5

<210> SEQ ID NO 162
<211> LENGTH: 9
<212> TYPE: PRT
<213> ORGANISM: Homo sapiens

<400> SEQUENCE: 162

Pro Ser Cys Leu Glu Ser Gln Pro Ala
1               5

<210> SEQ ID NO 163
<211> LENGTH: 9
<212> TYPE: PRT
<213> ORGANISM: Homo sapiens

<400> SEQUENCE: 163

Asn Gln Gly Tyr Ser Thr Val Thr Phe
1               5

```
<210> SEQ ID NO 164
<211> LENGTH: 9
<212> TYPE: PRT
<213> ORGANISM: Homo sapiens

<400> SEQUENCE: 164

His His Ala Ala Gln Phe Pro Asn His
1               5

<210> SEQ ID NO 165
<211> LENGTH: 9
<212> TYPE: PRT
<213> ORGANISM: Homo sapiens

<400> SEQUENCE: 165

His Ser Phe Lys His Glu Asp Pro Met
1               5

<210> SEQ ID NO 166
<211> LENGTH: 9
<212> TYPE: PRT
<213> ORGANISM: Homo sapiens

<400> SEQUENCE: 166

Cys His Thr Pro Thr Asp Ser Cys Thr
1               5

<210> SEQ ID NO 167
<211> LENGTH: 9
<212> TYPE: PRT
<213> ORGANISM: Homo sapiens

<400> SEQUENCE: 167

Cys Thr Gly Ser Gln Ala Leu Leu Leu
1               5

<210> SEQ ID NO 168
<211> LENGTH: 9
<212> TYPE: PRT
<213> ORGANISM: Homo sapiens

<400> SEQUENCE: 168

Thr Asp Ser Cys Thr Gly Ser Gln Ala
1               5

<210> SEQ ID NO 169
<211> LENGTH: 9
<212> TYPE: PRT
<213> ORGANISM: Homo sapiens

<400> SEQUENCE: 169

Arg Thr Pro Tyr Ser Ser Asp Asn Leu
1               5

<210> SEQ ID NO 170
<211> LENGTH: 10
<212> TYPE: PRT
<213> ORGANISM: Homo sapiens

<400> SEQUENCE: 170

Asn Leu Tyr Gln Met Thr Ser Gln Leu Glu
1               5                   10

<210> SEQ ID NO 171
```

```
<211> LENGTH: 9
<212> TYPE: PRT
<213> ORGANISM: Homo sapiens

<400> SEQUENCE: 171

Trp Asn Gln Met Asn Leu Gly Ala Thr
1               5

<210> SEQ ID NO 172
<211> LENGTH: 9
<212> TYPE: PRT
<213> ORGANISM: Homo sapiens

<400> SEQUENCE: 172

Asn Gln Met Asn Leu Gly Ala Thr Leu
1               5

<210> SEQ ID NO 173
<211> LENGTH: 11
<212> TYPE: PRT
<213> ORGANISM: Homo sapiens

<400> SEQUENCE: 173

Trp Asn Gln Met Asn Leu Gly Ala Thr Leu Lys
1               5                   10

<210> SEQ ID NO 174
<211> LENGTH: 15
<212> TYPE: PRT
<213> ORGANISM: Homo sapiens

<400> SEQUENCE: 174

Cys Met Thr Trp Asn Gln Met Asn Leu Gly Ala Thr Leu Lys Gly
1               5                   10                  15

<210> SEQ ID NO 175
<211> LENGTH: 9
<212> TYPE: PRT
<213> ORGANISM: Homo sapiens

<400> SEQUENCE: 175

Asn Leu Gly Ala Thr Leu Lys Gly Val
1               5

<210> SEQ ID NO 176
<211> LENGTH: 10
<212> TYPE: PRT
<213> ORGANISM: Homo sapiens

<400> SEQUENCE: 176

Leu Gly Ala Thr Leu Lys Gly Val Ala Ala
1               5                   10

<210> SEQ ID NO 177
<211> LENGTH: 8
<212> TYPE: PRT
<213> ORGANISM: Homo sapiens

<400> SEQUENCE: 177

Thr Leu Gly Val Ala Ala Gly Ser
1               5

<210> SEQ ID NO 178
<211> LENGTH: 9
<212> TYPE: PRT
```

```
<213> ORGANISM: Homo sapiens

<400> SEQUENCE: 178

Gly Tyr Glu Ser Asp Asn His Thr Thr
1               5

<210> SEQ ID NO 179
<211> LENGTH: 10
<212> TYPE: PRT
<213> ORGANISM: Homo sapiens

<400> SEQUENCE: 179

Phe Met Cys Ala Tyr Pro Gly Cys Asn Lys
1               5                   10

<210> SEQ ID NO 180
<211> LENGTH: 11
<212> TYPE: PRT
<213> ORGANISM: Homo sapiens

<400> SEQUENCE: 180

Lys Arg Pro Phe Met Cys Ala Tyr Pro Gly Cys
1               5                   10

<210> SEQ ID NO 181
<211> LENGTH: 9
<212> TYPE: PRT
<213> ORGANISM: Homo sapiens

<400> SEQUENCE: 181

Arg Lys Phe Ser Arg Ser Asp His Leu
1               5

<210> SEQ ID NO 182
<211> LENGTH: 10
<212> TYPE: PRT
<213> ORGANISM: Homo sapiens

<400> SEQUENCE: 182

Leu Lys Thr His Thr Thr Arg Thr His Thr
1               5                   10

<210> SEQ ID NO 183
<211> LENGTH: 10
<212> TYPE: PRT
<213> ORGANISM: Homo sapiens

<400> SEQUENCE: 183

Asn Met His Gln Arg Asn His Thr Lys Leu
1               5                   10

<210> SEQ ID NO 184
<211> LENGTH: 9
<212> TYPE: PRT
<213> ORGANISM: Homo sapiens

<400> SEQUENCE: 184

Leu Leu Ala Ala Ile Leu Asp Phe Leu
1               5

<210> SEQ ID NO 185
<211> LENGTH: 10
<212> TYPE: PRT
<213> ORGANISM: Homo sapiens
```

```
<400> SEQUENCE: 185

Cys Leu Gln Gln Pro Glu Gln Gln Gly Val
1               5                   10

<210> SEQ ID NO 186
<211> LENGTH: 9
<212> TYPE: PRT
<213> ORGANISM: Homo sapiens

<400> SEQUENCE: 186

Asp Leu Asn Ala Leu Leu Pro Ala Val
1               5

<210> SEQ ID NO 187
<211> LENGTH: 9
<212> TYPE: PRT
<213> ORGANISM: Homo sapiens

<400> SEQUENCE: 187

Ala Leu Leu Pro Ala Val Pro Ser Leu
1               5

<210> SEQ ID NO 188
<211> LENGTH: 9
<212> TYPE: PRT
<213> ORGANISM: Homo sapiens

<400> SEQUENCE: 188

Val Leu Asp Phe Ala Pro Pro Gly Ala
1               5

<210> SEQ ID NO 189
<211> LENGTH: 9
<212> TYPE: PRT
<213> ORGANISM: Homo sapiens

<400> SEQUENCE: 189

Cys Met Thr Trp Asn Gln Met Asn Leu
1               5

<210> SEQ ID NO 190
<211> LENGTH: 10
<212> TYPE: PRT
<213> ORGANISM: Homo sapiens

<400> SEQUENCE: 190

Gln Ala Arg Met Phe Pro Asn Ala Pro Tyr
1               5                   10

<210> SEQ ID NO 191
<211> LENGTH: 10
<212> TYPE: PRT
<213> ORGANISM: Homo sapiens

<400> SEQUENCE: 191

Ala Leu Arg Asn Pro Thr Ala Cys Pro Leu
1               5                   10

<210> SEQ ID NO 192
<211> LENGTH: 9
<212> TYPE: PRT
<213> ORGANISM: Homo sapiens

<400> SEQUENCE: 192
```

```
Tyr Pro Gly Cys Asn Lys Arg Tyr Phe
1               5
```

<210> SEQ ID NO 193
<211> LENGTH: 15
<212> TYPE: PRT
<213> ORGANISM: Homo sapiens

<400> SEQUENCE: 193

```
Ala Pro Val Leu Asp Phe Ala Pro Pro Gly Ala Ser Ala Tyr Gly
1               5                   10                  15
```

<210> SEQ ID NO 194
<211> LENGTH: 575
<212> TYPE: PRT
<213> ORGANISM: Homo sapiens

<400> SEQUENCE: 194

```
Ser Arg Gln Arg Pro His Pro Gly Ala Leu Arg Asn Pro Thr Ala Cys
1               5                   10                  15

Pro Leu Pro His Phe Pro Pro Ser Leu Pro Pro Thr His Ser Pro Thr
                20                  25                  30

His Pro Pro Arg Ala Gly Thr Ala Ala Gln Ala Pro Gly Pro Arg Arg
            35                  40                  45

Leu Leu Ala Ala Ile Leu Asp Phe Leu Leu Gln Asp Pro Ala Ser
    50                  55                  60

Thr Cys Val Pro Glu Pro Ala Ser Gln His Thr Leu Arg Ser Gly Pro
65                  70                  75                  80

Gly Cys Leu Gln Gln Pro Glu Gln Gln Gly Val Arg Asp Pro Gly Gly
                85                  90                  95

Ile Trp Ala Lys Leu Gly Ala Ala Glu Ala Ser Ala Glu Arg Leu Gln
                100                 105                 110

Gly Arg Arg Ser Arg Gly Ala Ser Gly Ser Glu Pro Gln Gln Met Gly
            115                 120                 125

Ser Asp Val Arg Asp Leu Asn Ala Leu Leu Pro Ala Val Pro Ser Leu
130                 135                 140

Gly Gly Gly Gly Gly Cys Ala Leu Pro Val Ser Gly Ala Ala Gln Trp
145                 150                 155                 160

Ala Pro Val Leu Asp Phe Ala Pro Pro Gly Ala Ser Ala Tyr Gly Ser
                165                 170                 175

Leu Gly Gly Pro Ala Pro Pro Ala Pro Pro Pro Pro Pro Pro
            180                 185                 190

Pro Pro His Ser Phe Ile Lys Gln Glu Pro Ser Trp Gly Gly Ala Glu
    195                 200                 205

Pro His Glu Glu Gln Cys Leu Ser Ala Phe Thr Val His Phe Ser Gly
    210                 215                 220

Gln Phe Thr Gly Thr Ala Gly Ala Cys Arg Tyr Gly Pro Phe Gly Pro
225                 230                 235                 240

Pro Pro Pro Ser Gln Ala Ser Ser Gly Gln Ala Arg Met Phe Pro Asn
                245                 250                 255

Ala Pro Tyr Leu Pro Ser Cys Leu Glu Ser Gln Pro Ala Ile Arg Asn
                260                 265                 270

Gln Gly Tyr Ser Thr Val Thr Phe Asp Gly Thr Pro Ser Tyr Gly His
            275                 280                 285

Thr Pro Ser His His Ala Ala Gln Phe Pro Asn His Ser Phe Lys His
        290                 295                 300
```

```
Glu Asp Pro Met Gly Gln Gln Gly Ser Leu Gly Glu Gln Gln Tyr Ser
305                 310                 315                 320

Val Pro Pro Val Tyr Gly Cys His Thr Pro Thr Asp Ser Cys Thr
            325                 330                 335

Gly Ser Gln Ala Leu Leu Arg Thr Pro Tyr Ser Ser Asp Asn Leu
                340                 345                 350

Tyr Gln Met Thr Ser Gln Leu Glu Cys Met Thr Trp Asn Gln Met Asn
            355                 360                 365

Leu Gly Ala Thr Leu Lys Gly Val Ala Ala Gly Ser Ser Ser Val
370                 375                 380

Lys Trp Thr Glu Gly Gln Ser Asn His Ser Thr Gly Tyr Glu Ser Asp
385                 390                 395                 400

Asn His Thr Thr Pro Ile Leu Cys Gly Ala Gln Tyr Arg Ile His Thr
                405                 410                 415

His Gly Val Phe Arg Gly Ile Gln Asp Val Arg Val Pro Gly Val
                420                 425                 430

Ala Pro Thr Leu Val Arg Ser Ala Ser Glu Thr Ser Glu Lys Arg Pro
            435                 440                 445

Phe Met Cys Ala Tyr Pro Gly Cys Asn Lys Arg Tyr Phe Lys Leu Ser
450                 455                 460

His Leu Gln Met His Ser Arg Lys His Thr Gly Glu Lys Pro Tyr Gln
465                 470                 475                 480

Cys Asp Phe Lys Asp Cys Glu Arg Arg Phe Ser Arg Ser Asp Gln Leu
                485                 490                 495

Lys Arg His Gln Arg Arg His Thr Gly Val Lys Pro Phe Gln Cys Lys
            500                 505                 510

Thr Cys Gln Arg Lys Phe Ser Arg Ser Asp His Leu Lys Thr His Thr
            515                 520                 525

Arg Thr His Thr Gly Lys Thr Ser Glu Lys Pro Phe Ser Cys Arg Trp
530                 535                 540

Pro Ser Cys Gln Lys Lys Phe Ala Arg Ser Asp Glu Leu Val Arg His
545                 550                 555                 560

His Asn Met His Gln Arg Asn Met Thr Lys Leu Gln Leu Ala Leu
                565                 570                 575

<210> SEQ ID NO 195
<211> LENGTH: 449
<212> TYPE: PRT
<213> ORGANISM: Homo sapiens

<400> SEQUENCE: 195

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
                20                  25                  30

Gln Trp Ala Pro Val Leu Asp Phe Ala Pro Pro Gly Ala Ser Ala Tyr
            35                  40                  45

Gly Ser Leu Gly Gly Pro Ala Pro Pro Ala Pro Pro Pro Pro Pro Pro
        50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110
```

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
        130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
        210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Ser Asn His Ser Thr Gly Tyr Glu
        260                 265                 270

Ser Asp Asn His Thr Thr Pro Ile Leu Cys Gly Ala Gln Tyr Arg Ile
            275                 280                 285

His Thr His Gly Val Phe Arg Gly Ile Gln Asp Val Arg Arg Val Pro
        290                 295                 300

Gly Val Ala Pro Thr Leu Val Arg Ser Ala Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
        340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
        370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
        420                 425                 430

Arg His His Asn Met His Gln Arg Asn Met Thr Lys Leu Gln Leu Ala
        435                 440                 445

Leu

<210> SEQ ID NO 196
<211> LENGTH: 453
<212> TYPE: PRT
<213> ORGANISM: Homo sapiens

<400> SEQUENCE: 196

Ala Ala Glu Ala Ser Ala Glu Arg Leu Gln Gly Arg Arg Ser Arg Gly
1               5                   10                  15

Ala Ser Gly Ser Glu Pro Gln Gln Met Gly Ser Asp Val Arg Asp Leu
                20                  25                  30

-continued

Asn Ala Leu Leu Pro Ala Val Pro Ser Leu Gly Gly Gly Gly Cys
         35                  40                  45

Ala Leu Pro Val Ser Gly Ala Ala Gln Trp Ala Pro Val Leu Asp Phe
 50                  55                  60

Ala Pro Pro Gly Ala Ser Ala Tyr Gly Ser Leu Gly Gly Pro Ala Pro
 65                  70                  75                  80

Pro Pro Ala Pro Pro Pro Pro Pro Pro Pro His Ser Phe Ile
             85                  90                  95

Lys Gln Glu Pro Ser Trp Gly Gly Ala Glu Pro His Glu Glu Gln Cys
                100                 105                 110

Leu Ser Ala Phe Thr Val His Phe Ser Gly Gln Phe Thr Gly Thr Ala
             115                 120                 125

Gly Ala Cys Arg Tyr Gly Pro Phe Gly Pro Pro Pro Ser Gln Ala
         130                 135                 140

Ser Ser Gly Gln Ala Arg Met Phe Pro Asn Ala Pro Tyr Leu Pro Ser
145                 150                 155                 160

Cys Leu Glu Ser Gln Pro Ala Ile Arg Asn Gln Gly Tyr Ser Thr Val
                 165                 170                 175

Thr Phe Asp Gly Thr Pro Ser Tyr Gly His Thr Pro Ser His His Ala
         180                 185                 190

Ala Gln Phe Pro Asn His Ser Phe Lys His Glu Asp Pro Met Gly Gln
     195                 200                 205

Gln Gly Ser Leu Gly Glu Gln Gln Tyr Ser Val Pro Pro Pro Val Tyr
         210                 215                 220

Gly Cys His Thr Pro Thr Asp Ser Cys Thr Gly Ser Gln Ala Leu Leu
225                 230                 235                 240

Leu Arg Thr Pro Tyr Ser Ser Asp Asn Leu Tyr Gln Met Thr Ser Gln
                 245                 250                 255

Leu Glu Cys Met Thr Trp Asn Gln Met Asn Leu Gly Ala Thr Leu Lys
             260                 265                 270

Gly His Ser Thr Gly Tyr Glu Ser Asp Asn His Thr Thr Pro Ile Leu
         275                 280                 285

Cys Gly Ala Gln Tyr Arg Ile His Thr His Gly Val Phe Arg Gly Ile
     290                 295                 300

Gln Asp Val Arg Arg Val Pro Gly Val Ala Pro Thr Leu Val Arg Ser
305                 310                 315                 320

Ala Ser Glu Thr Ser Glu Lys Arg Pro Phe Met Cys Ala Tyr Pro Gly
                 325                 330                 335

Cys Asn Lys Arg Tyr Phe Lys Leu Ser His Leu Gln Met His Ser Arg
             340                 345                 350

Lys His Thr Gly Glu Lys Pro Tyr Gln Cys Asp Phe Lys Asp Cys Glu
         355                 360                 365

Arg Arg Phe Ser Arg Ser Asp Gln Leu Lys Arg His Gln Arg Arg His
     370                 375                 380

Thr Gly Val Lys Pro Phe Gln Cys Lys Thr Cys Gln Arg Lys Phe Ser
385                 390                 395                 400

Arg Ser Asp His Leu Lys Thr His Thr Arg Thr His Thr Gly Glu Lys
                 405                 410                 415

Pro Phe Ser Cys Arg Trp Pro Ser Cys Gln Lys Lys Phe Ala Arg Ser
             420                 425                 430

Asp Glu Leu Val Arg His His Asn Met His Gln Arg Asn Met Thr Lys
         435                 440                 445

Leu Gln Leu Ala Leu
    450

<210> SEQ ID NO 197
<211> LENGTH: 514
<212> TYPE: PRT
<213> ORGANISM: Homo sapiens

<400> SEQUENCE: 197

Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45

Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Ala Pro
        115                 120                 125

Pro Pro Pro Pro Pro Pro Pro His Ser Phe Ile Lys Gln Glu Pro
    130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Ser Gln Ala Ser Ser Gly Gln
            180                 185                 190

Ala Arg Met Phe Pro Asn Ala Pro Tyr Leu Pro Ser Cys Leu Glu Ser
        195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Pro Val Tyr Gly Cys His Thr
            260                 265                 270

Pro Thr Asp Ser Cys Thr Gly Ser Gln Ala Leu Leu Leu Arg Thr Pro
        275                 280                 285

Tyr Ser Ser Asp Asn Leu Tyr Gln Met Thr Ser Gln Leu Glu Cys Met
    290                 295                 300

Thr Trp Asn Gln Met Asn Leu Gly Ala Thr Leu Lys Gly Val Ala Ala
305                 310                 315                 320

Gly Ser Ser Ser Ser Val Lys Trp Thr Glu Gly Gln Ser Asn His Ser
                325                 330                 335

Thr Gly Tyr Glu Ser Asp Asn His Thr Thr Pro Ile Leu Cys Gly Ala
            340                 345                 350

Gln Tyr Arg Ile His Thr His Gly Val Phe Arg Gly Ile Gln Asp Val
        355                 360                 365

```
Arg Arg Val Pro Gly Val Ala Pro Thr Leu Val Arg Ser Ala Ser Glu
    370                 375                 380

Thr Ser Glu Lys Arg Pro Phe Met Cys Ala Tyr Pro Gly Cys Asn Lys
385                 390                 395                 400

Arg Tyr Phe Lys Leu Ser His Leu Gln Met His Ser Arg Lys His Thr
                405                 410                 415

Gly Glu Lys Pro Tyr Gln Cys Asp Phe Lys Asp Cys Glu Arg Arg Phe
                420                 425                 430

Ser Arg Ser Asp Gln Leu Lys Arg His Gln Arg Arg His Thr Gly Val
            435                 440                 445

Lys Pro Phe Gln Cys Lys Thr Cys Gln Arg Lys Phe Ser Arg Ser Asp
    450                 455                 460

His Leu Lys Thr His Thr Arg Thr His Thr Gly Glu Lys Pro Phe Ser
465                 470                 475                 480

Cys Arg Trp Pro Ser Cys Gln Lys Lys Phe Ala Arg Ser Asp Glu Leu
                485                 490                 495

Val Arg His His Asn Met His Gln Arg Asn Met Thr Lys Leu Gln Leu
                500                 505                 510

Ala Leu
```